US009596540B2

(12) United States Patent
Tani et al.

(10) Patent No.: US 9,596,540 B2
(45) Date of Patent: Mar. 14, 2017

(54) ACTIVE NOISE REDUCTION DEVICE AND ACTIVE NOISE REDUCTION METHOD

(71) Applicant: Panasonic Intellectual Property Management Co., Ltd., Osaka (JP)

(72) Inventors: Mitsuhiro Tani, Osaka (JP); Toshiyuki Funayama, Mie (JP); Mitsuru Kaitou, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 275 days.

(21) Appl. No.: 14/391,530

(22) PCT Filed: Jun. 25, 2013

(86) PCT No.: PCT/JP2013/003951
§ 371 (c)(1),
(2) Date: Oct. 9, 2014

(87) PCT Pub. No.: WO2014/006846
PCT Pub. Date: Jan. 9, 2014

(65) Prior Publication Data

US 2015/0063581 A1 Mar. 5, 2015

(30) Foreign Application Priority Data

Jul. 2, 2012 (JP) ................................ 2012-148243
Sep. 28, 2012 (JP) ................................ 2012-215888

(51) Int. Cl.

| | |
|---|---|
| ***G10K 11/16*** | (2006.01) |
| ***H03B 29/00*** | (2006.01) |
| ***A61F 11/06*** | (2006.01) |
| ***H04R 3/02*** | (2006.01) |
| ***G10K 11/178*** | (2006.01) |
| ***H04R 3/00*** | (2006.01) |

(52) U.S. Cl.
CPC ............ *H04R 3/02* (2013.01); *G10K 11/178* (2013.01); *G10K 11/1784* (2013.01); *H04R 3/00* (2013.01);
(Continued)

(58) Field of Classification Search
CPC ............ G10K 11/178; G10K 11/1784; G10K 2210/1282; G10K 2210/3055;
(Continued)

(56) References Cited

FOREIGN PATENT DOCUMENTS

JP 06-130970 A 5/1994
JP 07-219565 A 8/1995
(Continued)

OTHER PUBLICATIONS

Kuo Sen M et al. "Active Noise Control: A Tutorial Review", Proceedings of the IEEE, IEEE. New York, US, vol. 87, No. 6, Jun. 1999 (Jun. 1999), pp. 943-973.*
(Continued)

*Primary Examiner* — Paul S Kim
(74) *Attorney, Agent, or Firm* — McDermott Will & Emery LLP

(57) ABSTRACT

An active noise reduction device is used with a secondary noise source that generates a secondary noise and an error signal source that outputs an error signal corresponding to a residual sound caused by interference between the secondary noise and a noise. A μ-adjustment unit calculates a step-size parameter for updating a filter coefficient of an adaptive filter by multiplying a standard step-size parameter by a ratio of a standard representative input value corresponding to amplitude of a signal to a representative input value corresponding to the amplitude of the signal.

11 Claims, 17 Drawing Sheets

(52) U.S. Cl.
CPC ................ *G10K 2210/1282* (2013.01); *G10K 2210/3054* (2013.01); *G10K 2210/3055* (2013.01); *H04R 2460/01* (2013.01); *H04R 2499/13* (2013.01)

(58) Field of Classification Search
CPC .............. G10K 2210/3054; H04R 3/02; H04R 2499/13; H04R 3/00; H04R 2460/01
USPC ................................................ 381/71.2, 71.1
See application file for complete search history.

(56) References Cited

FOREIGN PATENT DOCUMENTS

| | | | |
|---|---|---|---|
| JP | 08-179782 | A | 7/1996 |
| JP | 10-307590 | A | 11/1998 |
| JP | 2001-142468 | A | 5/2001 |
| JP | 2001-234728 | A | 8/2001 |
| JP | 2004-064681 | A | 2/2004 |
| JP | 2012-123135 | | 6/2012 |

OTHER PUBLICATIONS

The Extended European Search Report dated Jan. 15, 2016 for the related European Patent Application No. 13813616.3.
Kuo S M et al: "Active Noise Control: A Tutorial Review", Proceedings of the IEEE, IEEE New York, US, vol. 87, No. 6, Jun. 1, 1999 (Jun. 1, 1999), pp. 943-973.
International Search Report issued in International Application No. PCT/JP2013/003951 mailed Aug. 13, 2013, with English translation.

* cited by examiner

ACTIVE NOISE REDUCTION DEVICE AND ACTIVE NOISE REDUCTION METHOD

RELATED APPLICATIONS

This application is the U.S. National Phase under 35 U.S.C. §371 of International Application No. PCT/JP2013/003951, filed on Jun. 25, 2013, which in turn claims the benefit of Japanese Application No. 2012-148243, filed on Jul. 2, 2012 and Japanese Application No. 2012-215888, filed on Sep. 28, 2012, the disclosures of which are incorporated by reference herein.

TECHNICAL FIELD

The present invention relates to an active noise reduction device and an active noise reduction method for reducing a noise by causing a canceling sound to interfere with the noise.

BACKGROUND ART

In recent years, active noise reduction devices have been put in practical use. Such an active noise reduction device cancels a noise that is generated during a drive of a vehicle, such as an automobile, in a passenger compartment, and reduces the noise audible to a driver and a passenger. FIG. 19 is a block diagram of conventional active noise reduction device 901 for reducing noise N0 that is audible in space S1, such as the passenger compartment. Active noise reduction device 901 includes reference signal source 1, secondary noise source 2, error signal source 3, and signal-processing device 904.

Reference signal source 1 is an acceleration sensor installed into a chassis of a vehicle or a sensor, such as a microphone, for detecting vibration installed in space S1. Reference signal source 1 outputs a reference signal x(i) that has a correlation with noise N0. Secondary noise source 2 is a loudspeaker installed in space S1 for generating secondary noise N1. Error signal source 3 is a microphone installed in space S1 for outputting an error signal e(i) corresponding to a residual sound caused by interference between noise N0 and secondary noise N1 in space S1.

Signal-processing device 904 includes adaptive filter (ADF) 5, simulated acoustic transfer characteristic filter (hereinafter, Chat unit) 6, and least-mean-square (LMS) operation unit 7. Signal-processing device 904 operates at discrete time intervals of a sampling period $T_s$.

ADF 5 includes a finite impulse response (FIR) type adaptive filter composed of N filter coefficients w(k) with values updated every sampling period $T_s$ (where k=0, 1, . . . , N−1). The filter coefficient w(k,n) at the current n-th step is updated by a filtered X-LMS (FxLMS) algorithm described in NPL 1 and NPL 2. ADF 5 determines a secondary noise signal y(n) at the current n-th step using the filter coefficient w(k,n) and the reference signal x(i) by performing a filtering operation, that is, a convolution operation expressed by formula (1).

$$y(n) = \sum_{k=0}^{N-1} w(k, n) \cdot x(n-k) \quad (1)$$

Chat unit 6 has an FIR type filter composed of a time-invariant filter coefficient C^ that simulates an acoustic transfer characteristic C(i) between an output port for outputting the secondary noise signal y(i) and an input port for acquiring the error signal e(i) of signal-processing device 904. Chat unit 6 produces a filtered reference signal r(i) obtained by performing the filtering operation, that is, the convolution operation on the filter coefficient C^ and the reference signal x(i).

LMS operation unit 7 updates the filter coefficient W(n) of ADF 5 at the current time by formula (2) using a filtered reference signal R(N), the error signal e(n), and a step-size parameter μ at the current n-th step. LMS operation unit 7 then calculates the filter coefficient W(n+1) at the next (n+1)-th step that is the next time.

$$W(n+1)=W(n)-\mu\cdot e(n)\cdot R(n) \quad (2)$$

The filter coefficient W(n) of ADF 5 is a vector with N rows and one column composed of N filter coefficients w(k,n) at the current n-th step, and is expressed by formula (3).

$$W(n)=[w(0,n),w(1,n), \ldots ,w(N-1,n)]^T \quad (3)$$

The filtered reference signal R (n) is a vector with N rows and one column, the vector representing N filtered reference signals r(i) from the current time to the past by (N−1) steps.

Active noise reduction device 901 can determine an optimal secondary noise signal y(i) that cancels noise N0 at a position of error signal source 3 by updating the filter coefficient W(i) of ADF 5 every sampling period $T_s$ by formula (2), thereby reducing noise N0 in space S1.

The step-size parameter μ is a parameter for adjusting a converging speed, i.e., an amount of the update of the coefficient ADF 5 at once, and is a parameter important for determining stability of adaptive operations. In order for active noise reduction device 901 to perform stable operation, it is necessary to set the step-size parameter μ to a value such that the filter coefficient W(i) does not diverge even when the reference signal x(i) has a maximum value. A condition of the step-size parameter μ that the filter coefficient W(i) converges is expressed as formula (4) described in, e.g. NPL 3.

$$0 < \mu < \frac{2}{\lambda_{MAX}} \quad (4)$$

$\lambda_{MAX}$ is a maximum eigenvalue of an autocorrelation matrix of the filtered reference signal R(n). In common active noise reduction device 901 using the FxLMS algorithm, a value of the step-size parameter μ is determined in consideration of a level variation of a reference signal and a noise based on formula (4). Since priority is usually given to stability, the step-size parameter μ may be often set to a smaller value to allow a certain margin.

However, when the step-size parameter μ is set smaller, an amount of the update of the filter coefficient W(i) each step becomes smaller, and it takes a time to achieve an effect of fully reducing noise N0.

Therefore, for example, PTLs 1 to 3 that determine the step-size parameter μ in accordance with a residual or an amount of convergence disclose conventional active noise reduction devices that cause the filter coefficient W(i) to converge quickly by making the step-size parameter μ variable, without fixing the step-size parameter μ.

CITATION LIST

Patent Literature

PTL 1: Japanese Patent Laid-Open Publication No. 2004-64681

PTL 2: Japanese Patent Laid-Open Publication No. 06-130970

PTL 3: Japanese Patent Laid-Open Publication No. 08-179782

PTL 4: Japanese Patent Laid-Open Publication No. 2001-142468

PTL 5: Japanese Patent Laid-Open Publication No. 10-307590

Non-Patent Literature

NPL 1: Barnard Widrow and Samuel D. Stearns, "ADAPTIVE SIGNAL PROCESSING", Prentice Hall, 1985 (P288)

NPL 2: P. A. Nelson and S. J. Elliott, "Active Control of Sound", Academic Press, 1992 (P196)

NPL 3: Scott D. Snyder and Colin H. Hansen, "The Effect of Transfer Function Estimation Errors on the Filtered-X LMS Algorithm", IEEE, TRANSACTIONS ON SIGNAL PROCESSING, vol. 42, No. 4, April, 1994

SUMMARY

An active noise reduction device is configured to be used with a reference signal source, a secondary noise source, and an error signal source. The reference signal source outputs a reference signal having a correlation with a noise. The secondary noise source generates a secondary noise corresponding to a secondary noise signal. The error signal source outputs an error signal corresponding to a residual sound caused by interference between the secondary noise and the noise. The active noise reduction device includes a signal-processing device which includes a first input port being configured to receive the reference signal, a second input port being configured to receive the error signal, and an output port being configured to output the secondary noise signal, an adaptive filter, a simulated acoustic transfer characteristic filter, a least-mean-square operation unit, and a μ-adjustment unit. The adaptive filter is configured to output the secondary noise signal based on the reference signal. The simulated acoustic transfer characteristic filter is configured to correct the reference signal with a simulated acoustic transfer characteristic that simulates an acoustic transfer characteristic from the output port to the second input port so as to output a filtered reference signal. The least-mean-square operation unit is configured to update a filter coefficient of the adaptive filter by using the error signal, the filtered reference signal, and a step-size parameter. The μ-adjustment unit configured to determine the step-size parameter. The μ-adjustment unit is operable to calculate a representative input value corresponding to amplitude of at least one signal of the reference signal, the filtered reference signal, and the error signal. The μ-adjustment unit is operable to store a standard representative input value and a predetermined standard step-size parameter, the standard representative input value being a representative input value when the amplitude of the at least one signal of the reference signal, the filtered reference signal, and the error signal is predetermined amplitude, the predetermined standard step-size parameter being a value of the step-size parameter to which the filter coefficient converges when the representative input value is the standard representative input value. The μ-adjustment unit is operable to calculate the step-size parameter by multiplying the standard step-size parameter by a ratio of the standard representative input value to the representative input value. The active noise reduction device having the above configuration reduces the noise Another active noise reduction device is configured to be used with a secondary noise source and an error signal source. The secondary noise source generates a secondary noise corresponding to a secondary noise signal. The error signal source outputs an error signal corresponding to a residual sound caused by interference between the secondary noise and a noise. The active noise reduction device includes a signal-processing device which includes an input port being configured to receive the error signal, an output port being configured to output the secondary noise signal, an adaptive filter, a simulated acoustic transfer characteristic filter, a least-mean-square operation unit, and a p-adjustment unit. The adaptive filter is configured to output the secondary noise signal based on the error signal. The simulated acoustic transfer characteristic filter is configured to correct the error signal with a simulated acoustic transfer characteristic that simulates an acoustic transfer characteristic from the output port to the input port so as to output a filtered error signal. The least-mean-square operation unit is configured to update a filter coefficient of the adaptive filter by using the error signal, the filtered error signal, and a step-size parameter. The μ-adjustment unit is configured to determine the step-size parameter. The μ-adjustment unit is operable to calculate a representative input value corresponding to amplitude of at least one signal of the error signal and the filtered error signal. The μ-adjustment unit is operable to store a standard representative input value and a predetermined standard step-size parameter, the standard representative input value being a representative input value when the amplitude of the at least one signal of the error signal and the filtered error signal is predetermined amplitude, the predetermined standard step-size parameter being a value of the step-size parameter to which the filter coefficient converges when the representative input value is the standard representative input value. The μ-adjustment unit is operable to calculate the step-size parameter by multiplying the standard step-size parameter by a ratio of the standard representative input value to the representative input value so as to reduce the noise.

An active noise reduction method can reduce the noise by performing one of the above-described operations.

DETAIL DESCRIPTION OF PREFERRED EMBODIMENTS

Exemplary Embodiment 1

Figure 1:
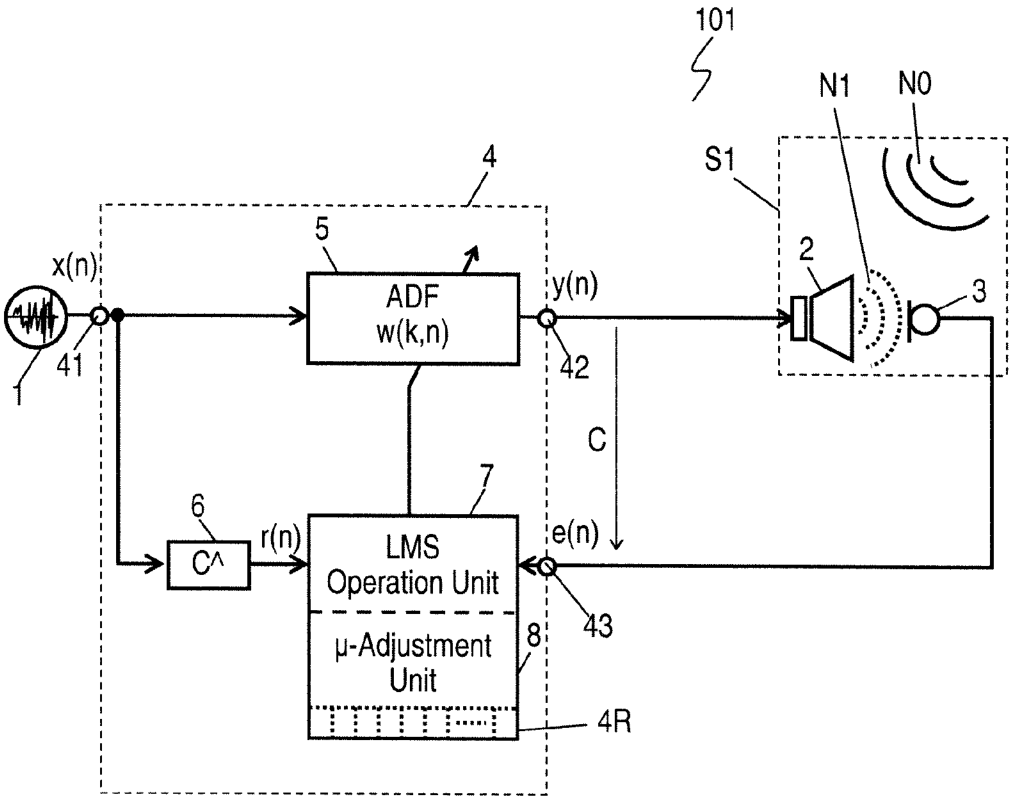
FIG. 1 is a block diagram of an active noise reduction device according to Exemplary Embodiment 1 of the present invention.
Figure 2:
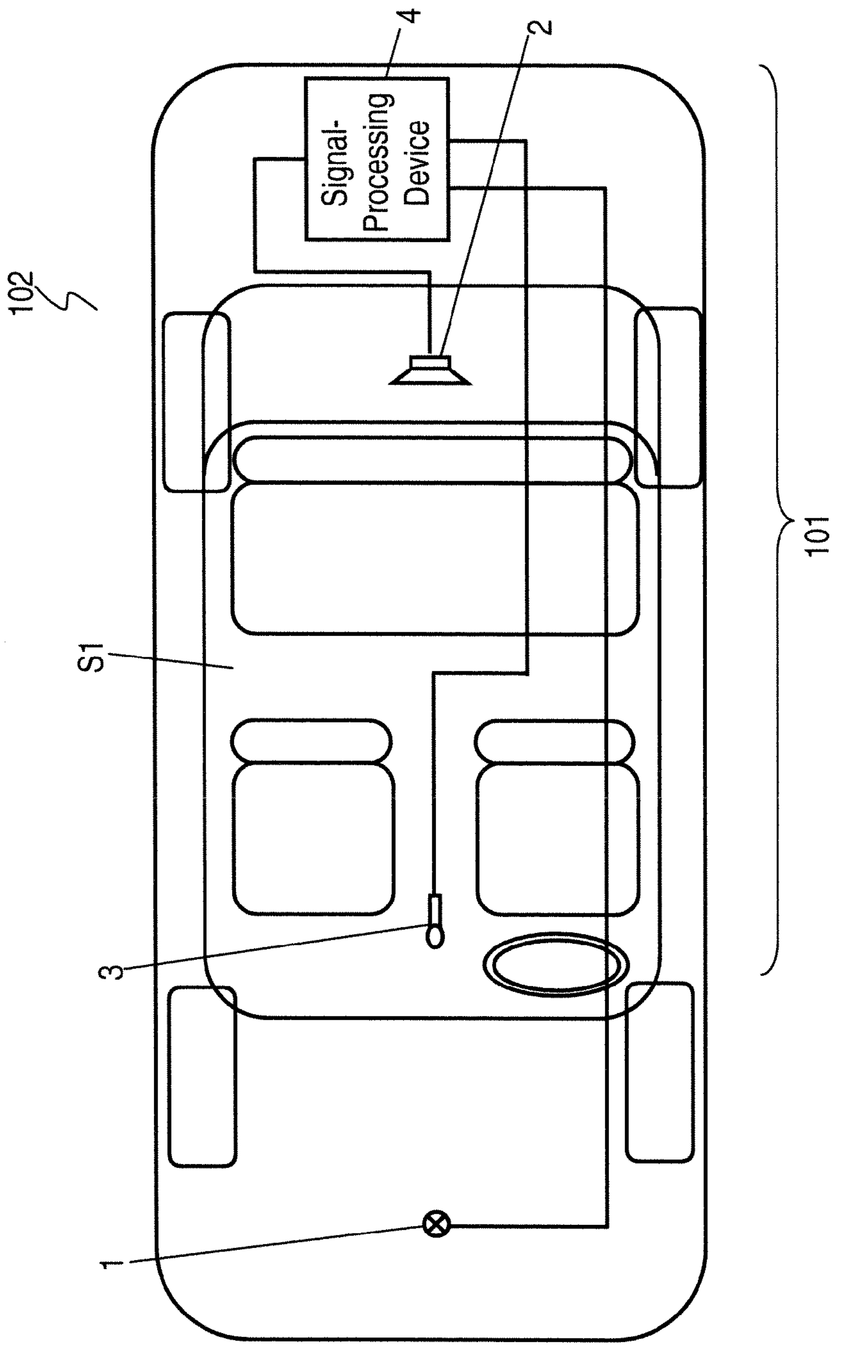
FIG. 2 is a schematic diagram of a movable body having the active noise reduction device according to Embodiment 1 mounted thereto.

FIG. 1 is a block diagram of active noise reduction device 101 according to Exemplary Embodiment 1 of the present invention. FIG. 2 is a schematic diagram of movable body 102 having active noise reduction device 101 mounted thereto. Movable body 102 according to Embodiment 1 is a vehicle that has space S1, such as a passenger compartment. Active noise reduction device 101 includes reference signal source 1, secondary noise source 2, error signal source 3, and signal-processing device 4. Signal-processing device 4 outputs a secondary noise signal y(i) in accordance with a reference signal x(i) and an error signal e(i). Secondary noise source 2 causes secondary noise N1 generated by reproducing the secondary noise signal y(i) to interfere with noise N0 generated in space S1, thereby reducing noise N0.

Reference signal source 1 is a transducer for outputting the reference signal x(i) that has a correlation with noise N0, and is installed in a chassis of movable body 102. That is, reference signal source 1 is a transducer that functions as a reference signal generator for generating the reference signal x(i). Reference signal source 1 may be installed into a noise source or a noise transfer path of noise N0, such as an engine, an axle, a tire, a tire house, a knuckle, an arm, a sub-frame, or a body. Reference signal source 1 may be implemented by, e.g. an acceleration sensor or a microphone, for detecting vibration or sound, and may use a signal related to an operation of the noise source, such as tacho-pulses, with respect to the engine.

Secondary noise source 2 is a transducer for outputting the secondary noise signal y(i) and generating secondary noise N1, and may be implemented by a loudspeaker installed in space S1. Secondary noise source 2 may be an actuator installed in a structure, such as a roof of movable body 102. In this case, a sound emitted from the structure excited by an output of the actuator corresponds to secondary noise N1. Secondary noise source 2 often includes a power amplifier for amplifying the secondary noise signal y(i), or is often driven by the secondary noise signal y(i) amplified by a power amplifying device provided outside. According to Embodiment 1, the power amplifier is included in secondary noise source 2, which does not limit the embodiment.

Error signal source 3 is a transducer, such as a microphone, for detecting a residual sound generated when noise N0 interfere with secondary noise N1 in space S1, and for outputting the error signal e(i) corresponding to the residual sound. Error signal source 3 is preferably installed in space S1 in which noise N0 is to be reduced.

Signal-processing device 4 includes input port 41 for receiving the reference signal x(i), input port 43 for receiving the error signal e(i), output port 42 for outputting the secondary noise signal y(i), and an arithmetic operation unit for calculating the secondary noise signal y(i) based on the reference signal x(i) and the error signal e(i). Input ports 41 and 43 and output port 42 may include a filter, such as a low pass filter, and a signal adjuster for adjusting signal amplitude and phase. The arithmetic operation unit is implemented by an arithmetic operation device, such as a microcomputer or a digital signal processor (DSP), operating at discrete time intervals of a sampling period $T_s$. The arithmetic operation unit includes at least adaptive filter (ADF) 5, simulated acoustic transfer characteristic filter (hereinafter, Chat unit) 6, least-mean-square (LMS) operation unit 7, and μ-adjustment unit 8 for calculating a step-size parameter.

ADF 5 includes a finite impulse response (FIR) filter that includes N filter coefficients w(k) with values updated by a filtered X-LMS (FxLMS) algorithm every sampling period $T_s$ (where k=0, 1, . . . , N−1). ADF 5 determines the secondary noise signal y(n) at the current n-th step by performing a filtering operation, that is, a convolution operation expressed by formula (5) on the filter coefficient w(k,n) and the reference signal x(i).

$$y(n) = \sum_{k=0}^{N-1} w(k, n) \cdot x(n-k) \tag{5}$$

Chat unit 6 has a filter coefficient C^(i) that simulates an acoustic transfer characteristic C(i) between output port 42 and input port 43 for the error signal e(i). In addition to an acoustic characteristic of space S1 and a characteristic of secondary noise source 2 between output port 42 and input port 43 for the error signal e(i), the acoustic transfer characteristic C(i) may include a characteristic of a filter included in output port 42 and input port 43, and a delay of a signal caused by digital-to-analog conversion and analog-to-digital conversion. According to Embodiment 1, Chat unit 6 is implemented by an FIR filter that includes $N_c$ time-invariant filter coefficients $c\hat{}(k_c)$ (where $k_c$=0, 1, . . . , $N_c$−1). The filter coefficient C^ of Chat unit 6 is a vector with $N_c$ rows and one column expressed by formula (6)

$$C\hat{} = [c\hat{}(0), c\hat{}(1), \ldots, c\hat{}(N_c-1)]^T \tag{6}$$

Chat unit 6 may have time-variant filter coefficients $c\hat{}(k_c,n)$ that are updated or corrected by techniques described in PTL 4 and PTL 5.

Chat unit 6 produces a filtered reference signal r(n) that is obtained by performing the filtering operation, that is, the convolution operation expressed by formula (7) on the filter coefficient C^ expressed by formula (6) and the reference signal X(n).

$$r(n) = \sum_{k_c=0}^{N_c-1} c\hat{}(k_c)\cdot x(n-k_c) = C^{\wedge T} X(n) \quad (7)$$

The reference signal X(n) is a vector expressed by formula (8) with $N_c$ rows and one column composed of $N_c$ reference signals x(i) from the current n-th step to the past by ($N_c$−1) steps.

$$X(n)=[x(n),x(n-1), \ldots ,x(n-(N_c-1))]^T \quad (8)$$

The μ-adjustment unit 8 outputs a step-size parameter μ(n) at the current n-th step based on a predetermined standard step-size parameter $\mu_{REF}$ that is a standard step-size parameter determined in advance, and on at least one of the reference signal x(i), the filtered reference signal r(i), and the error signal e(i).

LMS operation unit 7 updates the filter coefficient W(n) of ADF 5 by the FxLMS algorithm using a filtered reference signal R(n), the error signal e(n), and the step-size parameter μ(n) at the current n-th step. LMS operation unit 7 then calculates the filter coefficient W(n+1) at the (n+1)-th step that is the next time by formula (9).

$$W(n+1)=W(n)-\mu(n)\cdot e(n)\cdot R(n) \quad (9)$$

The filter coefficient W(n) of ADF 5 is a vector with N rows and one column composed of N filter coefficients w(k,n) at the current n-th step, and is expressed by formula (10) (where k=0, 1, . . . , N−1).

$$W(n)=[w(0,n),w(1,n), \ldots ,w(N-1,n)]^T \quad (10)$$

The filtered reference signal R(n) is a vector with N rows and one column composed of N filtered reference signals r(i) from the current n-th step to the past by (N−1) steps, and is expressed by formula (11).

$$R(n)=[r(n),r(n-1), \ldots ,r(n-(N-1))]^T \quad (11)$$

As described above, active noise reduction device 101 can determine an optimal secondary noise signal y(i) that cancels noise N0 at a position of error signal source 3 by updating the filter coefficient W(i) of ADF 5 every sampling period $T_s$ based on formula (9), thereby reducing noise N0 in space S1.

An operation of μ-adjustment unit 8 will be detailed below. The step-size parameter μ is a parameter important for adjusting a converging characteristic of the filter coefficient W(i) by the LMS algorithm. The converging characteristic is often discussed in association with an eigenvalue λ(l) of an autocorrelation matrix of the filtered reference signal r(i) (where l=0, 1, . . . , $N_l$−1). In order to perform the adaptive operation stably, that is, in order to cause a mean squared error to converge, the step-size parameter μ and a maximum eigenvalue $\lambda_{MAX}$ of the autocorrelation matrix satisfy the relationship of formula (12).

$$0 < \mu < \frac{2}{\lambda_{MAX}} \quad (12)$$

In the case that active noise reduction device 101 is mounted particularly into movable body 102, the filtered reference signal r(i) changes with time in response to a change of noise N0 changes, i.e., a change of reference signal x(i). In order to set a value of the filter coefficient W(i) which does not diverge in any driving condition, the step-size parameter satisfies formula (12) at the current n-th step with respect to the maximum eigenvalue $\lambda_{MAX}$ (n) of the autocorrelation matrix of the filtered reference signal R(n) used by LMS operation unit 7. The maximum value of the maximum eigenvalue $\lambda_{MAX}$(n) may be predicted, and then, a value of approximately 1/10 to 1/1000 of the maximum value is selected as the step-size parameter μ. In contrast, when the step-size parameter μ is smaller, an amount of update of the filter coefficient W(i) for each step become smaller, and reduces a converging speed. A time constant of the converging speed of the LMS algorithm is proportional to 1/μ. The step-size parameter μ upon being smaller prevents a noise reduction effect from following a change of noise N0 caused by the driving condition. Furthermore, since the amount of the update of the filter coefficient W(i) becomes smaller as noise N0 in the driving condition is smaller, the updating of an inappropriate filter coefficient W(i) may be delayed and allows that a state in which a sound is enlarged by secondary noise N1 to continue. Therefore, in active noise reduction device 101 according to Embodiment 1, μ-adjustment unit 8 adjusts the step-size parameter to an optimal value at each step.

The μ-adjustment unit 8 stores a standard representative input value $d_{REF}$ and the standard step-size parameter $\mu_{REF}$. The standard representative input value $d_{REF}$ is an indicator for indicating amplitude of a standard filtered reference signal $r_{REF}$(i) that is the filtered reference signal r(i) in a standard driving condition of movable body 102. Furthermore, μ-adjustment unit 8 determines a representative input value d(i) that is an indicator for indicating amplitude of the filtered reference signal r(i) corresponding to the standard representative input value $d_{REF}$.

The μ-adjustment unit 8 calculates the step-size parameter μ(n) at the n-th step based on the stored standard representative input value $d_{REF}$, the standard step-size parameter $\mu_{REF}$, and the representative input value d(n).

First, an operation of determining the standard representative input value $d_{REF}$ and the standard step-size parameter $\mu_{REF}$ will be described. According to Embodiment 1, a driving condition in which the amplitude of the filtered reference signal r(i) takes a maximum value is regarded as a standard driving condition. The driving condition in which the amplitude of the filtered reference signal r(i) takes a maximum value is satisfied, for example, when movable body 102 drives a road with an extremely rough surface. The standard filtered reference signal $r_{REF}$(i) may be determined by measuring the filtered reference signal r(i) by an experiment, such as an actual driving experiment or a vibration experiment of movable body 102 in the standard driving condition. The standard filtered reference signal $r_{REF}$(i) may be determined by a simulation, such as CAE. The standard representative input value $d_{REF}$ is given as a constant based on the standard filtered reference signal $r_{REF}$(i). For example, the standard representative input value $d_{REF}$ can be defined as a maximum value of the standard filtered reference signal $r_{REF}$(i). Formula (13) defines a standard filtered reference signal $R_{REF}$ that is a vector with $N_l$ rows and one column composed of $N_l$ standard filtered reference signals $r_{REF}$(i) from the l-th step that is a certain time in the standard driving condition to the past by ($N_l$−1) steps.

$$R_{REF}=[r_{REF}(l),r_{REF}(l-1), \ldots ,r_{REF}(1-(N_l-1))]^T \quad (13)$$

The standard representative input value $d_{REF}$ may be given as a constant, for example, by an effective value expressed by formula (14) or a square of an average expressed by formula (15) based on the standard filtered reference signal $R_{REF}$ expressed by formula (13).

$$d_{REF} = \left( \frac{1}{N_l} \sum_{l=0}^{N_l-1} (r_{REF}(l))^2 \right)^{\frac{1}{2}} \tag{14}$$

$$d_{REF} = \left( \frac{1}{N_l} \sum_{l=0}^{N_l-1} |r_{REF}(l)| \right)^2 \tag{15}$$

The standard step-size parameter $\mu_{REF}$ can be determined previously by an experiment or a simulation in the standard driving condition that determines the standard representative input value $d_{REF}$. For example, in the case that the standard step-size parameter $\mu_{REF}$ is determined based on formula (12), the standard step-size parameter $\mu_{REF}$ is expressed by formula (16) with the maximum eigenvalue $\lambda_{REF,MAX}$ of the autocorrelation matrix of the standard filtered reference signal $R_{REF}$.

$$\mu_{REF} = \frac{2}{\lambda_{REF,MAX}} \tag{16}$$

Next, an operation of determining the step-size parameter μ(n) at the current n-th step will be described. The representative input value d(n) is calculated from the filtered reference signal $R_m(n)$ expressed by formula (17). The filtered reference signal $R_m(n)$ is a vector with $N_m$ rows and one column from the current n-th step to the past by $(N_m-1)$ steps.

$$R_m(n)=[r(n),r(n-1), \ldots ,r(n-(N_m-1))]^T \tag{17}$$

The number $N_m$ of steps is consistent with the number $N_l$ of steps of the standard filtered reference signals $R_{REF}$ although both numbers may be different from each other. The representative input value d(n) is defined as a parameter corresponding to the standard representative input value $d_{REF}$. In the case that the standard representative input value $d_{REF}$ is expressed by formula (14), the representative input value d(n) is determined by formula (18). In the case that the standard representative input value $d_{REF}$ is defined by formula (15), the representative input value d(n) is determined by formula (19).

$$d(n) = \left( \frac{1}{N_m} \sum_{m=0}^{N_m-1} (r(n-m))^2 \right)^{\frac{1}{2}} \tag{18}$$

$$d(n) = \left( \frac{1}{N_m} \sum_{m=0}^{N_m-1} |r(n-m)| \right)^2 \tag{19}$$

The step-size parameter μ(n) at the current n-th step is determined by formula (20) by dividing the standard step-size parameter $\mu_{REF}$ by a ratio of the representative input value d(n) to the standard representative input value $d_{REF}$.

$$\mu(n) = \mu_{REF} \cdot \frac{1}{\frac{d(n)}{d_{REF}}} = \mu_{REF} \cdot \frac{d_{REF}}{d(n)} \tag{20}$$

The μ-adjustment unit 8 thus determines the step-size parameter μ(i), and allows active noise reduction device 101 to operate stably while the filter coefficient W(i) of ADF 5 does not diverge even when the reference signal x(i) is large. Furthermore, even when the reference signal x(i) is small, the converging speed of the filter coefficient W(i) is high, and allows active noise reduction device 101 to effectively reduce noise N0. In an actual operation, for example, in the case that the standard representative input value $d_{REF}$ is expressed by formula (15) and the representative input value d(n) is expressed by formula (19), μ-adjustment unit 8 can reduce an arithmetic calculation amount by storing time-invariant constants together as a constant α expressed by formula (21) and formula (22).

$$\mu(n) = \mu_{REF} \cdot \frac{\left( \frac{1}{N_l} \sum_{l=0}^{N_l} |r_{REF}(l)| \right)^2}{\left( \frac{1}{N_m} \sum_{m=0}^{N_m-1} |r(n-m)| \right)^2} = \frac{N_m^2 \cdot \mu_{REF} \cdot d_{REF}}{\left( \sum_{k=m}^{N_m-1} |r(n-m)| \right)^2} = \frac{\alpha}{\left( \sum_{m=0}^{N_m-1} |r(n-m)| \right)^2} \tag{21}$$

$$\alpha = N_m^2 \cdot \mu_{REF} \cdot d_{REF} \tag{22}$$

In a driving condition that noise N0 changes a little, the step-size parameter μ(n) is updated at predetermined intervals without updating the step-size parameter μ(n) every step, thus reducing an arithmetic calculation load. In addition, μ-adjustment unit 8 may store a combination data table of plural representative input values d(i) and plural step-size parameters μ(i) calculated for each of the representative input values d(i) based on formula (20). The μ-adjustment unit 8 can adjust the step-size parameter μ(n) in a short time by reading, from the data table, a value of the step-size parameter μ(n) according to a value of the representative input value d(n). When a change in the driving condition is slower than the sampling period $T_s$ of active noise reduction device 101, μ-adjustment unit 8 may determine the step-size parameter μ(n) at the current n-th step using the filtered reference signal $R_m(n-\beta)$ before the current time instead of the filtered reference signal $R_m(n)$ at the current time (where β is a positive integer).

Figure 19:
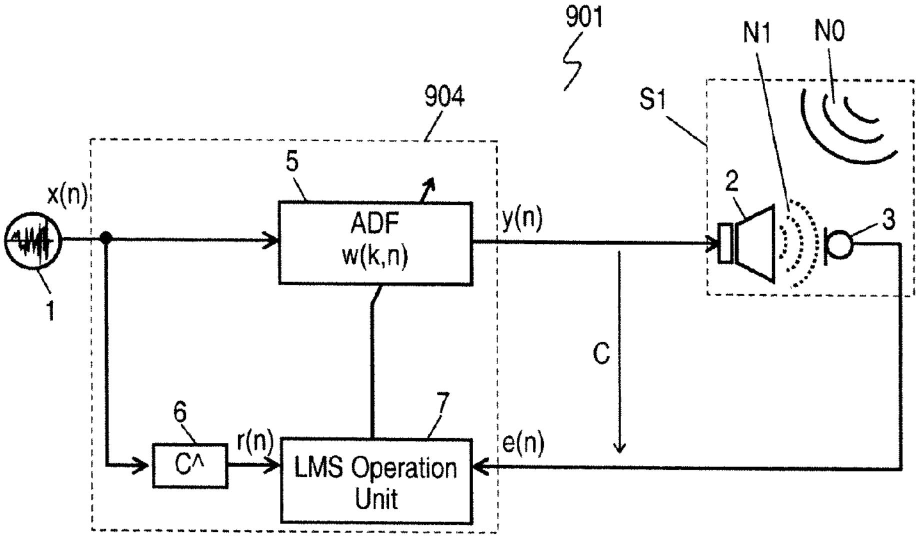
Fig. 19 PRIOR ART
FIG. 19 is a block diagram of a conventional active noise reduction device.

In the conventional active noise reduction device illustrated in FIG. 19, when a noise frequently changes in accordance with the driving condition, it is necessary to adapt a filter coefficient of the ADF quickly in order to output an optimal secondary noise that cancels the noise. However, when the step-size parameter is large, the adaptive filter easily diverges. By a method of calculating the step-size parameter in accordance with a residual or an amount of convergence, when a reference signal is small, the filter coefficient is updated too slowly, thus declining an effect of reducing the noise.

FIGS. 3 to 7 show a simulation result of converging characteristics of the filter coefficient W(i) of ADF 5 of an active noise reduction device with respect to an amplitude value of various reference signals x(i). In each of FIGS. 3 to

Figure 3:
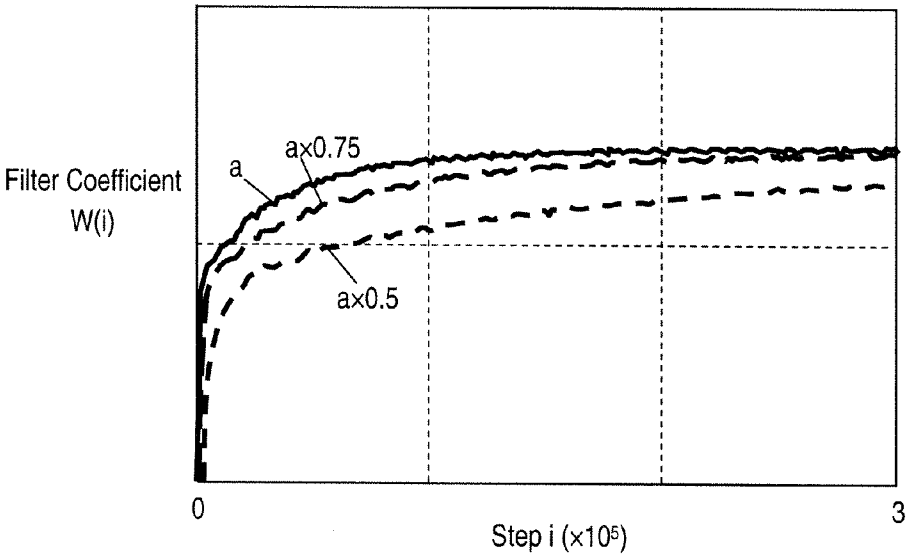
FIG. 3 shows convergence characteristics of a filter coefficient of a comparative example of an active noise reduction device.
Figure 4:
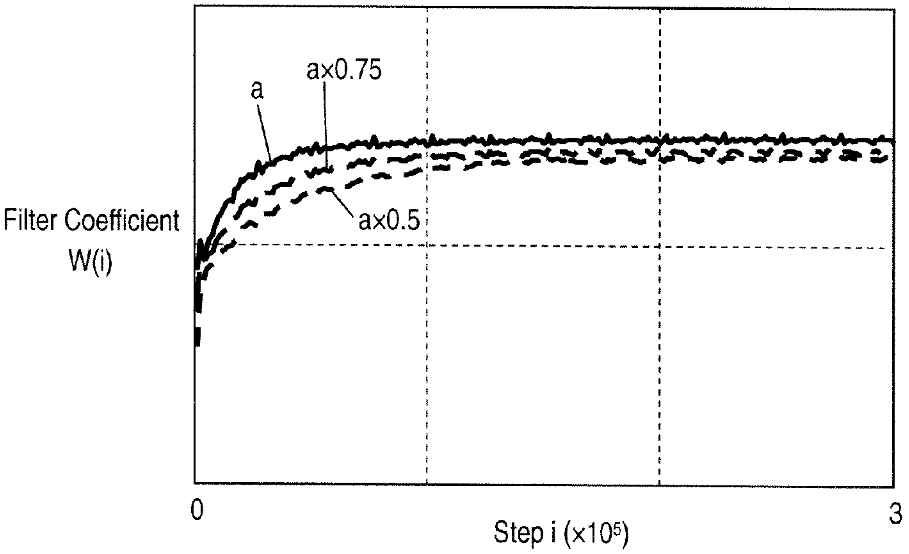
FIG. 4 shows convergence characteristics of a filter coefficient of another comparative example of an active noise reduction device.
Figure 5:
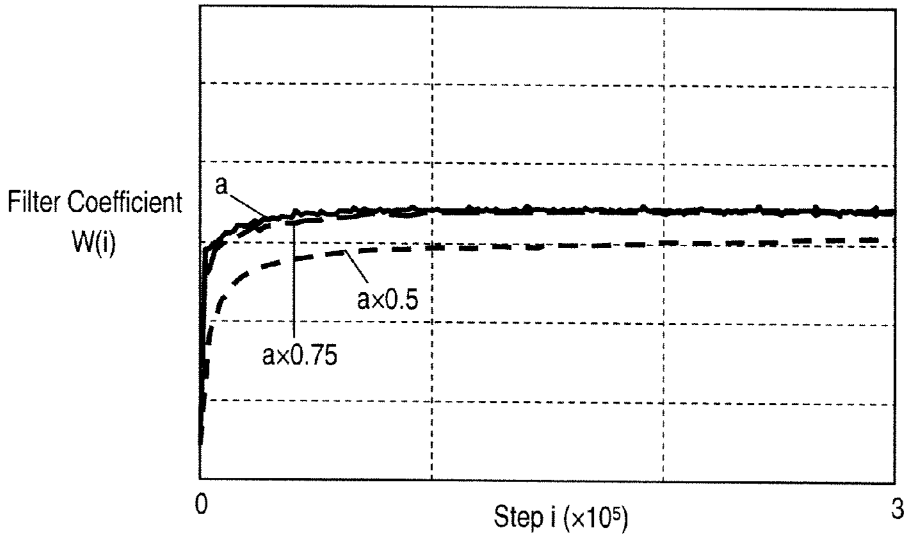
FIG. 5 shows convergence characteristics of a filter coefficient of still another comparative example of an active noise reduction device.

7, the horizontal axis represents a step, and the vertical axis represents a logarithmic representation of a mean square value of the filter coefficient W(i)=w(k,i) at each step. FIGS. 3 to 6 show the converging characteristics of the filter coefficient W(i) when the amplitude of the reference signals x(i) are a, a×0.75, and a×0.5, respectively. FIG. 3 illustrates the converging characteristics of the filter coefficient W(i) of a comparative example of an active noise reduction device that utilizes a normal LMS algorithm with the step-size parameter μ being a constant value. FIG. 4 illustrates the converging characteristics of the filter coefficient W(i) of another comparative example of an active noise reduction device that utilizes a normalized LMS (NLMS) algorithm. FIG. 5 illustrates the convergence characteristics of the filter coefficient W(i) of still another comparative example of an active noise reduction device that utilizes a robust variable step size (RVSS) algorithm described in PTL 3. Both of the comparative examples of the active noise reduction devices shown in FIGS. 4 and 5 are active noise reduction devices that utilize the algorithms for the purpose of adaptive speed improvement.

Figure 6:
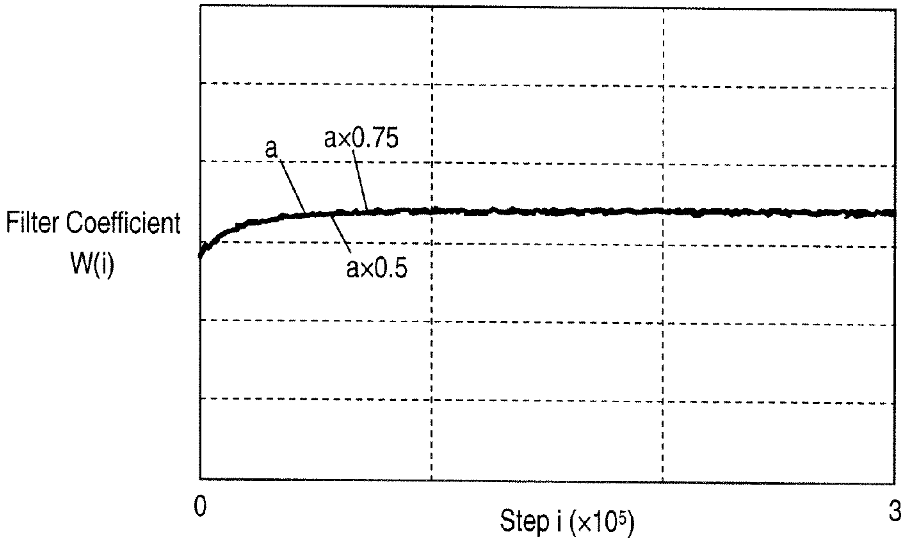
FIG. 6 shows convergence characteristics of a filter coefficient of the active noise reduction device according to Embodiment 1.

The NLMS algorithm illustrated in FIG. 4 and the RVSS algorithm illustrated in FIG. 5 suppresses decline of the converging speed for small amplitude of the reference signal x(i) more than the LMS algorithm illustrated in FIG. 3. The converging characteristics of active noise reduction device 101 according to Embodiment illustrated in FIG. 6 is further superior to the converging characteristics illustrated in FIGS. 4 and 5. The decline of the converging speed is not observed in FIG. 6 when the amplitude of the reference signal x(i) is small.

Figure 7:
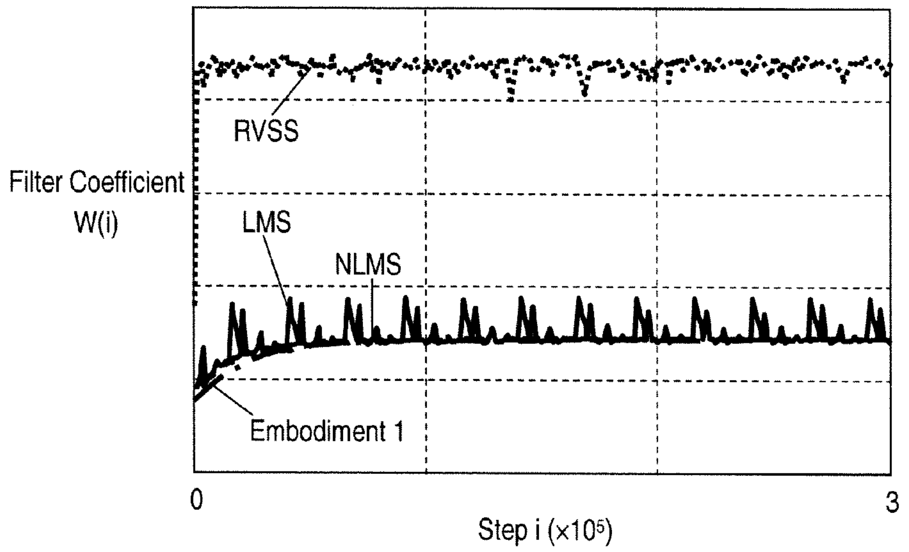
FIG. 7 shows convergence characteristics of the filter coefficient of the active noise reduction device according to Embodiment 1.

FIG. 7 illustrates a simulation result of the converging characteristic of the filter coefficient W(i) of ADF 5 in each algorithm when the reference signal x(i) has the amplitude of a×2. A value between scale lines in the vertical axis of FIG. 7 is identical to a value of each of FIGS. 3 to 6. As illustrated in FIGS. 3 to 7, the active noise reduction devices of the comparative examples utilizing the LMS algorithm, the NLMS algorithm, and the RVSS algorithm prevent the filter coefficients W(i) from growing stably. However, active noise reduction device 101 according to Embodiment 1 exhibits a converging characteristic with the stable filter coefficient even if the amplitude of the reference signal x(i) becomes large.

Active noise reduction device 101 according to Embodiment 1 thus provides stability of ADF 5 and the high converging speed.

By the method described above, μ-adjustment unit 8 calculates the step-size parameter μ(n) by formula (20) based on the standard representative input value $\mu_{REF}$ and the standard step-size parameter $\mu_{REF}$ in the standard driving condition, and the representative input value d(n) showing the current driving state. However, it takes time to set the standard step-size parameter $\mu_{REF}$ that is optimal to noise N0 according to the driving condition that changes depending on movable body 102. Since signal-processing device 4 typically includes register 4R that has a format of a finite bit number, an arithmetic calculation precision is limited. This limitation may cause the step-size parameter μ(n) to become zero when the filtered reference signal $R_m(n)$ is significantly large. This causes a fault that the filter coefficient W(n) is not updated and noise N0 is not reduced although noise N0 is large. On the other hand, when the filtered reference signal $R_m(n)$ is extremely small, the representative input value d(n) contained in a denominator of formula (20) approaches zero. Accordingly, the step-size parameter μ(n) becomes excessively large, and causing the filter coefficient W(n) to converging unstably.

In order to prevent the above problem, active noise reduction device 101 according to Embodiment 1 determines an upper limit value and a lower limit value of a calculation result of each of the representative input value d(i) and a calculation result of the step-size parameter μ(i). Values of these parameters are digital values expressed in register 4R of signal-processing device 4 that has a format of a finite bit number. Particularly for a fixed decimal mode, at least one value of the upper limit value and the lower limit value of each value can be determined by changing the number of bits of a decimal part. For example, if 16-bit register 4R for storing an arithmetic calculation result of the representative input value d(i) is used in a Q12 format, an upper limit value of the representative input value d(i) is 7.999755859375 ($=2^3-2^{-12}$), and a resolution is 0.000244140625 ($=2^{-12}$). Thus, a value by which the standard step-size parameter $\mu_{REF}$ is multiplied in formula (20) is limited to be within a range from 0.125 to 4096. If 16-bit register 4R for storing the step-size parameter μ(i) is used in a Q10 format, an upper limit value of the representative input value d(i) is 127.99609375 ($=2^5-2^{-10}$). Thus, the step-size parameter μ(i) is limited to be within a range from 0.125 to 127.99609375.

By determining at least one value of the upper limit value and the lower limit value for the step-size parameter μ(i) by the above technique, the step-size parameter μ(i) does not becomes zero or an extremely large value even if the amplitude of the reference signal x(i) output from reference signal source 1 has any value. Accordingly, active noise reduction device 101 can operate stably and normally.

According to Embodiment 1, the driving condition with the maximum amplitude of the filtered reference signal r(i) is regarded as the standard driving condition. However, the standard driving condition is not limited to the above-described driving condition. In this case, it is possible to ensure stability of the adaptive operation by determining the upper limit value of the step-size parameter μ(i).

Even if the standard filtered reference signal $r_{REF}(i)$ is not obtained previously by an experiment or a simulation, the filtered reference signal r(l) (where l is a small integer) when movable body 102 starts driving may be used as the standard filtered reference signal $r_{REF}(i)$. In active noise reduction device 101, the standard representative input value $d_{REF}$ and the standard step-size parameter $\mu_{REF}$ can be updated when a particular condition, e.g. that the amplitude of the filtered reference signal r(i) exceeds a maximum value of the amplitude of the standard filtered reference signal $r_{REF}(i)$ in the standard driving condition during operation, is satisfied.

In active noise reduction device 101 according to Embodiment 1, ADF 5 is an adaptive filter that utilizes the FxLMS algorithm. However, a similar effect is obtained even if ADF 5 utilizes an adaptive algorithm, such as a projection algorithm, a Simple Hyperstable Adaptive Recursive Filter (SHARF) algorithm, or a frequency-domain LMS algorithm, using a step-size parameter.

Active noise reduction device 101 according to Embodiment 1 can reduce noise N0 not only in movable body 102 but also in an unmovable device that has space S1 in which noise N0 exists.

The standard representative input value $d_{REF}$ may be based not only on the standard filtered reference signal $r_{REF}(i)$ as shown in formula (14) and formula (15) but also on $N_l$ standard error signals $e_{REF}(i)$ in the standard driving condition. For example, the standard representative input value $d_{REF}$ may be based on a product of the standard filtered reference signal $r_{REF}(i)$ and the standard error signal $e_{REF}(i)$ expressed by formula (23), or on an effective value of the standard error signal $e_{REF}(i)$ expressed by formula (24).

$$d_{REF} = \left(\frac{1}{N_l}\sum_{l=0}^{N_l-1}(e_{REF}(l)\cdot r_{REF}(l))\right)^{\frac{1}{2}} \quad (23)$$

$$d_{REF} = \left(\frac{1}{N_l}\sum_{l=0}^{N_l-1}(e_{REF}(l))^2\right)^{\frac{1}{2}} \quad (24)$$

Since the representative input value d(i) is defined in a form corresponding to the standard representative input value $d_{REF}$, the representative input value d(n) at the n-th step is determined by formula (25) when the standard representative input value $d_{REF}$ is expressed by formula (23). Representative input value d(n) at the n-th step is determined by formula (26) when the standard representative input value $d_{REF}$ is expressed by formula (24).

$$d(n) = \left(\frac{1}{N_m}\sum_{m=0}^{N_m-1}(e(n-m)\cdot r(n-m))\right)^{\frac{1}{2}} \quad (25)$$

$$d(n) = \left(\frac{1}{N_m}\sum_{m=0}^{N_m-1}(e(n-m))^2\right)^{\frac{1}{2}} \quad (26)$$

Figure 8:
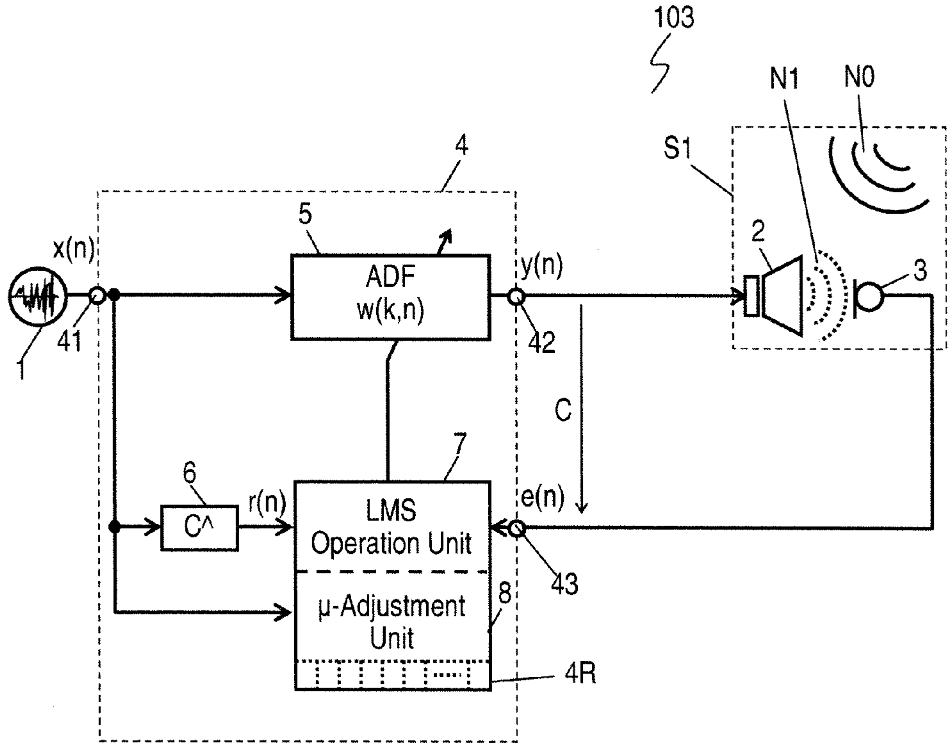
FIG. 8 is a block diagram of another active noise reduction device according to Embodiment 1.

FIG. 8 is a block diagram of another active noise reduction device 103 according to Embodiment 1. In FIG. 8, components identical to those of active noise reduction device 101 shown in FIG. 1 are denoted by the same reference numerals. When the filter coefficient c^(i) of Chat unit 6 is a time-invariant constant c^, the filtered reference signal r(i) has a fixed relationship with the reference signal x(i) as expressed by formula (7). Accordingly, the step-size parameter μ(i) may be calculated by using the standard reference signal $x_{REF}(i)$ and the reference signal x(i) instead of the standard filtered reference signal $r_{REF}(i)$ and the filtered reference signal r(i).

In active noise reduction device 103 illustrated in FIG. 8, μ-adjustment unit 8 calculates the step-size parameter VD by using the standard reference signal $x_{REF}(i)$ and the reference signal x(i) instead of the standard filtered reference signal $r_{REF}(i)$ and the filtered reference signal r(i). That is, instead of the filtered reference signal $R_m(n)$ expressed by formula (17), formula (27) defines the reference signal $X_m(n)$ that is a vector with $N_m$ rows and one column composed of $N_m$ reference signals x(i) from the current n-th step to a past by $(N_m-1)$ steps.

$$X_m(n)=[x(n),x(n-1), \ldots ,x(n-(N_m-1))]^T \quad (27)$$

Instead of the standard filtered reference signal $R_{REF}$ with $N_l$ rows and one column expressed by formula (13) that is the standard filtered reference signal $r_{REF}(i)$, formula (28) defines the standard reference signal $X_{REF}$ that is a vector with $N_l$ rows and one column composed of $N_l$ standard reference signals $x_{REF}(i)$ from the l-th step that is a certain time in the standard driving condition to a past by $(N_l-1)$ steps.

$$X_{REF}=[x_{REF}(l),x_{REF}(l-1), \ldots ,x_{REF}(1-(N_l-1))]^T \quad (28)$$

The standard representative input value $d_{REF}$ may be given as a constant, for example, by an effective value expressed by formula (29) based on the standard reference signal $X_{REF}$ expressed by formula (28).

$$d_{REF} = \left(\frac{1}{N_1}\sum_{1=0}^{N_1-1}(x_{REF}(1))^2\right)^{\frac{1}{2}} \quad (29)$$

The representative input value d(i) is defined as a parameter corresponding to the standard representative input value $d_{REF}$. In the case that the standard representative input value $d_{REF}$ is expressed by formula (29), the representative input value d(i) is calculated from the reference signal $X_m(n)$ by formula (30) similarly to the representative input value d(n) expressed by formula (18).

$$d(n) = \left(\frac{1}{N_m}\sum_{m=0}^{N_m-1}(x_m(n-m))^2\right)^{\frac{1}{2}} \quad (30)$$

Similarly to active noise reduction device 101 illustrated in FIG. 1, μ-adjustment unit 8 of active noise reduction device 103 determines the step-size parameter μ(n) at the n-th step by formula (20) using the standard representative input value $d_{REF}$ expressed by formula (29) and the representative input value d(n) expressed by formula (30). Active noise reduction device 103 has effects similar to those of active noise reduction device 101 illustrated in FIG. 1.

As described above, active noise reduction device 101 (103) is configured to be used together with reference signal source 1, secondary noise source 2, and error signal source 3. Reference signal source 1 outputs the reference signal x(i) that has a correlation with the noise. Secondary noise source 2 generates secondary noise N1 corresponding to the secondary noise signal y(i). Error signal source 3 outputs the error signal e(i) corresponding to the residual sound caused by interference between secondary noise N1 and noise N0. Active noise reduction device 101 (103) includes signal-processing device 4 has input port 41 (a first input port) for receiving the reference signal x(i), input port 43 (a second input port) for receiving the error signal e(i), and output port 42 for outputting the secondary noise signal y(i). Signal-processing device 4 includes ADF 5, Chat unit 6, LMS operation unit 7, and μ-adjustment unit 8. ADF 5 outputs the secondary noise signal y(i) in accordance with the reference signal x(i). Chat unit 6 corrects the reference signal x(i) using a simulated acoustic transfer characteristic that simulates an acoustic transfer characteristic from output port 42 to input port 43, and outputs the filtered reference signal r(i). LMS operation unit 7 updates the filter coefficients w(k,i) of ADF 5 by using the error signal e(i), the filtered reference signal r(i), and the step-size parameter μ(i). The μ-adjustment unit 8 determines the step-size parameter μ(i). The μ-adjustment unit 8 is operable to calculate the representative input value d(i) corresponding to the amplitude of at least one signal of the reference signal x(i), the filtered reference signal r(i), and the error signal e(i). The μ-adjustment unit 8 is operable to store the standard representative input value $d_{REF}$ and the predetermined standard step-size parameter $\mu_{REF}$. The standard representative input value $d_{REF}$ is the representative input value d(i) when the amplitude of the at least one signal of the reference signal x(i), the filtered reference signal r(i), and the error signal e(i) is predetermined amplitude. The predetermined standard step-size parameter $\mu_{REF}$ is a value of the step-size parameter VD to which the filter coefficients w(k,i) converge when the representative input value d(i) is the standard representative input value $d_{REF}$. The μ-adjustment unit 8 is operable to calculate the step-size parameter μ(i) by multiplying the standard step-size parameter $\mu_{REF}$ by a ratio of the standard representative input value $d_{REF}$ to the representative input value d(i). Active noise reduction device 101 (103) reduces noise N0 by the operations described above.

The standard step-size parameter $\mu_{REF}$ may take a maximum value of the step-size parameter μ(i) to which the filter coefficients w(k,i) converge when the representative input value d(i) is the standard representative input value $d_{REF}$.

The standard representative input value $d_{REF}$ may correspond to a maximum value of the amplitude of the at least one signal of the reference signal x(i), the filtered reference signal r(i), and the error signal e(i).

At least one value of an upper limit value and a lower limit value of a coefficient by which the standard step-size parameter $\mu_{REF}$ is multiplied may be determined. This coefficient may be a digital value expressed in register 4R of signal-processing device 4 that has a fixed-point format. In this case, μ-adjustment unit 8 sets the at least one value of the upper limit value and lower limit value of this coefficient by changing a decimal point position of this coefficient.

Active noise reduction device 101 (103) is configured to be mounted in movable body 102 that has space S1. Noise N0 is generated in space S1, and secondary noise source 2 generates secondary noise N1 in space S1. The above-described residual sound is generated in space S1.

Exemplary Embodiment 2

Figure 9:
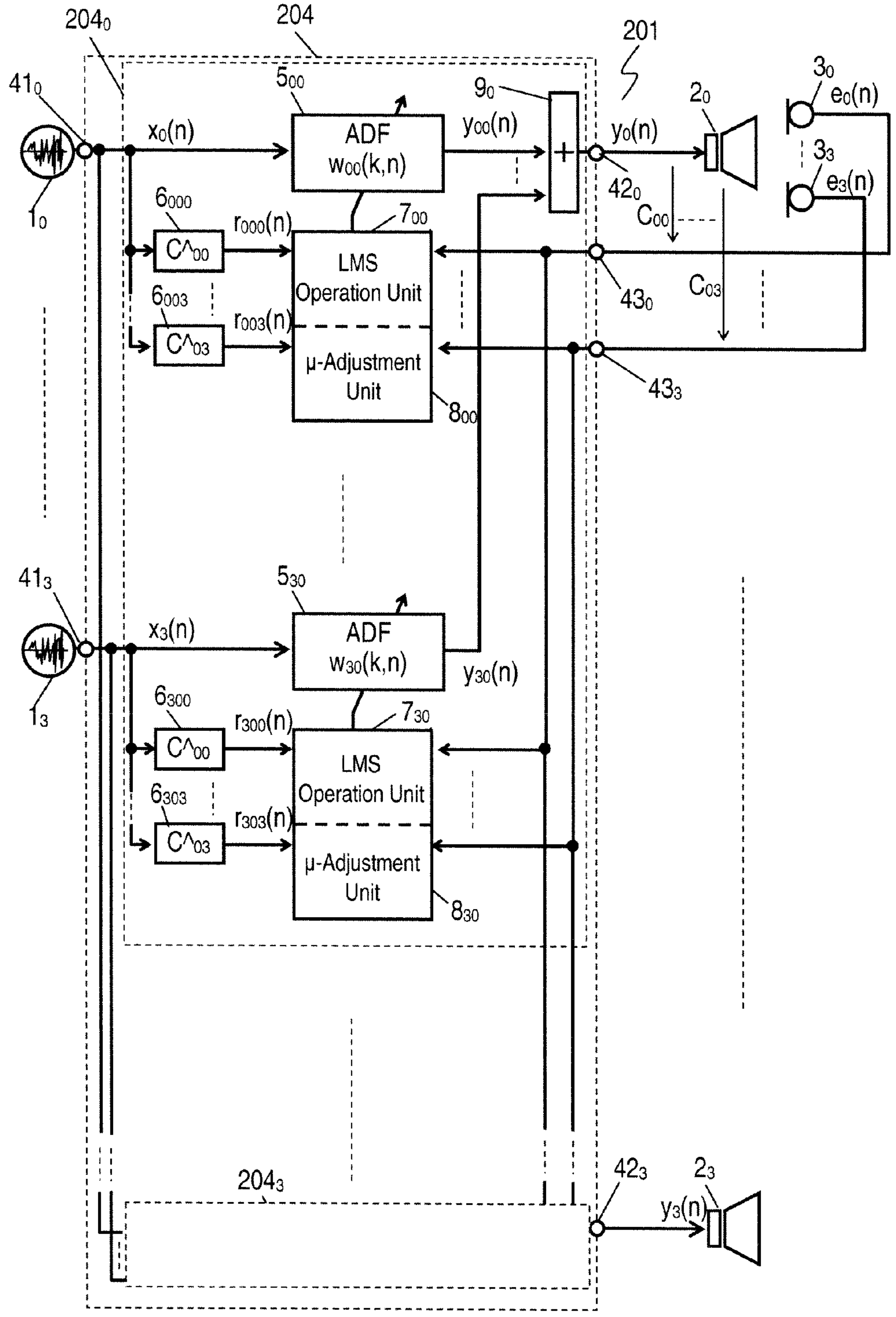
FIG. 9 is a block diagram of an active noise reduction device according to Exemplary Embodiment 2 of the present invention.
Figure 10:
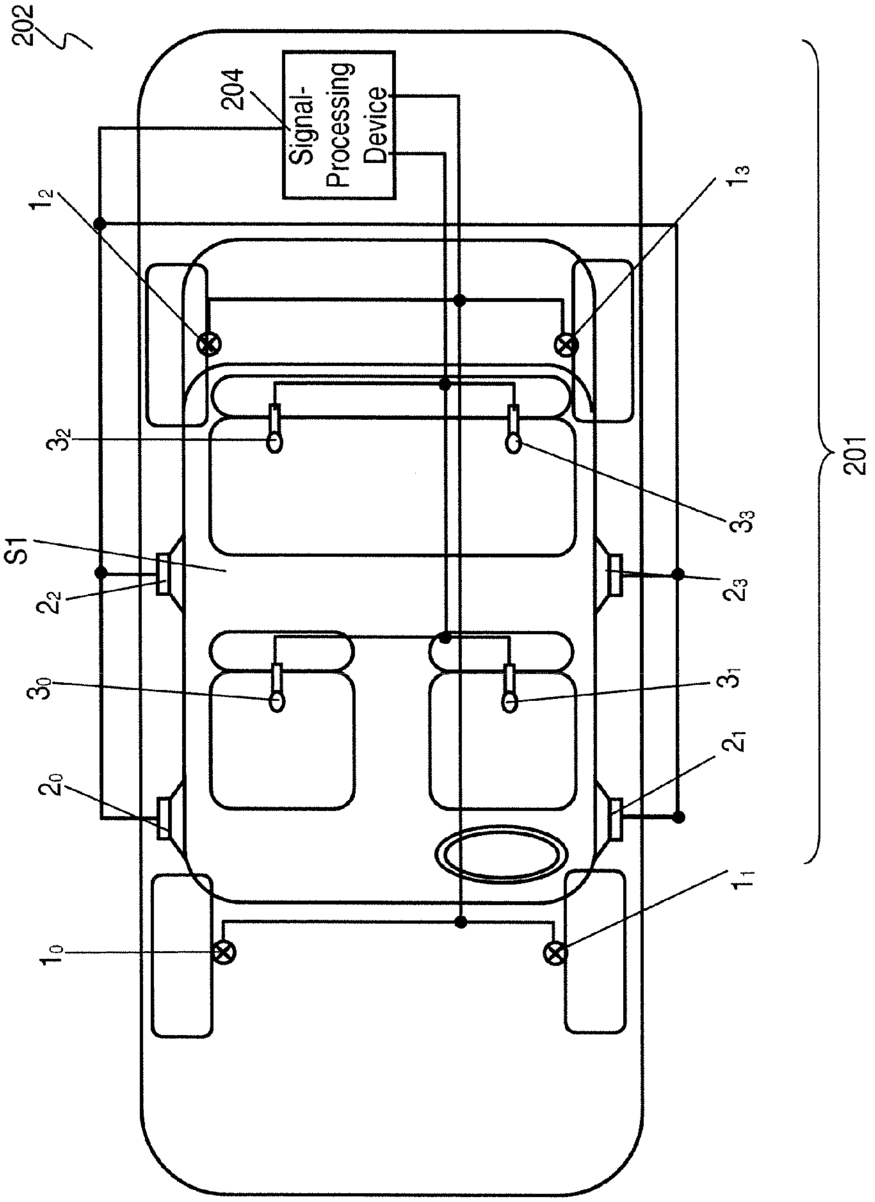
FIG. 10 is a schematic diagram of a movable body having the active noise reduction device according to Embodiment 2 mounted thereto.

FIG. 9 is a block diagram of active noise reduction device 201 according to Exemplary Embodiment 2 of the present invention. FIG. 10 is a schematic diagram of movable body 202 having active noise reduction device 201 mounted thereto. In FIGS. 9 and 10, components identical to those of active noise reduction device 101 and movable body 102 according to Embodiment 1 illustrated in FIGS. 1 and 2 are denoted by the same reference numerals.

Active noise reduction device 101 according to the first exemplary embodiment includes one reference signal source 1, one secondary noise source 2, one error signal source 3, and signal-processing device 4. Active noise reduction device 201 can reduce a noise in space S1 by means of signal-processing device 204, at least one reference signal source $\mathbf{1}_\xi$, at least one secondary noise source $\mathbf{2}_\eta$, and at least one error signal source $\mathbf{3}_\zeta$.

Active noise reduction device 201 according to Embodiment 2 has a system configuration of a case (4,4,4) that includes four reference signal sources $\mathbf{1}_0$ to $\mathbf{1}_3$, four secondary noise sources $\mathbf{2}_0$ to $\mathbf{2}_3$, and four error signal sources $\mathbf{3}_0$ to $3_3$. In Embodiment 2, the system of the case (4,4,4) will be described. However, each of the numbers of reference signal sources $\mathbf{1}_\xi$, secondary noise sources $\mathbf{2}_\eta$, and error signal sources $\mathbf{3}_\zeta$ may not necessarily be four, but may have a configuration of a case (ξ, η, ζ) with the numbers different from each other.

In description of Embodiment 2, an identical subscript is given as a symbol that denotes an identical number, such as the number "ξ" of reference signals, the number "η" of secondary noise sources, and the number "ζ" of error signal sources. A component having a plurality of elements, such as Chat unit $\mathbf{6}_{0\eta\zeta}$, is denoted with plural subscripts. For example, the reference numerals "$\mathbf{6}_{0\eta\zeta}$" denotes that each of η secondary noise sources is associated with ζ error signal sources. The number of Chat units $\mathbf{6}_{0\eta\zeta}$ is η×ζ.

Signal-processing device 204 includes plural input ports $\mathbf{41}_\xi$ for receiving reference signals $x_\xi(i)$ output from reference signal sources $\mathbf{1}_\xi$, plural input ports $\mathbf{43}_\zeta$ for receiving error signals $e_\zeta(i)$ output from error signal sources $\mathbf{3}_\zeta$, plural output ports $\mathbf{42}_\eta$ for outputting secondary noise signals $y_\eta(i)$ to secondary noise sources $\mathbf{2}_\eta$, and plural signal processors $\mathbf{204}_\eta$ for calculating the secondary noise signals $y_\eta(i)$. Although signals are output and input through plural input ports $\mathbf{41}_\xi$ and $\mathbf{43}_\zeta$ and output port $\mathbf{42}_\eta$, the numbers of these ports may not be identical to the numbers of reference signal sources $\mathbf{1}_\xi$, error signal sources $\mathbf{3}_\zeta$, and secondary noise sources $\mathbf{2}_\eta$. All the signals may be input into a single input port, and all the signals may be output from a single output port. Signal-processing device 204 operates at a sampling period $T_s$. When a system of the case (ξ,η,ζ) fails to finish processing within the sampling period $T_s$ with one signal-processing device 204, the system may include plural signal-processing devices.

Each of signal processors $\mathbf{204}_\eta$ includes plural ADFs $\mathbf{5}_{\xi\eta}$, plural Chat units $\mathbf{6}_{\xi\eta\zeta}$, plural LMS operation units $\mathbf{7}_{\xi\eta}$, plural μ-adjustment units $\mathbf{8}_{\xi\eta}$, and signal adder $\mathbf{9}_\eta$ for outputting a signal obtained by summing plural signals.

An operation of signal processor $\mathbf{204}_\eta$ will be described below. Signal processor $\mathbf{204}_0$ that outputs secondary noise signal $y_0(i)$ for driving secondary noise source $\mathbf{2}_0$ includes four sets of ADFs $\mathbf{5}_{00}$ to $\mathbf{5}_{30}$, LMS operation units $\mathbf{7}_{00}$ to $\mathbf{7}_{30}$, and μ-adjustment units $\mathbf{8}_{00}$ to $\mathbf{8}_{30}$, the number, four, is identical to the number of reference signal sources $\mathbf{1}_0$ to $\mathbf{1}_3$. Signal processor $\mathbf{204}_0$ also includes signal adder $\mathbf{9}_0$ and sixteen Chat units $\mathbf{6}_{000}$ to $\mathbf{6}_{303}$. The number, sixteen, is a product of the number of reference signal sources $\mathbf{1}_0$ to $\mathbf{1}_3$ and the number of error signal sources $\mathbf{3}_0$ to $\mathbf{3}_3$.

First, an operation of a set of ADF $\mathbf{5}_{00}$, LMS operation unit $\mathbf{7}_{00}$, μ-adjustment unit $\mathbf{8}_{00}$, and Chat units $\mathbf{6}_{00\zeta}$ regarding reference signal source $\mathbf{1}_0$ will be described. ADF $\mathbf{5}_{00}$ determines the secondary noise signal $y_{00}(n)$ by performing a filtering operation on a filter coefficient $w_{00}(k,n)$ and the reference signal $x_0(i)$ by formula (31).

$$y_{00}(n)=\sum_{k=0}^{N-1} w_{00}(k,n)\cdot x_0(n-k) \tag{31}$$

Similarly to a filter coefficient C^(i) that simulates an acoustic transfer characteristic C(i) of a path between output port 42 and input port 43 for an error signal e(i) according to Embodiment 1, Chat units $\mathbf{6}_{0\eta\zeta}$ have filter coefficients $C\hat{}_{\eta\zeta}(i)$ that simulate acoustic transfer characteristics $C_{\eta\zeta}(i)$ between output ports $\mathbf{42}_\eta$ and input ports $\mathbf{43}_\zeta$ for the error signals $e_\zeta(i)$ according to Embodiment 2, respectively. According to Embodiment 2, Chat units $\mathbf{6}_{\xi\eta\zeta}$ have time-invariant filter coefficients $C\hat{}_{\eta\zeta}$. Signal processor $\mathbf{204}_0$ has four Chat units $\mathbf{6}_{000}$ to $\mathbf{6}_{003}$ corresponding to the number of error signals $e_\zeta(i)$. The filter coefficients $C\hat{}_{00}$ to $C\hat{}_{03}$ of Chat units $\mathbf{6}_{000}$ to $\mathbf{6}_{003}$ are expressed by formula (32).

$$\hat{C_{00}} = [c\hat{_{00}}(0), c\hat{_{00}}(1), \ldots , c\hat{_{00}}(N_c - 1)]^T \quad (32)$$
$$\vdots$$
$$\hat{C_{0\zeta}} = [c\hat{_{0\zeta}}(0), c\hat{_{0\zeta}}(1), \ldots , c\hat{_{0\zeta}}(N_c - 1)]^T$$
$$\vdots$$
$$\hat{C_{03}} = [c\hat{_{03}}(0), c\hat{_{03}}(1), \ldots , c\hat{_{03}}(N_c - 1)]^T$$

Chat units $\mathbf{6}_{00\zeta}$ performs the filtering operation expressed by formula (33) on the filter coefficients $C\hat{}_{0\zeta}$ expressed by formula (32) and the reference signal $X_0$ (n) to output filtered reference signals $r_{00\zeta}(n)$.

$$r_{000}(n) = \hat{C_{00}}^T X_0(n) \quad (33)$$
$$\vdots$$
$$r_{00\zeta}(n) = \hat{C_{0\zeta}}^T X_0(n)$$
$$\vdots$$
$$r_{003}(n) = \hat{C_{03}}^T X_0(n)$$

The reference signal $X_0(n)$ is a vector expressed by formula (34) composed of $N_c$ reference signals $x_0(i)$ from the current n-th step to a past by $(N_c-1)$ steps.

$$X_0(n)=[x_0(n),x_0(n-1), \ldots ,x_0(n-(N_c-1))]^T \quad (34)$$

The μ-adjustment unit $\mathbf{8}_{00}$ outputs step-size parameters $\mu_{00\zeta}(n)$ at the current n-th step based on predetermined standard step-size parameters $\mu_{REF,00\zeta}$ that are step-size parameters used as standards previously determined and at least one signal of the reference signals $x_0(i)$, the filtered reference signals $r_{00\zeta}(i)$, and the error signals $e_\zeta(i)$.

LMS operation unit $\mathbf{7}_{00}$ updates a filter coefficient $W_{00}(n)$ of ADF $\mathbf{5}_{00}$ by formula (35) using the four filtered reference signals $R_{00\zeta}(n)$, four error signals $e_\zeta(n)$, and four step-size parameters $\mu_{00\zeta}(n)$ determined by formula (33).

$$W_{00}(n+1) = W_{00}(n) - \sum_{\zeta=0}^{3} \mu_{00\zeta}(n) \cdot e_\zeta(n) \cdot R_{00\zeta}(n) \quad (35)$$

Filtered reference signals $R_{00\zeta}(n)$ are composed of the filtered reference signals $r_{00\zeta}(i)$ obtained by filtering the reference signal $x_0(i)$ with simulated acoustic transfer characteristics $C\hat{}_{0\zeta}$ as expressed by formula (36).

$$R_{000}(n) = [r_{000}(n), r_{000}(n-1), \ldots , r_{000}(n-(N-1))]^T \quad (36)$$
$$\vdots$$
$$R_{00\zeta}(n) = [r_{00\zeta}(n), r_{00\zeta}(n-1), \ldots , r_{00\zeta}(n-(N-1))]^T$$
$$\vdots$$
$$R_{003}(n) = [r_{003}(n), r_{003}(n-1), \ldots , r_{003}(n-(N-1))]^T$$

The filter coefficient $W_{00}(n)$ of ADF $\mathbf{5}_{00}$ is expressed by formula (37).

$$W_{00}(n)=[w_{00}(0,n),w_{00}(1,n), \ldots ,w_{00}(N-1,n)]^T \quad (37)$$

According to formula (35), the filtered reference signals $R_{00\zeta}(n)$ and the error signals $e_\zeta(n)$ are degrees indicated by the step-size parameters $\mu_{00\zeta}(n)$, and contribute to the updating of the filter coefficient $W_{00}(n)$.

Next, an operation of determining the secondary noise signal $y_{00}(i)$ will be generalized for three sets of ADFs $\mathbf{5}_{10}$ to $\mathbf{5}_{30}$, LMS operation units $\mathbf{7}_{10}$ to $\mathbf{7}_{30}$, the μ-adjustment units $\mathbf{8}_{10}$ to $\mathbf{8}_{30}$, and Chat units $\mathbf{6}_{10\zeta}$ to $\mathbf{6}_{30\ \zeta}$ that determine the secondary noise signals $y_{10}(i)$ to $y_{30}(i)$ in accordance with the other three reference signals $x_1(i)$ to $x_3(i)$.

The current secondary noise signals $y_{\xi\eta}(n)$ determined when ADFs $\mathbf{5}_{\xi 0}$ perform the filtering operation on the reference signals $x_\xi(i)$ are provided by formula (38).

$$y_{\xi 0}(n) = \sum_{k=0}^{N-1} w_{\xi 0}(k, n) \cdot x_\xi(n-k) \quad (38)$$

Chat units $\mathbf{6}_{\xi 0\zeta}$ output the filtered reference signals $r_{\xi 0\zeta}(n)$ by performing an arithmetic calculation expressed by formula (40) on the filter coefficients $C\hat{}_{0\zeta}$ expressed by formula (32) and the reference signals $X_\xi(n)$ expressed by formula (39).

$$X_\xi(n)=[x_\xi(n),x_\xi(n-1), \ldots ,x_\xi(n-(N_c-1))]^T \quad (39)$$

$$r_{\xi 0\zeta}(n)=C\hat{}_{0\zeta}{}^T X_\xi(n) \quad (40)$$

The filtered reference signals $R_{\xi 0\zeta}(n)$ with N rows and one column composed of the filtered reference signals $r_{\xi 0\zeta}(i)$ are expressed by formula (41).

$$R_{\xi 0\zeta}(n)=[r_{\xi 0\zeta}(n),r_{\xi 0\zeta}(n-1), \ldots ,r_{\xi 0\zeta}(n-(N-1))]^T \quad (41)$$

The μ-adjustment units $\mathbf{8}_{\xi 0}$ output the current step-size parameters) $\mu_{\xi 0\zeta}(n)$ based on the standard step-size parameters $\mu_{REF,\xi 0\zeta}$ and at least one signal of the reference signals $x_\xi(i)$, the filtered reference signals $r_{\xi 0\zeta}(i)$, and the error signals $e_\zeta(i)$.

LMS operation units $\mathbf{7}_{\xi 0}$ update the filter coefficients $W_{\xi 0}(n)$ expressed by formula (42), as expressed as formula (43).

$$W_{\xi 0}(n) = [w_{\xi 0}(0, n), w_{\xi 0}(1, n), \ldots , w_{\xi 0}(N-1, n)]^T \quad (42)$$

$$W_{\xi 0}(n+1) = W_{\xi 0}(n) - \sum_{\zeta=0}^{3} \mu_{\xi 0\zeta}(n) \cdot e_\zeta(n) \cdot R_{\xi 0\zeta}(n) \quad (43)$$

Signal adder $\mathbf{9}_0$ sums four secondary noise signals $y_{00}(n)$ to $y_{30}(n)$ as expressed by formula (44) to generate the secondary noise signal $y_0(n)$ to be supplied to secondary noise source $\mathbf{2}_0$.

$$y_0(n) = \sum_{\xi=0}^{3} y_{\xi 0}(n) \quad (44)$$

Signal processors $\mathbf{204}_\eta$ that output the secondary noise signals $y_\eta(i)$ to secondary noise sources $\mathbf{2}_\eta$ including the other secondary noise sources $\mathbf{2}_1$ to $\mathbf{2}_3$ will be described by expanding the operation of signal processor $\mathbf{204}_0$.

ADFs $\mathbf{5}_{\xi\eta}$ determine the secondary noise signals $y_{\xi\eta}(n)$ at the current n-th step by performing the filtering operation, that is, a convolution operation expressed by formula (45) using the filter coefficients $w_{\xi\eta}(k,n)$ and the reference signals $x_\xi(i)$.

$$y_{\xi\eta}(n) = \sum_{k=0}^{N-1} w_{\xi n}(k, n) \cdot x_\xi(n-k) \tag{45}$$

Chat units $6_{\xi\eta\zeta}$ have the time-invariant filter coefficients $C\hat{}_{\eta\zeta}$ expressed by formula (46). The filter coefficients simulate the acoustic transfer characteristics $C_{\eta\zeta}(i)$ between output ports $\mathbf{42}_\eta$ and input ports $\mathbf{43}_\zeta$ for the error signals $e_\zeta(i)$.

$$C\hat{}=[c\hat{}_{\eta\zeta}(0), c\hat{}_{\eta\zeta}(1), \ldots, c\hat{}_{\eta\zeta}(N_c-1)]^T \tag{46}$$

According to Embodiment 2, since each of four secondary noise sources $\mathbf{2}_\eta$ has paths for four error signal sources $\mathbf{3}_\zeta$, Chat units $6_{\xi\eta\zeta}$ have sixteen filter coefficients.

Chat units $6_{\xi\eta\zeta}$ calculate the filtered reference signals $r_{\xi\eta\zeta}(n)$ by formula (47) from the filter coefficients $C\hat{}_{\eta\zeta}$ expressed by formula (46) and the reference signals $X_\xi(n)$ expressed by formula (39).

$$r_{\xi\eta\zeta}(n)=C\hat{}_{\eta\zeta}{}^T X_\xi(n) \tag{47}$$

The filtered reference signals $R_{\xi\eta\zeta}(n)$ with N rows and one column composed of the filtered reference signals $r_{\xi\eta\zeta}(i)$ are expressed by formula (48).

$$R_{\xi\eta\zeta}(n)=[r_{\xi\eta\zeta}(n), r_{\xi\eta\zeta}(n-1), \ldots, r_{\xi\eta\zeta}(n-(N-1))]^T \tag{48}$$

The μ-adjustment units $\mathbf{8}_{\xi\eta}$ output the current step-size parameters $\mu_{\xi\eta\zeta}(n)$ based on the standard step-size parameters $\mu_{REF,\xi\eta\zeta}$ and at least one signal of the reference signals $x_\xi(i)$, the filtered reference signals $r_{\xi\eta\zeta}(i)$, and the error signals $e_\zeta(i)$.

LMS operation units $\mathbf{7}_{\xi\eta}$ update the filter coefficients $W_{\xi\eta}(n)$ expressed by formula (49), as shown in formula (50).

$$W_{\xi\eta}(n) = [w_{\xi\eta}(0, n), w_{\xi\eta}(1, n), \ldots, w_{\xi\eta}(N-1, n)]^T \tag{49}$$

$$W_{\xi\eta}(n+1) = W_{\xi\eta}(n) - \sum_{\zeta=0}^{3} \mu_{\xi\eta\zeta}(n) \cdot e_\zeta(n) \cdot R_{\xi\eta\zeta}(n) \tag{50}$$

Signal adder $\mathbf{9}_\eta$ sums up the secondary noise signals $y_{\xi\eta}(n)$, as expressed by formula (51), to generate the secondary noise signal $y_\eta(n)$ to be supplied to secondary noise sources $\mathbf{2}_\eta$.

$$y_\eta(n) = \sum_{\xi=0}^{3} y_{\xi\eta}(n) \tag{51}$$

As described above, active noise reduction device 201 can determine the optimal secondary noise signal $y_\eta(n)$ that cancels noise N0 at positions of plural error signal sources $\mathbf{3}_\zeta$, and can reduce noise N0 in space S1 by updating the filter coefficients $W_{\xi\eta}(n)$ of ADFs $\mathbf{5}_{\xi\eta}$ for every sampling period $T_s$ based on formula (50).

Next, regarding an operation of calculating the step-size parameters $\mu_{\xi\zeta\eta}(n)$ at the current n-th step in μ-adjustment units $\mathbf{8}_{\xi\eta}$, an operation of μ-adjustment unit $\mathbf{8}_{00}$ of a system that outputs secondary noise signal $y_0(i)$ in accordance with the reference signal $x_0(i)$ and an error signal $e_0(i)$ sill be described similarly to the operation of signal processors $\mathbf{204}_\eta$, and generalized The μ-adjustment unit $\mathbf{8}_{00}$ stores standard step-size parameters $\mu_{REF,00\zeta}$ and standard representative input values $d_{REF,00\zeta}$ based on standard filtered reference signals $r_{REF,00\zeta}(i)$ that are filtered reference signals $r_{00\zeta}(i)$ in a driving condition used as a standard for movable body 202. The μ-adjustment unit $\mathbf{8}_{00}$ determines representative input values $d_{00\zeta}(n)$ corresponding to the standard representative input values $d_{REF,00\zeta}(n)$ based on the filtered reference signals $r_{00\zeta}(i)$.

The μ-adjustment unit $\mathbf{8}_{00}$ calculates the step-size parameters $\mu_{00\zeta}(n)$ from the stored standard representative input values $d_{REF,00\zeta}$, the standard step-size parameters $\mu_{REF,00\zeta}$, and the representative input values $d_{00\zeta}(n)$.

In Embodiment 2, similarly to Embodiment 1, an operation of determining the standard representative input values $d_{REF,00\zeta}$ and the standard step-size parameters $\mu_{REF,00\zeta}$ in a standard driving condition that amplitude of the filtered reference signals $r_{00\zeta}(i)$ takes a maximum value will be described below. Similarly to formula (13), the standard filtered reference signal $R_{REF,00\zeta}$ that is a vector with $N_l$ rows and one column composed of the standard filtered reference signals $r_{REF,00\zeta}(i)$ from the l-th step that is a certain time in the standard driving condition to the past by $(N_l-1)$ steps, as expressed by formula (52).

$$R_{REF,00\zeta}=[r_{REF,00\zeta}(l), r_{REF,00\zeta}(l-1), \ldots, r_{REF,00\zeta}(l-(N_l-1))]^T \tag{52}$$

The standard representative input values $d_{REF,00\zeta}$ can be given as constants, for example, by an effective value or a square of an average value expressed by formula (53) and formula (54), respectively, similarly to formula (14) and formula (15), based on the standard filtered reference signals $R_{REF,00\zeta}$ expressed by formula (52).

$$d_{REF,00\zeta} = \left(\frac{1}{N_1}\sum_{1=0}^{N_1-1}(r_{REF,00\zeta}(1))^2\right)^{\frac{1}{2}} \tag{53}$$

$$d_{REF,00\zeta} = \left(\frac{1}{N_1}\sum_{1=0}^{N_1-1}|r_{REF,00\zeta}(1)|^2\right)^2 \tag{54}$$

Four standard representative input values $d_{REF,000}$ to $d_{REF,003}$ may have definitions different from each other, such as, the standard representative input value $d_{REF,000}$ defined by formula (53) or the standard representative input values $d_{REF,001}$ to $d_{REF,003}$ defined by formula (54). The numbers $N_l$ of the standard filtered reference signals $r_{REF,00\zeta}(i)$ used for calculation of the standard representative input values $d_{REF,00\zeta}$ may differ from each other.

The standard step-size parameters $\mu_{REF,00\zeta}$ are, for example, expressed by formula (55) from maximum eigenvalues $\lambda_{REF,MAX,00\zeta}$ of an autocorrelation matrix of the standard filtered reference signals $R_{REF,00\zeta}$, similarly to formula (16).

$$\mu_{REF,00\zeta} = \frac{2}{\lambda_{REF,MAX,00\zeta}} \tag{55}$$

The representative input values $d_{00\zeta}(n)$ are determined based on the filtered reference signals $R_{m,00\zeta}(n)$ expressed by formula (56) that are $N_m$ filtered reference signals $r_{00\zeta}(i)$ from the current n-th step to the past by $(N_m-1)$ steps.

$$R_{m,00\zeta}(n)=[r_{00\zeta}(n), r_{00\zeta}(n-1), \ldots, r_{00\zeta}(n-(N_m-1))]^T \tag{56}$$

In the case that the standard representative input values $d_{REF,00\zeta}$ are expressed by formula (53), the representative input values $d_{00\zeta}(n)$ are determined by formula (57). In the case that the standard representative input values $d_{REF,00\zeta}$ are expressed by formula (54), the representative input values $d_{00\zeta}(n)$ are determined by formula (58).

$$d_{00\zeta}(n)=\left(\frac{1}{N_m}\sum_{m=0}^{N_m-1}(r_{00\zeta}(n-m))^2\right)^{\frac{1}{2}} \tag{57}$$

$$d_{00\zeta}(n)=\left(\frac{1}{N_m}\sum_{m=0}^{N_m-1}|r_{00\zeta}(n-m)|\right)^{2} \tag{58}$$

The representative input values $d_{00\zeta}(n)$ are determined by a definition corresponding to the standard representative input values $d_{REF,00\zeta}$. Therefore, when definitions different from each other are employed for the standard representative input values $d_{REF,00\zeta}$, for example, when the standard representative input value $d_{REF,000}$ is defined by formula 53) and when the standard representative input values $d_{REF,001}$ to $d_{REF,003}$ are defined by formula (54), the representative input values $d_{00\zeta}(n)$ and the representative input value $d_{000}(n)$ are defined by formula (57), and the representative input values $d_{001}(n)$ to $d_{003}(n)$ are defined by formula (58).

The step-size parameters $\mu_{00\zeta}(n)$ at the current n-th step are determined, for example, by formula (59) by dividing the standard step-size parameters $\mu_{REF,00\zeta}$ by a ratio of the representative input values $d_{00\zeta}(n)$ to the standard representative input values $d_{REF,00\zeta}$ similarly to formula (20).

$$\mu_{00\zeta}(n)=\mu_{REF,00\zeta}\cdot\frac{1}{\frac{d_{00\zeta}(n)}{d_{REF,00\zeta}}}=\mu_{REF,00\zeta}\cdot\frac{d_{REF,00\zeta}}{d_{00\zeta}(n)} \tag{59}$$

The μ-adjustment unit $\mathbf{8}_{00}$ thus determines the step-size parameters $\mu_{00\zeta}(i)$. Even when the reference signal $x_0(i)$ is large, the filter coefficient $W_{00}(i)$ of ADF $\mathbf{5}_{00}$ does not diverge. Even when the reference signal $x_0(i)$ is small, a converging speed of the filter coefficient $W_{00}(i)$ can be high.

The μ-adjustment units 8 calculates the step-size parameters $\mu_{\xi\eta\zeta}(n)$ at the current n-th step from the standard representative input values $d_{REF\xi\eta\zeta}$ and the standard step-size parameters $\mu_{REF,\xi\eta\zeta}$ based on each of plural standard filtered reference signals $r_{REF,\xi\eta\zeta}(i)$ in the standard driving condition, and the representative input values $d_{\xi\eta\zeta}(n)$ corresponding to the standard representative input values $d_{REF\xi\eta\zeta}$.

The standard representative input values $d_{REF,\xi\eta\zeta}$ can be given as constants, for example, by formula (60) similarly to formula (53) based on the standard filtered reference signals $R_{REF,\xi\eta\zeta}$ in the standard driving condition.

$$d_{REF,\xi\eta\zeta}=\left(\frac{1}{N_1}\sum_{1=0}^{N_1-1}(r_{REF,\xi\eta\zeta}(1))^2\right)^{\frac{1}{2}} \tag{60}$$

The standard representative input values $d_{REF,\xi\eta\zeta}$ may have definitions different from each other, and may employ different standard driving conditions. However, the standard step-size parameters $\mu_{REF,\xi\eta\zeta}$ are determined in a driving condition corresponding to the standard representative input values $d_{REF,\xi\eta\zeta}$.

Based on the filtered reference signals $R_{m\xi\eta\zeta}$ expressed by formula (61), the representative input values $d_{\xi\eta\zeta}(n)$ are determined by formula (62) in the case that the standard representative input values $d_{REF,\xi\eta\zeta}$ are expressed by formula (60).

$$R_{m,\xi\eta\zeta}(n)=[r_{\xi\eta\zeta}(n), r_{\xi\eta\zeta}(n-1), \ldots , r_{\xi\eta\zeta}(n-(N_m-1))]^T \tag{61}$$

$$d_{\xi\mu\zeta}(n)=\left(\frac{1}{N_m}\sum_{m=0}^{N_m-1}(r_{\xi\mu\zeta}(n-m))^2\right)^{\frac{1}{2}} \tag{62}$$

Similarly to formula (59), the step-size parameters $\mu_{\xi\eta\zeta}(n)$ at the current n-th step are determined by formula (63) by dividing the standard step-size parameters $\mu_{REF,\xi\eta\zeta}$ by a ratio of the representative input values $d_{\xi\eta\zeta}(n)$ to the standard representative input values $d_{REF,\xi\eta\zeta}$.

$$\mu_{\xi\mu\zeta}(n)=\mu_{REF,\xi\mu\zeta}\cdot\frac{1}{\frac{d_{\xi\mu\zeta}(n)}{d_{REF,\xi\mu\zeta}}}=\mu_{REF,\xi\mu\zeta}\cdot\frac{d_{REF,\xi\mu\zeta}}{d_{\xi\mu\zeta}(n)} \tag{63}$$

As described above, μ-adjustment units $\mathbf{8}_{\xi\eta}$ determine the step-size parameters $\mu_{\xi\eta\zeta}(i)$. Even when the reference signals $x_\xi(i)$ are large, active noise reduction device 201 operates stably without divergence of the filter coefficients $W_{\xi\eta}(i)$ of all ADFs $\mathbf{5}_{\xi\eta}$. Even when the reference signals $x_\xi(i)$ are small, the converging speed of the filter coefficients $W_{\xi\eta}(i)$ is high, and active noise reduction device 201 can reduce noise N0 effectively.

In an actual operation according to Embodiment 2, similarly to Embodiment 1, an arithmetic calculation amount can be reduced by storing a time-invariant constant part together as $\alpha_{\xi\eta\zeta}$ expressed by formula (21) and formula (22). For example, in the case that the standard representative input values $d_{REF,\xi\eta\zeta}$ are defined by formula (60) and the representative input values $d_{\xi\eta\zeta}$ are defined by formula (62), the time-invariant constant part can be stored together, as expressed by formula (64) and formula (65).

$$\begin{aligned}\mu_{\xi\eta\zeta}(n)&=\mu_{REF,\xi\eta\zeta}\cdot\frac{\left(\frac{1}{N_1}\sum_{1=0}^{N_1-1}(r_{REF,\xi\eta\zeta}(1))^2\right)^{\frac{1}{2}}}{\left(\frac{1}{N_m}\sum_{m=0}^{N_m-1}(r_{\xi\eta\zeta}(n-m))^2\right)^{\frac{1}{2}}}\\&=\frac{N_m^2\cdot\mu_{REF,\xi\eta\zeta}\cdot d_{REF,\xi\eta\zeta}}{\left(\sum_{m=0}^{N_m-1}(r_{\xi\eta\zeta}(n-m))^2\right)^{\frac{1}{2}}}=\frac{\alpha_{\xi\eta\zeta}}{\left(\sum_{m=0}^{N_m-1}(r_{\xi\eta\zeta}(n-m))^2\right)^{\frac{1}{2}}}\end{aligned} \tag{64}$$

$$\alpha_{\xi\mu\zeta}=N_m^2\cdot\mu_{REF,\xi\mu\zeta}\cdot d_{REF,\xi} \tag{65}$$

However, when active noise reduction device 201 operates according to the above equations, the number of the representative input values $d_{\xi\eta\zeta}(n)$ and the constants $\alpha_{\xi\eta\zeta}$ for updating the step-size parameters $\mu_{\xi\eta\zeta}(n)$ is a product of the number of reference signal sources $\mathbf{1}_\xi$, the number of secondary noise sources $\mathbf{2}_\eta$, and the number of error signal sources $\mathbf{3}_\zeta$. Accordingly, according to Embodiment 2, this number is as large as 64 (=4×4×4), hence increasing an arithmetic calculation load in signal-processing device 204.

In the case that active noise reduction device 201 is mounted to movable body 202, for example, when the filter coefficients $C\hat{}_{\eta\zeta}$ of Chat units $\mathbf{6}_{\eta\zeta}$ are time-invariant, it is not necessary to take into consideration a change of the filter coefficients $C\hat{}_{\eta\zeta}$ in calculation of the ratio of the representative input values $d_{\xi\eta\zeta}(i)$ to the standard representative input values $d_{REF,\xi\eta\zeta}$. Values by which the standard step-size parameters $\mu_{REF,\xi\eta\zeta}$ are multiplied often change similarly to each other. For example, ratios of the representative input values $d_{\xi\eta\zeta}(i)$ to the standard representative input values $d_{REF,\xi\eta\zeta}$ become larger during a drive on a road with an extremely rough surface. Accordingly, a set of at least one of the standard filtered reference signals $R_{REF,\xi\eta\zeta}$ and the filtered reference signals $R_{m,\xi\eta\zeta}(i)$ may be employed as a representative, and the standard representative input values $d_{REF,\xi\eta\zeta}$ and the representative input values $d_{\xi\eta\zeta}(i)$ may be calculated to adjust each of the standard step-size parameters $\mu_{REF,\xi\eta\zeta}$. At this moment, as the standard step-size parameters $\mu_{REF,\xi\eta\zeta}$, it is desirable to use values in the standard driving condition for determining the standard representative input values $d_{REF,\xi\eta\zeta}$ employed as a representative.

For example, according to Embodiment 2, in the case that the arithmetic calculation of μ-adjustment units $\mathbf{8}_{\xi\eta}$ employs, as representatives, a set of four standard filtered reference signals $R_{REF,000}$ to $R_{REF,300}$ and four filtered reference signals $R_{000}(n)$ to $R_{300}(n)$ that are output from Chat unit Goo, the step-size parameters $\mu_{\xi\eta\zeta}(n)$ can be determined by formula (66) using a ratio of the standard representative input values ($d_{REF,\xi}=d_{REF,\xi00}$) to the representative input values ($d_{\xi}(n)=d_{\xi00}(n)$).

$$\mu_{\xi\eta\zeta}(n) = \mu_{REF,\xi\eta\zeta} \cdot \frac{d_{REF,\xi}}{d_{\xi}(n)} \tag{66}$$

Similarly, according to Embodiment 2, in the case that the arithmetic operation of μ-adjustment units $\mathbf{8}_{\xi\eta}$ employs, as representatives, the standard filtered reference signals $r_{REF,0\eta\zeta}(i)$ and the filtered reference signals $r_{0\eta\zeta}(i)$ in the standard driving condition, the step-size parameters $\mu_{\epsilon\eta\zeta}(n)$ are determined by formula (67) using the standard representative input values ($d_{REF,\eta\zeta}=d_{REF,0\eta\zeta}$ to $d_{REF,3\eta\zeta}$) and the representative input values ($d_{\eta\zeta}(n)=d_{0\eta\zeta}(n)$ to $d_{3\eta\zeta}(n)$).

$$\mu_{\xi\eta\zeta}(n) = \mu_{REF,\xi\eta\zeta} \cdot \frac{d_{REF,\eta\zeta}}{d_{\eta\zeta}(n)} \tag{67}$$

Although the number of arithmetic calculations of the step-size parameters $\mu_{\xi\eta\zeta}(n)$ is not reduced by formula (66) or formula (67), the number of the representative input values $d_{\xi\eta\zeta}(n)$ can be 16 (=1×4×4) by formula (67) or 4 (=0.4×1×1) by formula (66), thereby reducing the arithmetic calculation load in signal-processing device 204.

If some standard step-size parameters $\mu_{REF\xi\eta\zeta}$ can be identical to each other, not only the number of the representative input values $d_{\xi\eta\zeta}(i)$ but also the number of constants $\alpha_{\xi\eta\zeta}$ can be reduced, thereby reducing the number of arithmetic calculations of the step-size parameters $\mu_{\xi\eta\zeta}(i)$.

For example, when each of the secondary noise signals $y_{\eta}(i)$ is calculated uniformly at positions of four error signal sources $\mathbf{3}_{\zeta}$, the standard step-size parameters $\mu_{REF,\xi\eta0}$ to $\mu_{REF,\xi\eta3}$ may employ common standard step-size parameters $\mu_{REF,\xi\eta}$. In addition to standard step-size parameters $\mu_{REF,\xi\eta}$, when the standard representative input values $d_{REF,\xi}$ and the representative input values d(n) are used as expressed by formula (66), step-size parameters $\mu_{\xi\eta}(n)$ can be determined by formula (68).

$$\mu_{\xi\eta}(n) = \mu_{REF,\xi\eta} \cdot \frac{d_{REF,\xi}}{d_{\xi}(n)} \tag{68}$$

When the step-size parameters $\mu_{\xi\eta}(n)$ expressed by formula (68) are used, the operation of LMS operation units $\mathbf{7}_{\xi\eta}$ expressed by formula (50) can be converted into that expressed by formula (69). This not only reduces the number of representative input values $d_{\xi\eta\zeta}(n)$ that need the operation to 4 (=4×1×1), but also reduces the number of operations of the step-size parameters $\mu_{\xi\eta\zeta}(n)$ to 16 (=4×1×4) of the step-size parameters ($\mu_{\xi\eta}(n)=\mu_{\xi\eta0}(n)$ to $\mu_{\xi\eta3}(n)$), thereby reducing power consumption and improving a processing speed.

$$W_{\xi\eta}(n+1) = W_{\xi\eta}(n) - \mu_{\xi\eta}(n) \cdot \sum_{\zeta=0}^{3} e_{\zeta}(n) \cdot R_{\xi\eta\zeta}(n) \tag{69}$$

According to Embodiment 2, similarly to Embodiment 1, even if the standard filtered reference signals $r_{REF,\xi\eta\zeta}(i)$ are not previously obtained by an experiment or a simulation, the filtered reference signals $r_{\xi\eta\zeta}(l)$ at a time of a drive start of movable body 202 may be used as the standard filtered reference signals $r_{REF,\xi\eta\zeta}(i)$ (where l is a small integer). Furthermore, in active noise reduction device 201, the standard representative input values $d_{REF,\xi\eta\zeta}$ and the standard step-size parameters $\mu_{REF,\xi\eta\zeta}$ can be updated when particular conditions, such as the amplitude of the filtered reference signals $r_{\xi\eta\zeta}(i)$ exceeds a maximum value of the amplitude of the standard filtered reference signals $r_{REF,\xi\eta\zeta}(i)$ in the standard driving condition during operation, is satisfied. In active noise reduction device 201, a similar effect is obtained when ADFs $\mathbf{5}_{n}$ use an adaptive algorithm, such as not only an FxLMS algorithm but also a projection algorithm, a SHARF algorithm, or a frequency region LMS algorithm, that utilizes step-size parameters. Furthermore, in active noise reduction device 201, the arithmetic calculation load of signal-processing device 204 can be reduced by a method of updating sequentially some of the filter coefficients $W_{\xi\eta}(i)$ and the step-size parameters $\mu_{\xi\eta\zeta}(i)$ without updating all the filter coefficients $W_{\xi\eta}(i)$ and step-size parameters $\mu_{\xi\eta\zeta}(i)$ of ADFs $\mathbf{5}_{\xi\eta}$ every sampling period $T_s$, or by not performing the operations of ADFs $\mathbf{5}_{\xi\eta}$ with a low contribution to noise reduction and accompanying LMS operation units $\mathbf{7}_{\xi\eta}$ and μ-adjustment units $\mathbf{8}_{\xi\eta}$.

Moreover, μ-adjustment units $\mathbf{8}_{\xi\eta}$ may store a combination data table of plural representative input values $d_{\xi\eta\zeta}(i)$ and plural step-size parameters $\mu_{\xi\eta\zeta}(i)$ calculated for respective ones of the representative input values $d_{\xi\eta\zeta}(i)$ based on formula (60). The μ-adjustment units $\mathbf{8}_{\xi\eta}$ can adjust the step-size parameters $\mu_{\xi\eta\zeta}(n)$ in a short time by reading, from the data table, values of the step-size parameters $\mu_{\xi\eta\zeta}(n)$ in accordance with values of the representative input values d(n). When a change in the driving condition is slower than the sampling period $T_s$ of active noise reduction device 201, μ-adjustment units may determine the step-size parameters $\mu_{\xi\eta\zeta}(n)$ at the current n-th step using the filtered reference signals $R_{m,\xi\eta\zeta}(n-\beta)$ (where β is a positive integer), before the current time instead of the filtered reference signals $R_{m,\xi\eta\zeta}(n)$ at the current time.

Similarly to μ-adjustment unit 8 of active noise reduction device 101, μ-adjustment units $\mathbf{8}_{\xi\eta}$ of active noise reduction device 201 according to Embodiment 2 may also provide the standard representative input values $d_{REF,\xi\eta\zeta}$ based not only on the standard filtered reference signals $r_{REF,\xi\eta\zeta}(i)$ but also on the standard error signals $e_{REF,\zeta}(i)$ in the standard driving condition. This is, for example, as expressed by formula (23), standard representative input values $d_{REF,\xi\eta\zeta}$ may be a product of the standard filtered reference signals $r_{REF,\xi\eta\zeta}(i)$ and the standard error signals $e_{REF,\zeta}(i)$ expressed by formula (70). Alternatively, as expressed by formula (24), standard representative input values $d_{REF,\xi\eta\zeta}$ may be an effective value of the standard error signals $e_{REF,\zeta}(i)$ expressed by formula (71).

$$d_{REF,\xi\eta\zeta} = \left(\frac{1}{N_1}\sum_{l=0}^{N_1-1} e_{REF,\zeta}(l)\cdot r_{REF,\xi\eta\zeta}(l)\right)^{\frac{1}{2}} \tag{70}$$

$$d_{REF,\xi\eta\zeta} = \left(\frac{1}{N_1}\sum_{l=0}^{N_1-1} (e_{REF,\zeta}(l))^2\right)^{\frac{1}{2}} \tag{71}$$

Since the representative input values $d_{\xi\eta\zeta}(i)$ are defined in a form corresponding to the standard representative input values $d_{REF,\xi\eta\zeta}$, the representative input values d(n) at the current n-th step are determined by formula (72) when the standard representative input values $d_{REF,\xi\eta\zeta}$ are expressed by formula (70). The representative input values d(n) are determined by formula (73) when the standard representative input values $d_{REF,\xi\eta\zeta}$ are expressed by formula (71).

$$d_{\xi\eta\zeta}(n) = \left(\frac{1}{N_m}\sum_{m=0}^{N_m-1} e_{\zeta}(n-m)\cdot r_{\xi\eta\zeta}(n-m)\right)^{\frac{1}{2}} \tag{72}$$

$$d_{\xi\eta\zeta}(n) = \left(\frac{1}{N_m}\sum_{m=0}^{N_m-1} (e_{\zeta}(n-m))^2\right)^{\frac{1}{2}} \tag{73}$$

Figure 11:
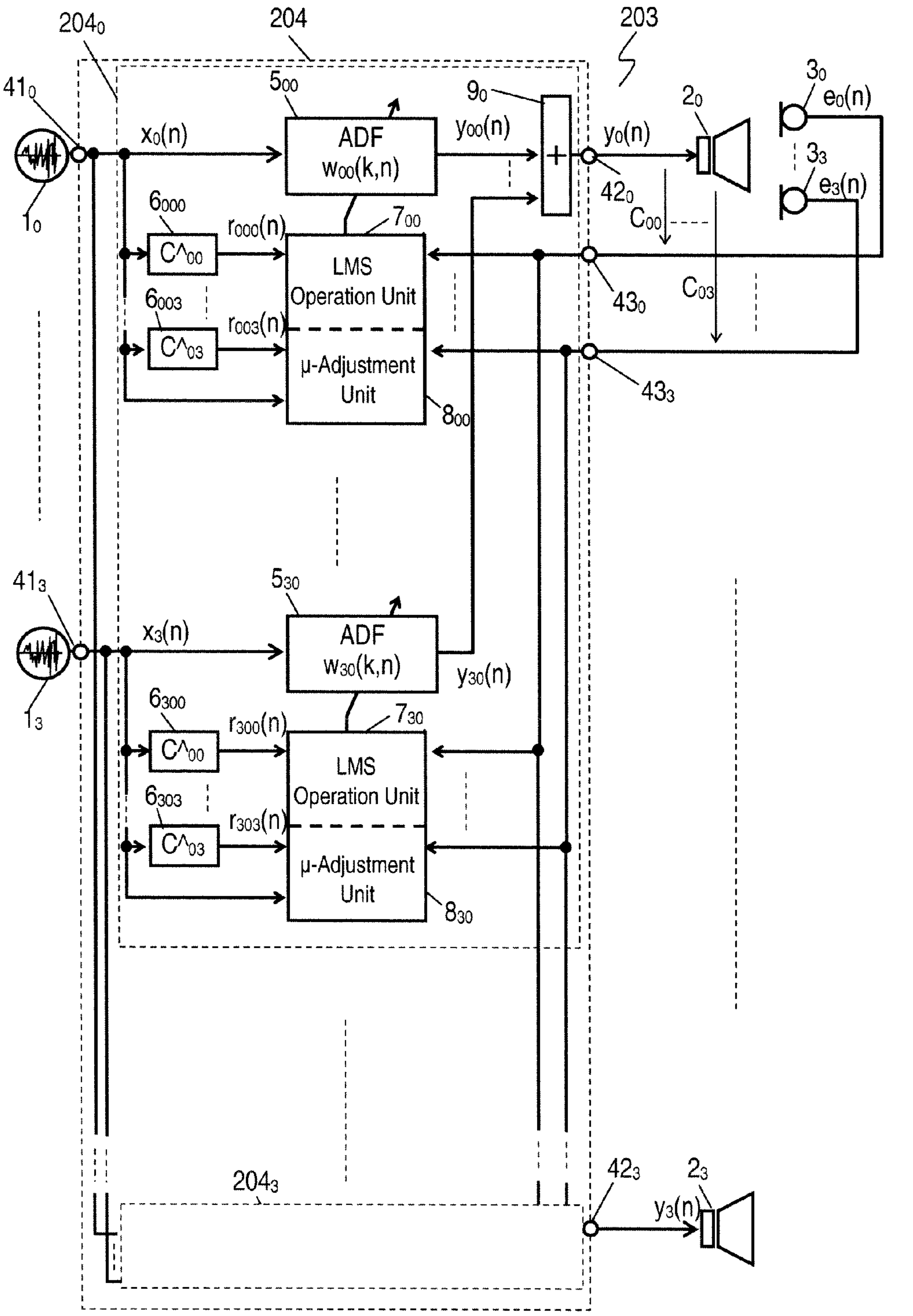
FIG. 11 is a block diagram of another active noise reduction device according to Embodiment 2.

Next, an operation of calculating the step-size parameters $\mu_{\xi\eta\zeta}(n)$ by setting the filter coefficients $\hat{c}_{\eta\zeta}(i)$ of Chat units $\mathbf{6}_{\eta\zeta}$ as time-invariant constants $\hat{c}_{\eta\zeta}$, and by using the standard reference signals $x_{REF,\xi\eta\zeta}(i)$ and the reference signals $x_{\xi\eta\zeta}(i)$ instead of the standard filtered reference signals $r_{REF,\xi\eta\zeta}(i)$ and the filtered reference signals $r_{\xi\eta\zeta}(i)$ according to Embodiment 2, similarly to Embodiment 1, FIG. 11 is a block diagram of another active noise reduction device 203 according to Embodiment 2. In FIG. 11, components identical to those of active noise reduction device 201 illustrated in FIG. 9 are denoted by the same reference numerals.

In active noise reduction device 203 illustrated in FIG. 11, μ-adjustment units $\mathbf{8}_{\xi\eta}$ calculate the step-size parameters $\mu_{\xi\eta\zeta}(n)$ using the standard reference signals $x_{REF,\xi}(i)$ and the reference signals $x_{\xi}(i)$ instead of the standard filtered reference signals $r_{REF,\xi\eta\zeta}(i)$ and the filtered reference signals $r_{\xi\eta\zeta}(i)$.

When the filter coefficients $\hat{c}_{\eta\zeta}(i)$ of Chat units $\mathbf{6}_{\eta\zeta}$ are considered as time-invariant constants $\hat{c}_{\eta\zeta}$, four standard filtered reference signals ($R_{REF,\xi}=R_{REF,\xi00}$) can be employed as representatives as described above, and it is not necessary to take into consideration a change of the filter coefficients $\hat{c}_{\eta\zeta}$ of Chat units $\mathbf{6}_{\eta\zeta}$. Therefore, based on the standard reference signals $X_{REF,\xi}$ in the standard driving condition instead of the standard filtered reference signals $R_{REF,\xi}$, the standard representative input values $d_{REF,\xi}$ can be provided by, for example, formula (74), similar to formula (60).

$$d_{REF,\xi} = \left(\frac{1}{N_1}\sum_{l=0}^{N_1-1} (x_{REF,\xi}(l))^2\right)^{\frac{1}{2}} \tag{74}$$

In the case that the standard representative input values $d_{REF,\xi}$ are expressed by formula (74), the representative input values $d_{\xi}(n)$ are calculated by formula (75) from the reference signals $X_{m,\xi}(i)$, similarly to the representative input values $d_{\xi}(n)$ expressed by formula (30).

$$d_{\xi} = \left(\frac{1}{N_m}\sum_{m=0}^{N_m-1} (x_{m,\xi}(n-m))^2\right)^{\frac{1}{2}} \tag{75}$$

Similarly to active noise reduction device 201 illustrated in FIG. 9, μ-adjustment units $\mathbf{8}_{\xi\eta}$ of active noise reduction device 203 can determine the step-size parameters $\mu_{\xi\eta\zeta}(n)$ at the n-th step by formula (66) using the standard representative input values $d_{REF,\xi}$ expressed by formula (74) and the representative input values $d_{\xi}(n)$ expressed by formula (75). Therefore, the number of parameters and arithmetic calculations for updating the step-size parameters can be reduced, and thus a processing load of μ-adjustment units $\mathbf{8}_{\xi\eta}$ can be smaller than the processing load of active noise reduction device 201.

Similarly to Embodiment 1, in a driving condition with a little variation of noise N0, the arithmetic calculation load for updating the step-size parameters $\mu_{\xi\eta\zeta}(n)$ can be reduced. In addition, μ-adjustment units $\mathbf{8}_{\xi\eta}$ may store a combination data table of plural step-size parameters $\mu_{\xi\eta\zeta}(i)$ to adjust the step-size parameters $\mu_{\xi\eta\zeta}(n)$ in a short time. When a change in the driving condition is slower than the sampling period $T_s$ of active noise reduction device 101, μ-adjustment units $\mathbf{8}_{\xi\eta}$ may determine the step-size parameters $\mu_{\xi\eta\zeta}(n)$ at the current n-th step using the filtered reference signals $R_{m,00\zeta}(n-\beta)$ before the current time (where β is a positive integer), instead of the filtered reference signals $R_{m,00\zeta}(n)$ at the current time.

Exemplary Embodiment 3

Figure 12:
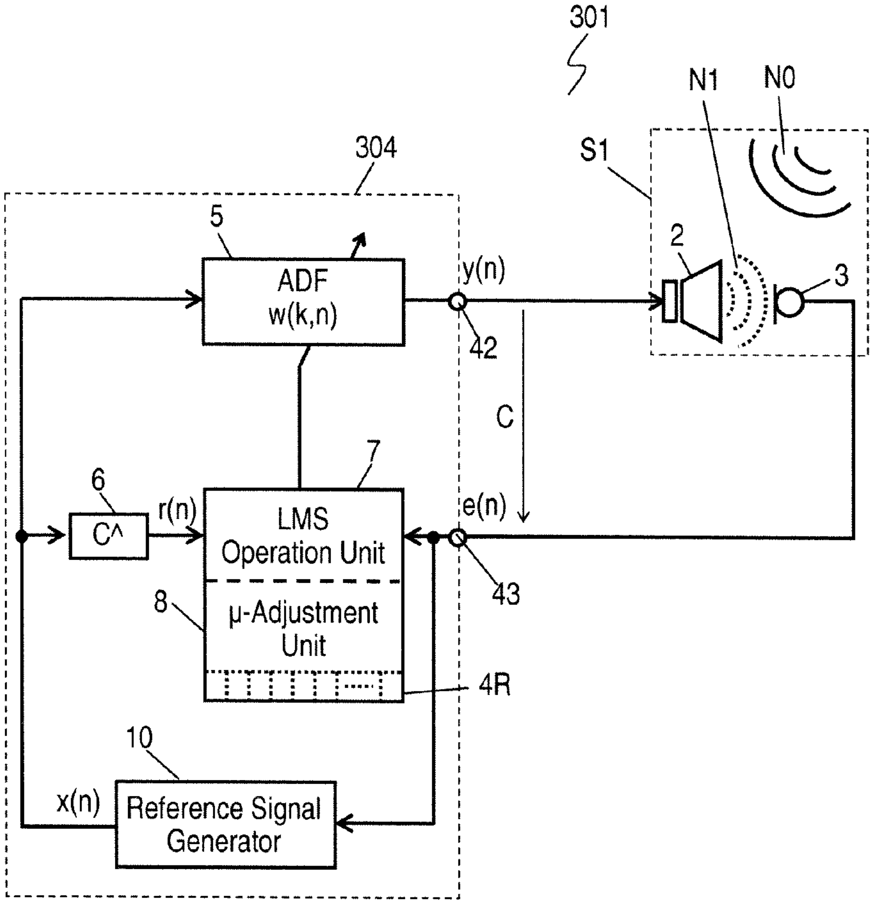
FIG. 12 is a block diagram of an active noise reduction device according to Exemplary Embodiment 3 of the present invention.
Figure 13:
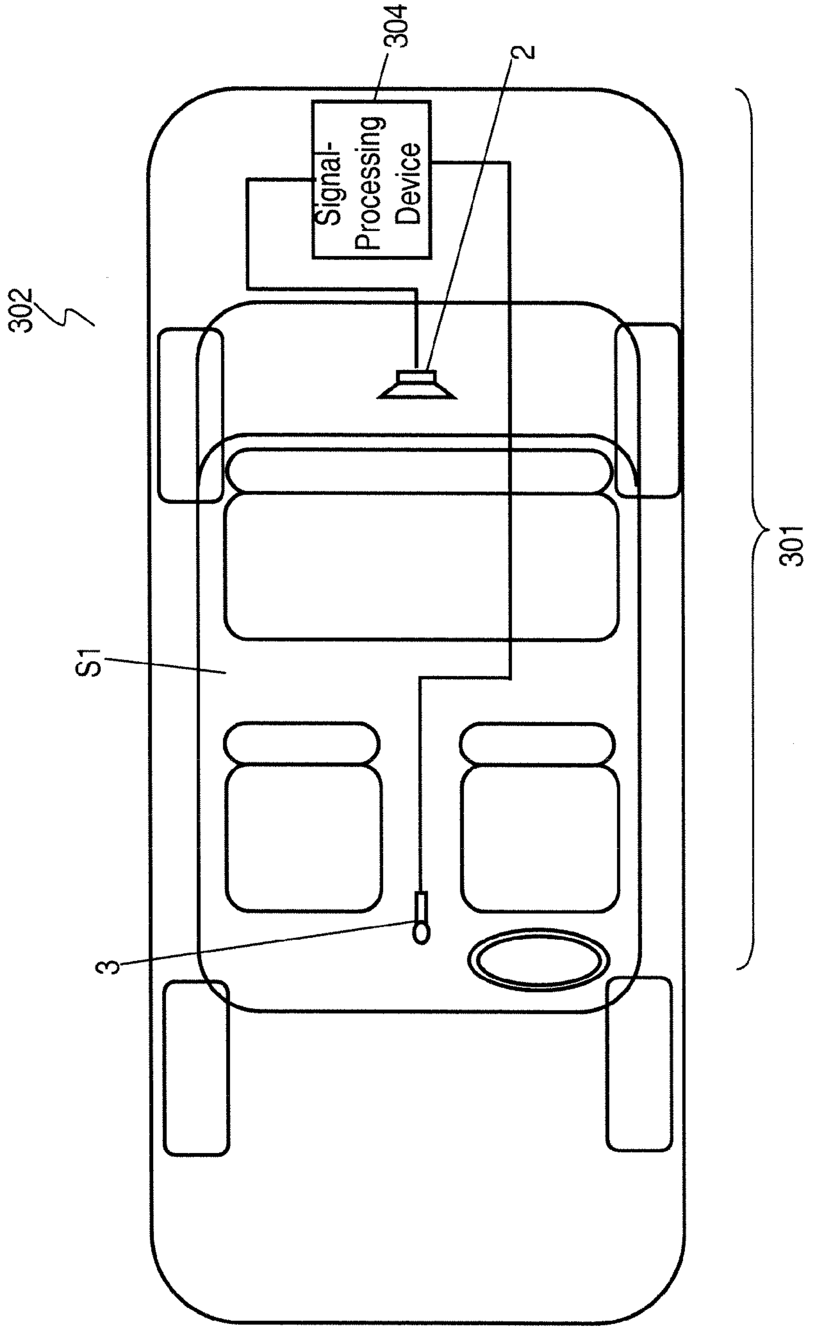
FIG. 13 is a schematic diagram of a movable body having the active noise reduction device according to Embodiment 3 mounted thereto.

FIG. 12 is a block diagram of active noise reduction device 301 according to Exemplary Embodiment 3 of the present invention. FIG. 13 is a schematic diagram of movable body 302 having active noise reduction device 301 mounted thereto. In FIGS. 12 and 13, components identical to those of active noise reduction device 101 and movable body 102 according to Embodiment 1 illustrated in FIGS. 1 and 2 are denoted by the same reference numerals. Movable body 302 according to Embodiment 3 is a vehicle that has space S1, such as a passenger compartment. Active noise reduction device 301 includes secondary noise source 2, error signal source 3, and signal-processing device 304. Signal-processing device 304 outputs a secondary noise signal y(i) in accordance with an error signal e(i). Secondary noise source 2 causes secondary noise N1 generated by reproducing the secondary noise signal y(i) to interfere with noise N0 generated in space S1, thereby reducing noise N0. Generally for such a feed-back type active noise control (ANC) according to Embodiment 3, signal-processing device 304 has a compensation unit, such as an echo canceller, for preventing recirculation of an audio signal that is output independently of a noise to error signal source 3. The compensation unit is omitted in the present embodiment for simplification of description, but this does not limit the use of the compensation unit.

Secondary noise source 2 is a transducer for outputting the secondary noise signal y(i) and generating secondary noise N1, and can be implemented by a loudspeaker installed in space S1. Secondary noise source 2 may be an actuator installed in a structure, such as a roof of movable body 302. In this case, a sound emitted from the structure excited by an output of the actuator corresponds to secondary noise N1. Generally, secondary noise source 2 may has a power amplifier for amplifying the secondary noise signal y(i), or is often driven by the secondary noise signal y(i) amplified by a power amplifying device provided outside. According to Embodiment 3, the power amplifier is included in secondary noise source 2, which does not limit this embodiment.

Error signal source 3 is a transducer, such as a microphone, for detecting a residual sound caused by interference between noise N0 and secondary noise N1 in space S1, and for outputting the error signal e(i) corresponding to the residual sound. Error signal source 3 is preferably installed in space S1 in which noise N0 is to be reduced.

Signal-processing device 304 includes input port 43 for acquiring the error signal e(i), output port 42 for outputting the secondary noise signal y(i), and an arithmetic operation unit for calculating the secondary noise signal y(i) based on the error signal e(i). Input port 43 and output port 42 may include a filter, such as a low pass filter, and a signal adjuster for adjusting amplitude and phase of the signal. The arithmetic operation unit is an arithmetic operation device, such as a microcomputer or a DSP, operating at discrete time intervals of a sampling period $T_s$. The arithmetic operation unit includes at least ADF 5, Chat unit 6, LMS operation unit 7, and μ-adjustment unit 8 for calculating a step-size parameter. The arithmetic operation unit may further include reference signal generator 10.

Reference signal generator 10 outputs a reference signal x(i) based on the error signal e(i). For example, reference signal generator 10 may read a signal stored previously from a pattern of the error signal e(i) to generate the reference signal x(i), or shift a phase of the error signal e(i) to generate the reference signal x(i). When the error signal e(i) is used as the reference signal x(i), signal-processing device 304 has a configuration identical to a configuration that does not include reference signal generator 10.

ADF 5 includes a finite impulse response (FIR) filter that has N filter coefficients w(k) with values updated by a filtered X-LMS (FxLMS) algorithm every sampling period $T_s$ (where k=0, 1, . . . , N−1). ADF 5 determines the secondary noise signal y(n) at the current n-th step by performing a filtering operation, that is, a convolution operation expressed by formula (76) on the filter coefficients w(k,n) and the reference signals x(i) generated by reference signal generator 10.

$$y(n)=\sum_{k=0}^{N-1} w(k,n)\cdot x(n-k) \tag{76}$$

Chat unit 6 has a filter coefficient C^(i) that simulates an acoustic transfer characteristic C(i) between output port 42 and input port 43 for the error signal e(i). In addition to a characteristic of secondary noise source 2 between output port 42 and input port 43 for the error signal e(i), and to an acoustic characteristic of space S1, the acoustic transfer characteristic C(i) may include a characteristic of a filter included in output port 42 and input port 43, and a delay of a signal caused by digital-to-analog conversion and analog-to-digital conversion. According to Embodiment 3, Chat unit 6 includes an FIR filter that has I1, time-invariant filter coefficients $c\hat{}(k_c)$ (where $k_c$=0, 1, . . . , $N_c$−1). The filter coefficient C^ of Chat unit 6 is a vector with $N_c$ rows and one column, and is expressed by formula (77).

$$C\hat{}=[c\hat{}(0),c\hat{}(1),\ldots,c\hat{}(N_c-1)]^T \tag{77}$$

Chat unit 6 may have time-variant filter coefficients $c\hat{}(k_c,n)$ that are updated or corrected by techniques described in, e.g. PYL 4 and PYL 5.

Chat unit 6 produces a filtered reference signal r(n) that is obtained by performing the filtering operation, that is, the convolution operation expressed by formula (78) on the filter coefficient C^ expressed by formula (77) and a reference signal X(n).

$$r(n)=\sum_{k_c=0}^{N_c-1} c^{\wedge}(k_c)\cdot x(n-k_c)=C^{\wedge T}X(n) \tag{78}$$

The reference signal X(n) is a vector with NT, rows and one column expressed by formula (79) composed of NT, reference signals x(i) from the current n-th step to the past by ($N_c$−1) steps.

$$X(n)=[x(n),x(n-1),\ldots,x(n-(N_c-1))]^T \tag{79}$$

The μ-adjustment unit 8 outputs a step-size parameter μ(n) at the current n-th step based on a predetermined standard step-size parameter $\mu_{REF}$ that is a standard step-size parameter previously determined, and on at least one of the reference signal x(i), the filtered reference signal r(i), and the error signal e(i).

LMS operation unit 7 updates the filter coefficient W(n) of ADF 5 by an FxLMS algorithm using the filtered reference signal R(n), the error signal e(n), and the step-size parameter μ(n) at the current n-th step. LMS operation unit 7 then calculates, by formula (80), the filter coefficient W(n+1) at the (n+1)-th step that is the next time.

$$W(n+1)=W(n)-\mu(n)\cdot e(n)\cdot R(n) \tag{80}$$

The filter coefficient W(n) of ADF 5 is a vector with N rows and one column composed of N filter coefficients w(k,n) at the current n-th step, and is expressed by formula (81) (where k=0, 1, . . . , N−1).

$$W(n)=[w(0,n),w(1,n),\ldots,w(N-1,n)]^T \tag{81}$$

The filtered reference signal R(n) is a vector with N rows and one column composed of N filtered reference signals r(i) from the current n-th step to the past by (N−1) steps, and is expressed by formula (82).

$$R(n)=[r(n),r(n-1),\ldots,r(n-(N-1))]^T \tag{82}$$

As described above, active noise reduction device 301 can determine an optimal secondary noise signal y(i) that cancels noise N0 at a position of error signal source 3 by updating the filter coefficient W(i) of ADF 5 every sampling period $T_s$ based on formula (80), thereby reducing noise N0 in space S1.

The μ-adjustment unit 8 stores a standard representative input value $d_{REF}$ and the standard step-size parameter $\mu_{REF}$. The standard representative input value $d_{REF}$ is an indicator for indicating the amplitude of a standard filtered reference signal $r_{REF}(i)$ that is the filtered reference signal r(i) in a driving condition used as a standard for movable body 302. Furthermore, μ-adjustment unit 8 determines a representative input value d(i) that is an indicator for indicating the amplitude of the filtered reference signal r(i) corresponding to the standard representative input value $d_{REF}$.

The μ-adjustment unit 8 calculates the step-size parameter μ(n) at the n-th step from the stored standard representative input value $d_{REF}$, the standard step-size parameter $\mu_{REF}$, and the representative input value d(n).

First, an operation of determining the standard representative input value $d_{REF}$ and the standard step-size parameter $\mu_{REF}$ will be described. According to Embodiment 3, a driving condition in which the amplitude of the filtered reference signal r(i) takes a maximum value is set to the standard driving condition. The driving condition in which the amplitude of the filtered reference signal r(i) takes a maximum value is, for example, that movable body 302 drives a road with an extremely rough surface. The standard filtered reference signal $r_{REF}(i)$ may be determined by measuring the filtered reference signal r(i) by an experiment, such as an actual driving experiment or a vibration experiment of movable body 302 in the standard driving condition. The standard filtered reference signal $r_{REF}(i)$ may be determined by a simulation, such as CAE. The standard representative input value $d_{REF}$ is provided as a constant based on the standard filtered reference signal $r_{REF}(i)$. For example, the standard representative input value $d_{REF}$ may be defined as a maximum value of the standard filtered reference signal $r_{REF}(i)$. Formula (83) defines a standard filtered reference signal $R_{REF}$ that is a vector with $N_l$ rows and one column composed of $N_l$ standard filtered reference signals $r_{REF}(i)$ from the l-th step that is a certain time in the standard driving condition to the past by $(N_l-1)$ steps.

$$R_{REF}=[r_{REF}(l),r_{REF}(l-1), \ldots ,r_{REF}(l-(N_l-1))]^T \tag{83}$$

The standard representative input value $d_{REF}$ may be provided as a constant, for example, an effective value expressed by formula (84) or a square of an average expressed by formula (85) based on the standard filtered reference signal $R_{REF}$ expressed by formula (83).

$$d_{REF} = \left(\frac{1}{N_l}\sum_{l=0}^{N_l-1}(r_{REF}(1))^2\right)^{\frac{1}{2}} \tag{84}$$

$$d_{REF} = \left(\frac{1}{N_l}\sum_{l=0}^{N_l-1}|r_{REF}(1)|^2\right)^2 \tag{85}$$

The standard step-size parameter $\mu_{REF}$ can be determined previously by an experiment or a simulation in the standard driving condition that determines the standard representative input value $d_{REF}$. For example, when the standard step-size parameter $\mu_{REF}$ is determined based on formula (12), the standard step-size parameter $\mu_{REF}$ is expressed by formula (86) by a maximum eigenvalue $\lambda_{REF,MAX}$ of an autocorrelation matrix of the standard filtered error signal $R_{REF}$.

$$\mu_{REF} = \frac{2}{\lambda_{REF,MAX}} \tag{86}$$

Next, an operation of determining the step-size parameter μ(n) at the current n-th step will be described. The representative input value d(n) is calculated from the filtered reference signal $R_m(n)$ expressed by formula (87). The filtered reference signal $R_m(n)$ is a vector with $N_m$ rows and one column from the current n-th step to the past by $(N_m-1)$ steps.

$$R_m(n)=[r(n),r(n-1), \ldots ,r(n-(N_m-1))]^T \tag{87}$$

The step number $N_m$ is preferably identical to the step number $N_l$ of the standard filtered reference signals $R_{REF}$ while both numbers may be different from each other. The representative input value d(n) is defined as a parameter corresponding to the standard representative input value $d_{REF}$. When the standard representative input value $d_{REF}$ is expressed by formula (84), the representative input value d(n) is determined by formula (88). When the standard representative input value $d_{REF}$ is defined by formula (85), the representative input value d(n) is determined by formula (89).

$$d(n) = \left(\frac{1}{N_m}\sum_{m=0}^{N_m-1}(r(n-m))^2\right)^{\frac{1}{2}} \tag{88}$$

$$d(n) = \left(\frac{1}{N_l}\sum_{m=0}^{N_m-1}|r(n-m)|\right)^2 \tag{89}$$

The step-size parameter μ(n) at the current n-th step is determined by formula (90) by dividing the standard step-size parameter $\mu_{REF}$ by a ratio of the representative input value d(n) to the standard representative input value $d_{REF}$.

$$\mu(n) = \mu_{REF}\cdot\frac{1}{\frac{d(n)}{d_{REF}}} = \mu_{REF}\cdot\frac{d_{REF}}{d(n)} \tag{90}$$

Since μ-adjustment unit 8 thus determines the step-size parameter μ(i), active noise reduction device 301 operates stably while the filter coefficient W(i) of ADF 5 diverges even when the reference signal x(i) is large. Furthermore, even when the reference signal x(i) is small, a converging speed of the filter coefficient W(i) is high, and active noise reduction device 301 can effectively reduce noise N0. In actual operation, for example, when the standard representative input value $d_{REF}$ is expressed by formula (85) and the representative input value d(n) is expressed by formula (89), μ-adjustment unit 8 can reduce an arithmetic calculation amount by storing a time-invariant constant part together as a constant α expressed by formula (91) and formula (92).

$$\mu(n) = \mu_{REF} \cdot \frac{\left(\frac{1}{N_l}\sum_{l=0}^{N_l-1}|r_{REF}(1)|\right)^2}{\left(\frac{1}{N_m}\sum_{m=0}^{N_m-1}|r(n-m)|\right)^2} = \frac{N_m^2 \cdot \mu_{REF} \cdot d_{REF}}{\left(\sum_{k=m}^{N_m-1}|r(n-m)|\right)^2} = \frac{\alpha}{\left(\sum_{k=m}^{N_m-1}|r(n-m)|\right)^2} \tag{91}$$

$$\alpha = N_m^2 \cdot \mu_{REF} \cdot d_{REF} \tag{92}$$

In a driving condition with a little variation of noise N0, it is also possible to reduce an arithmetic calculation load by updating the step-size parameter μ(n) not at each step but at predetermined intervals. In addition, μ-adjustment unit 8 may store a combination data table of plural representative input values d(i) and the plural step-size parameters μ(i) calculated with respect to each of the representative input values d(i) based on formula (90). The μ-adjustment unit 8 can adjust the step-size parameter μ(n) in a short time by reading, from the data table, a value of the step-size parameter μ(n) with respect to a value of the representative input value d(n). When a change in the driving condition is slower than the sampling period $T_s$ of active noise reduction device 301, μ-adjustment unit 8 may determine the step-size parameter μ(n) at the current n-th step using the filtered reference signal $R_m(n-\beta)$ at the previous time instead of the filtered reference signal $R_m(n)$ at the current time (where β is a positive integer).

Similarly to active noise reduction device 101 according to Embodiment 3 illustrated in FIG. 1, active noise reduction device 301 according to Embodiment 3 ensures stability of ADF 5 and the high converging speed as well.

Similarly to Embodiment 1, in active noise reduction device 301 according to Embodiment 3, an upper limit value and a lower limit value of each of a calculation result of the representative input value d(i) and a calculation result of the step-size parameter μ(i) may be determined. This configuration prevents the step-size parameter μ(i) from becoming excessively large, thus ensuring stability of an adaptive operation.

Even if the standard filtered reference signal $r_{REF}(i)$ is not obtained previously by an experiment or a simulation, the filtered reference signal r(l) (where l is a small integer) at the start of movable body 302 may be used as the standard filtered reference signal $r_{REF}(i)$. In active noise reduction device 301, it is also possible to update the standard representative input value $d_{REF}$ and the standard step-size parameter $\mu_{REF}$ when a particular condition, such as the amplitude of the filtered reference signal r(i) exceeds a maximum value of the amplitude of the standard filtered reference signal $r_{REF}(i)$ in the standard driving condition during operation, is satisfied.

In active noise reduction device 301 according to Embodiment 3, ADF 5 is an adaptive filter that utilizes the FxLMS algorithm. However, a similar effect is obtained even if ADF 5 utilizes an adaptive algorithm, such as a projection algorithm, a SHARF algorithm, or a frequency region LMS algorithm, that uses a step-size parameter.

Active noise reduction device 301 according to Embodiment 3 can reduce noise N0 not only in movable body 302 but also in a stationary device that has space S1 in which noise N0 exists.

Since the filtered reference signal r(i) is calculated from the reference signal x(i) based on the error signal e(i), the filtered reference signal r(i) is substantially determined from the error signal e(i). Particularly when the filter coefficients c^(i) of Chat unit 6 are time-invariant constants c^, the filtered reference signal r(i) has a fixed relationship with the reference signal x(i) as expressed by formula (7). Accordingly, the step-size parameter μ(i) may be calculated by using the standard reference signal $x_{REF}(i)$ and the reference signal x(i) instead of the standard filtered reference signal $r_{REF}(i)$ and the filtered reference signal r(i).

Moreover, since the reference signal x(i) is the error signal e(i) when reference signal generator 10 is not used, g-adjustment unit 8 calculates the step-size parameter μ(i) using the standard error signal $e_{REF}(i)$ and the error signal e(i) instead of the standard filtered reference signal $r_{REF}(i)$ and the filtered reference signal r(i). That is, instead of the filtered reference signal $R_m(n)$ expressed by formula (87), an error signal $E_m(n)$ that is a vector with $N_m$ rows and one column composed of $N_m$ error signals e(i) from the current n-th step to the past by $(N_m-1)$ steps is defined by formula (93).

$$E_m(n)=[e(n),e(n-1), \ldots ,e(n-(N_m-1))]^T \tag{93}$$

Instead of the standard filtered reference signal $R_{REF}$ with $N_l$ rows and one column expressed by formula (83) that is the standard filtered reference signal $r_{REF}(i)$, the standard error signal $E_{REF}$ that is a vector with $N_l$ rows and one column composed of $N_l$ standard error signals $e_{REF}(i)$ from the l-th step that is a certain time in the standard driving condition to the past by $(N_l-1)$ steps is defined as formula (94).

$$E_{REF}=[(e_{REF}(l),e_{REF}(l-1), \ldots ,e_{REF}(l-(N_l-1))]^T \tag{94}$$

The standard representative input value $d_{REF}$ may be given as a constant, for example, by an effective value expressed by formula (95) based on the standard error signal $E_{REF}$ expressed by formula (94).

$$d_{REF} = \left(\frac{1}{N_l}\sum_{l=0}^{N_l-1}(e_{REF}(1))^2\right)^{\frac{1}{2}} \tag{95}$$

The representative input value d(i) is defined as a parameter corresponding to the standard representative input value $d_{REF}$. When the standard representative input value $d_{REF}$ is expressed by formula (95), the representative input value d(i) is calculated from a reference error $E_m(n)$ by formula (96) similarly to the representative input value d(n) expressed by formula (88).

$$d(n) = \left(\frac{1}{N_m}\sum_{m=0}^{N_m-1}(e_m(n-m))^2\right)^{\frac{1}{2}} \tag{96}$$

The μ-adjustment unit 8 of active noise reduction device 301 determines the step-size parameter μ(n) at the n-th step by formula (90) using the standard representative input value $d_{REF}$ expressed by formula (95) and the representative input value d(n) expressed by formula (96).

As described above, active noise reduction device 301 is configured to be used together with secondary noise source 2 and error signal source 3. Secondary noise source 2 generates secondary noise N1 corresponding to the secondary noise signal y(i). Error signal source 3 outputs the error signal e(i) corresponding to the residual sound caused by interference between secondary noise N1 and noise N0. Active noise reduction device 301 includes signal-processing device 304 that has input port 43 for receiving the error signal e(i) and output port 42 for outputting the secondary noise signal y(i). Signal-processing device 304 includes ADF 5, Chat unit 6, LMS operation unit 7, and μ-adjustment unit 8, and may further include reference signal generator 10. Reference signal generator 10 generates the reference signal x(i) based on the error signal e(i). When signal-processing device 304 does not include reference signal generator 10, the error signal e(i) is used as the reference signal x(i). ADF 5 outputs the secondary noise signal y(i) in accordance with the reference signal x(i). Chat unit 6 corrects the reference signal x(i) with a simulated acoustic transfer characteristic that simulates an acoustic transfer characteristic from output port 42 to input port 43, and outputs the filtered reference signal r(i). LMS operation unit 7 updates the filter coefficients w(k,i) of ADF 5 by using the error signal e(i), the filtered reference signal r(i), and the step-size parameter μ(i). The μ-adjustment unit 8 determines the step-size parameter μ(i). The μ-adjustment unit 8 is operable to calculate the representative input value d(i) corresponding to the amplitude of at least one signal of the reference signal x(i), the filtered reference signal r(i), and the error signal e(i). The μ-adjustment unit 8 is operable to store the standard representative input value $d_{REF}$ and the predetermined standard step-size parameter $\mu_{REF}$. The standard representative input value $d_{REF}$ is the representative input value d(i) when amplitude of the at least one signal of the reference signal x(i), the filtered reference signal r(i), and the error signal e(i) is predetermined amplitude. The predetermined standard step-size parameter $\mu_{REF}$ is a value of the step-size parameter μ(i) to which the filter coefficients w(k,i) converge when the representative input value d(i) is the standard representative input value $d_{REF}$. The μ-adjustment unit 8 is operable to calculate the step-size parameter μ(i) by multiplying the standard step-size parameter $\mu_{REF}$ by a ratio of the standard representative input value $d_{REF}$ to the representative input value d(i). Active noise reduction device 301 reduces noise N0 by the above-described operations.

The standard step-size parameter $\mu_{REF}$ may take a maximum value of the step-size parameter μ(i) to which the filter coefficients w(k,i) converge when the representative input value d(i) is the standard representative input value $d_{REF}$.

The standard representative input value $d_{REF}$ may correspond to a maximum value of the amplitude of the at least one signal of the reference signal x(i), the filtered reference signal r(i), and the error signal e(i).

At least one value of an upper limit value and a lower limit value of a coefficient by which the standard step-size parameter $\mu_{REF}$ is multiplied may be determined. This coefficient may be a digital value expressed in register 4R of signal-processing device 304 that has a fixed-point format. In this case, μ-adjustment unit 8 sets the at least one value of the upper limit value and lower limit value of this coefficient by changing a decimal point position of this coefficient.

Active noise reduction device 301 is configured to be mounted in movable body 302 that has space S1. Noise N0 is generated in space S1. Secondary noise source 2 generates secondary noise N1 in space S1. The residual sound is generated in space S1.

Exemplary Embodiment 4

Figure 14:
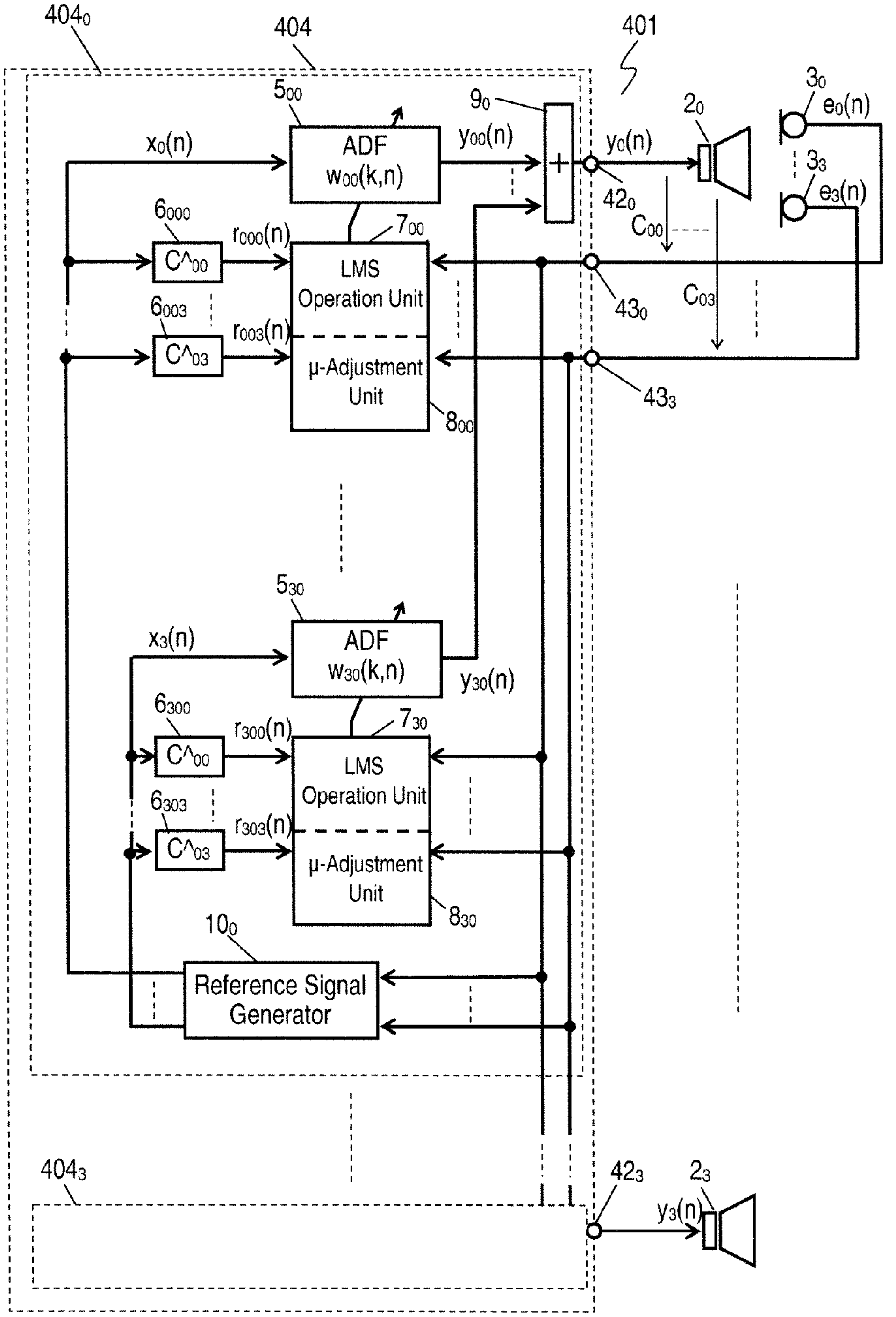
FIG. 14 is a block diagram of an active noise reduction device according to Exemplary Embodiment 4 of the present invention.
Figure 15:
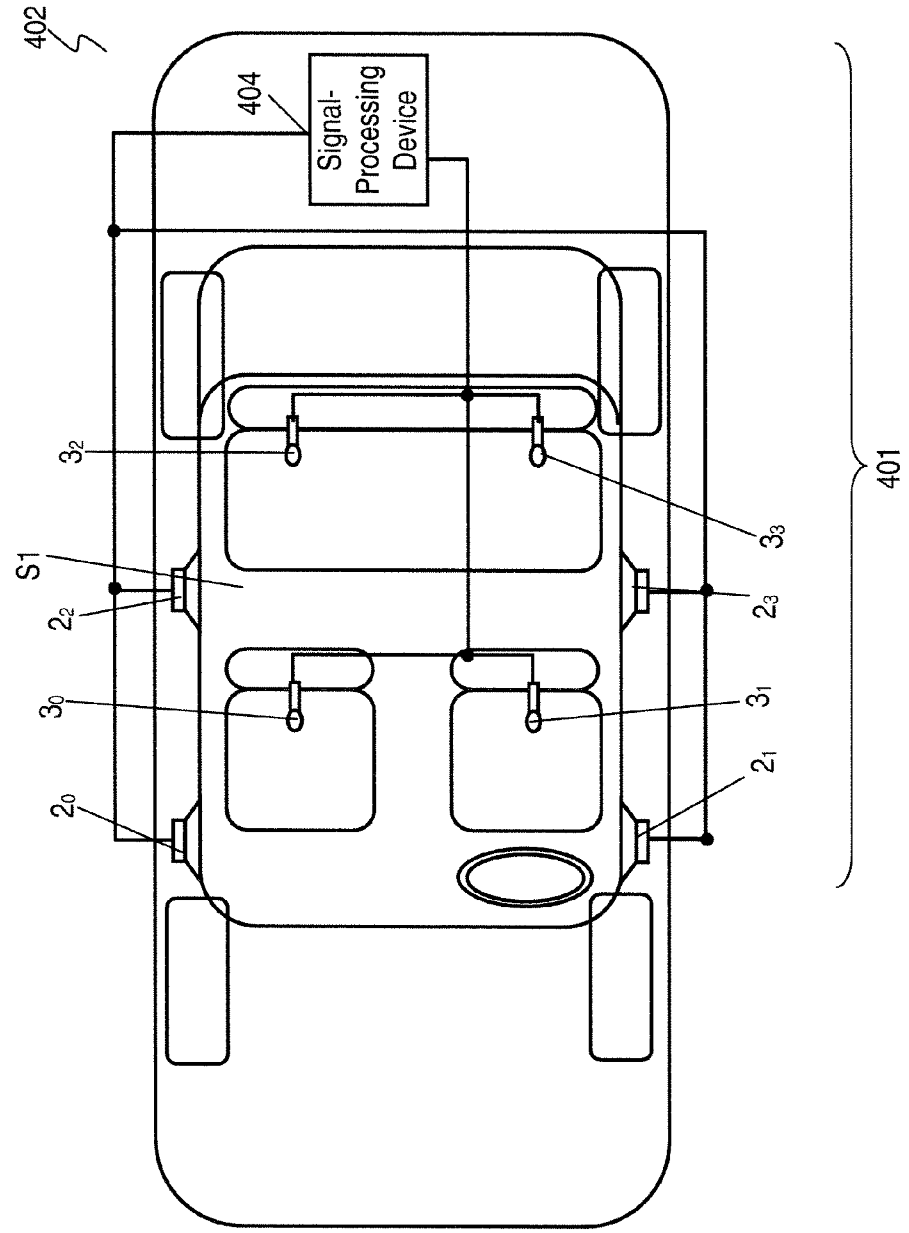
FIG. 15 is a schematic diagram of a movable body having the active noise reduction device according to Embodiment 4 mounted thereto.

FIG. 14 is a block diagram of active noise reduction device 401 according to Exemplary Embodiment 4 of the present invention. FIG. 15 is a schematic diagram of movable body 402 having active noise reduction device 401 mounted thereto. In FIGS. 14 and 15, components identical to those of active noise reduction device 301 and movable body 302 according to Embodiment 3 illustrated in FIGS. 12 and 13 are denoted by the same reference numerals.

Active noise reduction device 301 according to Embodiment 3 includes single secondary noise source 2, single error signal source 3, and signal-processing device 304. Active noise reduction device 401 can reduce a noise in space S1 due to signal-processing device 404, at least one secondary noise source $\mathbf{2}_{\eta}$, and at least one error signal source $\mathbf{3}_{\zeta}$.

Active noise reduction device 401 according to Embodiment 4 has a system configuration of a case (4,4) that includes four secondary noise sources $\mathbf{2}_0$ to $\mathbf{2}_3$ and four error signal sources $\mathbf{3}_0$ to $\mathbf{3}_3$. According to Embodiment 4, a system of case (4,4) will be described as an example. However, the numbers of secondary noise sources $\mathbf{2}_{\eta}$ and error signal sources $\mathbf{3}_{\zeta}$ are not limited to four. The device according to Embodiment 4 may have a configuration of a case (η,ζ) with the numbers different from each other.

In description in Embodiment 4, an identical subscript is given as a symbol that denotes an identical number, such as the number "ξ" of reference signals generated by reference signal generator $\mathbf{10}_{\eta}$, the number "η" of secondary noise sources, and the number "ζ" of error signal sources. A component, such as Chat unit $\mathbf{6}_{0_{\eta\zeta}}$, having plural elements is denoted by plural subscripts. For example, reference numeral "$6_{0_{\eta\zeta}}$" denotes that each of the η secondary noise sources is associated with ζ error signal sources, and Chat unit $\mathbf{6}_{0_{\eta\zeta}}$ has (η×ζ) components.

Signal-processing device 404 includes plural input ports $\mathbf{43}_{\zeta}$ for acquiring error signals $e_{\zeta}(i)$ output from error signal sources $\mathbf{3}_{\zeta}$, plural output ports $\mathbf{42}_{\eta}$ for outputting secondary noise signals $y_{\eta}(i)$ to secondary noise sources $\mathbf{2}_{\eta}$, and plural signal processors $\mathbf{404}_{\eta}$ for calculating the secondary noise signals $y_{\eta}(i)$. Signal-processing device 404 operates at a sampling period $T_s$. When a system of the case (η,ζ) fails to finish processing within the sampling period $T_s$ with one signal-processing device 404, the system may include plural signal-processing devices.

Signal processors $\mathbf{404}_{\eta}$ includes reference signal generator $\mathbf{10}_{\eta}$, plural ADFs $\mathbf{5}_{\xi\eta}$, plural Chat units $\mathbf{6}_{\xi\eta\zeta}$, plural LMS operation units plural μ-adjustment units $\mathbf{8}_{\xi\eta}$, and signal adder $\mathbf{9}_{\eta}$ for outputting a signal obtained by summing up plural signals.

Reference signal generator $\mathbf{10}_{\eta}$ outputs at least one of reference signals $x_{\xi}(i)$ based on at least one of the error signal $e_{\zeta}(i)$. Reference signal generator $\mathbf{10}_{\eta}$ may, for example, output C reference signals $x_{\xi}(i)$ corresponding to the error signals $e_{\zeta}(i)$, respectively. Reference signal generator $\mathbf{10}_{\eta}$ may output one reference signal x(i) from the ζ error signals $e_{\zeta}(i)$. Reference signal generator $\mathbf{10}_{\eta}$ may output plural reference signals $x_{\xi}(i)$ from one representative error signal $e_{\zeta}(i)$. In the device according to Embodiment 4, four reference signals $x_0(i)$ to $x_3(i)$ are output based on four error signals $e_0(i)$ to $e_3(i)$, respectively. Furthermore, in this embodiment, each of signal processors $\mathbf{404}_{\eta}$ includes reference signal generator $\mathbf{10}_{\eta}$. However, signal-processing device 404 may include one reference signal generator 10, and the reference signals x(i) generated by reference signal generator 10 may be input into signal processors $\mathbf{404}_{\eta}$.

An operation of signal processor $\mathbf{404}_{\eta}$ will be described below. Signal processor $\mathbf{404}_0$ that outputs the secondary noise signal $y_0(i)$ for driving secondary noise source $\mathbf{2}_0$ includes four sets of ADFs $\mathbf{5}_{00}$ to $\mathbf{5}_{30}$, LMS operation units $\mathbf{7}_{00}$ to $\mathbf{7}_{30}$, and μ-adjustment units $\mathbf{8}_{00}$ to $\mathbf{8}_{30}$. The number "four" is identical to the number of reference signals $x_{\xi}(i)$ output from reference signal generator $\mathbf{10}_0$. Signal processor $\mathbf{404}_0$ further includes signal adder $\mathbf{9}_0$ and sixteen Chat units $\mathbf{6}_{000}$ to $\mathbf{6}_{303}$. The number "sixteen" is a product of the number of error signal sources $\mathbf{3}_0$ to $\mathbf{3}_3$ and the number of reference signals $x_0(i)$ to $x_3(i)$ output from reference signal generator $\mathbf{10}_0$.

First, an operation of a set of ADF $\mathbf{5}_{00}$, LMS operation unit $\mathbf{7}_{00}$, μ-adjustment unit $\mathbf{8}_{00}$, and Chat unit $\mathbf{6}_{00\zeta}$ regarding the reference signal $x_0(i)$ will be described. ADF $\mathbf{5}_{00}$ determines the secondary noise signal $y_{00}(n)$ by performing a filtering operation on a filter coefficient $w_{00}(k,n)$ and the reference signal $x_0(i)$ by formula (97).

$$y_{00}(n) = \sum_{k=0}^{N-1} w_{00}(k, n) \cdot x_0(n-k) \tag{97}$$

Similarly to a filter coefficient C^(i) that simulates an acoustic transfer characteristic C(i) of a path between output port 42 and input port 43 for the error signal e(i) according to Embodiment 3, Chat units $\mathbf{6}_{0_{\eta\zeta}}$ have filter coefficients $C\hat{}_{\eta\zeta}(i)$ that simulate acoustic transfer characteristics $C_{\eta\zeta}(i)$ between output ports $\mathbf{42}_\eta$ and input ports $\mathbf{43}_\zeta$ for the error signals $e_\zeta(i)$ according to Embodiment 4, respectively. It is also assumed in Embodiment 4 that Chat units $\mathbf{6}_{\xi\eta\zeta}$ are time-invariant filter coefficients $C\hat{}_{\eta\zeta}$. Signal processor $\mathbf{404}_0$ includes four Chat units $\mathbf{6}_{000}$ to $\mathbf{6}_{003}$ corresponding to the number of error signals $e_\zeta(i)$. The filter coefficients $C\hat{}_{00}$ to $C\hat{}_{03}$ of Chat units $\mathbf{6}_{000}$ to $\mathbf{6}_{003}$ are expressed by formula (98).

$$\begin{aligned} C\hat{}_{00} &= [c\hat{}_{00}(0), c\hat{}_{00}(1), \ldots, c\hat{}_{00}(N_c-1)]^T \\ &\vdots \\ C\hat{}_{0\zeta} &= [c\hat{}_{0\zeta}(0), c\hat{}_{0\zeta}(1), \ldots, c\hat{}_{0\zeta}(N_c-1)]^T \\ &\vdots \\ C\hat{}_{03} &= [c\hat{}_{03}(0), c\hat{}_{03}(1), \ldots, c\hat{}_{03}(N_c-1)]^T \end{aligned} \tag{98}$$

Chat units $\mathbf{6}_{00\zeta}$ performs the filtering operation expressed by formula (99) on the filter coefficients $C\hat{}_{0\zeta}$ expressed by formula (98) and the reference signal $X_0(n)$ as to output filtered reference signals $r_{00\zeta}(n)$.

$$\begin{aligned} r_{000}(n) &= C\hat{}_{00}{}^T X_0(n) \\ &\vdots \\ r_{00\zeta}(n) &= C\hat{}_{0\zeta}{}^T X_0(n) \\ &\vdots \\ r_{003}(n) &= C\hat{}_{03}{}^T X_0(n) \end{aligned} \tag{99}$$

The reference signal $X_0(n)$ is a vector expressed by formula (100) composed of $N_c$ reference signals $x_0(i)$ from the current n-th step to the past by $(N_c-1)$ steps.

$$X_0(n)=[x_0(n),x_0(n-1), \ldots ,x_0(n-(N_c-1))]^T \tag{100}$$

The μ-adjustment unit $\mathbf{80}_0$ outputs step-size parameters $\mu_{00\zeta}(n)$ at the current n-th step based on predetermined standard step-size parameters $\mu_{REF,00\zeta}$ that are step-size parameters used as standards previously determined and at least one signal of the reference signals $x_0(i)$, filtered reference signals $r_{00\zeta}(i)$, and the error signals $e_\zeta(i)$.

LMS operation unit $\mathbf{7}_{00}$ updates the filter coefficient $W_{00}(n)$ of ADF $\mathbf{5}_{00}$ by formula (101) by using the four filtered reference signals $R_{00\zeta}(n)$, four error signals $e_\zeta(n)$, and four step-size parameters $\mu_{00\zeta}(n)$ determined by formula (99).

$$W_{00}(n+1) = W_{00}(n) - \sum_{\zeta=0}^{3} \mu_{00\zeta}(n) \cdot e_\zeta(n) \cdot R_{00\zeta}(n) \tag{101}$$

Filtered reference signals $R_{00\zeta}(n)$ are composed of the filtered reference signals $r_{00\zeta}(i)$ obtained by filtering the reference signals $x_0(i)$ with simulated acoustic transfer characteristics $C\hat{}_{0\zeta}$ as expressed by formula (102).

$$\begin{aligned} R_{000}(n) &= [r_{000}(n), r_{000}(n-1), \cdots, r_{000}(n-(N-1))]^T \\ &\vdots \\ R_{00\zeta}(n) &= [r_{00\zeta}(n), r_{00\zeta}(n-1), \cdots, r_{00\zeta}(n-(N-1))]^T \\ &\vdots \\ R_{003}(n) &= [r_{003}(n), r_{003}(n-1), \cdots, r_{003}(n-(N-1))]^T \end{aligned} \tag{102}$$

The filter coefficient $W_{00}(n)$ of ADF $\mathbf{5}_{00}$ is expressed by formula (103).

$$W_{00}(n)=[W_{00}(0,n),w_{00}(1,n), \ldots ,w_{00}(N-1,n)]^T \tag{103}$$

According to formula (101), the filtered reference signals $R_{00\zeta}(n)$ and the error signals $e_\zeta(n)$ contribute to the updating of the filter coefficient $W_{00}(n)$ to a degree indicated by the step-size parameters $\mu_{00\zeta}(n)$.

Next, an operation of determining the secondary noise signal $y_{00}(i)$ will be generalized regarding three sets of ADFs $\mathbf{5}_{10}$ to $\mathbf{5}_{30}$, LMS operation units $\mathbf{7}_{10}$ to $\mathbf{7}_{30}$, μ-adjustment units $\mathbf{8}_{10}$ to $\mathbf{8}_{30}$, and Chat units $\mathbf{6}_{10\zeta}$ to $\mathbf{6}_{30\zeta}$ that determine the secondary noise signals $y_{10}(i)$ to $y_{30}(i)$ in accordance with the other three reference signals $x_1(i)$ to $x_3(i)$.

The current secondary noise signals $y_{\xi 0}(n)$ determined by causing ADFs $\mathbf{5}_{\xi 0}$ to perform the filtering operation on the reference signals x(i) are obtained by formula (104).

$$y_{\xi 0}(n) = \sum_{k=0}^{N-1} w_{\xi 0}(k, n) \cdot x_\xi(n-k) \tag{104}$$

Chat units $\mathbf{6}_{\xi 0\zeta}$ output the filtered reference signals $r_{\xi 0\zeta}(n)$ by performing the arithmetic calculation expressed by formula (106) on the filter coefficients $C\hat{}_{0\zeta}$ expressed by formula (98) and the reference signals $X_\xi(n)$ expressed by formula (105).

$$X_\xi(n)=[x_\xi(n),x_\xi(n-1), \ldots ,x_\xi(n-(N_c-1))]^T \tag{105}$$

$$r_{\xi\eta\zeta}(n)=C\hat{}_{0\zeta}{}^T X_\xi(n) \tag{106}$$

The filtered reference signals $R_{\xi 0\zeta}(n)$ with N rows and one column composed of the filtered reference signals $r_{\xi 0\zeta}(i)$ are expressed by Formula (107).

$$R_{\xi 0\zeta}(n)=[r_{\xi 0\zeta}(n),r_{\xi 0\zeta}(n-1), \ldots ,r_{\xi 0\zeta}(n-(N-1))]^T \tag{107}$$

The μ-adjustment units $\mathbf{8}_{\xi 0}$ output the current step-size parameters $\mu_{\xi 0\zeta}(n)$ based on the standard step-size parameters $\mu_{REF,\xi 0\zeta}$, and at least one signal of the reference signals $x_\xi(i)$, the filtered reference signals $r_{\xi 0\zeta}(i)$, and the error signals $e_\zeta(i)$.

LMS operation units $\mathbf{7}_{\xi 0}$ update, by Formula (109), the filter coefficients $W_{\xi 0}(n)$ expressed by Formula (108).

$$W_{\xi 0}(n) = [w_{\xi 0}(0, n), w_{\xi 0}(1, n), \ldots , w_{\xi 0}(N-1, n)]^T \tag{108}$$

$$W_{\xi 0}(n+1) = W_{\xi 0}(n) - \sum_{\zeta=0}^{3} \mu_{\xi 0\zeta}(n) \cdot e_\zeta(n) \cdot R_{\xi 0\zeta}(n) \tag{109}$$

Signal adder $\mathbf{9}_0$ sums up thus-obtained four secondary noise signals $y_{00}(n)$ to $y_{30}(n)$, as expressed by formula (110), to generate the secondary noise signal $y_0(n)$ to be supplied to secondary noise source $\mathbf{2}_0$.

$$y_0(n) = \sum_{\xi=0}^{3} y_{\xi 0}(n) \tag{110}$$

Signal processors $\mathbf{404}_\eta$ that output the secondary noise signals $y_\eta(i)$ to secondary noise sources $\mathbf{2}_\eta$ including other secondary noise sources $\mathbf{2}_1$ to $\mathbf{2}_3$ will be described by expanding the operation of signal processor $\mathbf{404}_0$.

ADFs $\mathbf{5}_{\xi\eta}$ determine the secondary noise signals $y_{\xi\eta}(n)$ at the current n-th step by performing the filtering operation, that is, a convolution operation expressed by formula (111) using the filter coefficients $w_{\xi\eta}(k,n)$ and the reference signals $x_\xi(i)$.

$$y_{\xi\eta}(n) = \sum_{k=0}^{N-1} w_{\xi\eta}(k, n) \cdot x_\xi(n-k) \tag{111}$$

Chat units $\mathbf{6}_{\xi\eta\zeta}$ have the time-invariant filter coefficients $C\hat{}_{\eta\zeta}$ expressed by formula (112). The filter coefficients simulate the acoustic transfer characteristics $C_{\eta\zeta}(i)$ between output ports $\mathbf{42}_\eta$ and input ports $\mathbf{43}_\zeta$ for the error signals $e_\zeta(i)$.

$$C\hat{}_{\eta\zeta}=[c\hat{}_{\eta\zeta}(0),c\hat{}_{\eta\zeta}(1), \ldots ,c\hat{}_{\eta\zeta}(N_c-1)]^T \tag{112}$$

According to Embodiment 4, each of four secondary noise sources $\mathbf{2}_\eta$ has paths for four error signal sources $\mathbf{3}_\zeta$. Chat units $\mathbf{6}_{\xi\eta\zeta}$ have sixteen filters.

Chat units $\mathbf{6}_{\xi\eta\zeta}$ calculate the filtered reference signals $r_{\xi\eta\zeta}(n)$ by formula (113) from the filter coefficients $C\hat{}_{\eta\zeta}$ expressed by formula (112) and the reference signals $X_\xi(n)$ expressed by formula (105).

$$r_{\xi\eta\zeta}(n)=C\hat{}_{\eta\zeta}{}^T X_\xi(n) \tag{113}$$

The filtered reference signals $R_{\xi\eta\zeta}(n)$ with N rows and one column composed of the filtered reference signals $r_{\xi\eta\zeta}(i)$ are expressed by formula (114).

$$R_{\xi\eta\zeta}(n)=[r_{\xi\eta\zeta}(n),r_{\xi\eta\zeta}(n-1), \ldots ,r_{\xi\eta\zeta}(n-(N-1))]^T \tag{114}$$

The $\mu$-adjustment units output the current step-size parameters $\mu_{\xi\eta\zeta}(n)$ based on the standard step-size parameters $\mu_{REF,\xi\eta\zeta}$ and at least one signal of the reference signals $x_\xi(i)$, the filtered reference signals $r_{\xi\eta\zeta}(i)$, and the error signals $e_\zeta(i)$.

LMS operation units $\mathbf{7}_{\xi\eta}$ update, by formula (116), the filter coefficients $W_{\xi\eta}(n)$ expressed by formula (115).

$$W_{\xi\eta}(n) = [w_{\xi\eta}(0, n), w_{\xi\eta}(1, n), \ldots , w_{\xi\eta}(N-1, n)]^T \tag{115}$$

$$W_{\xi\eta}(n+1) = W_{\xi\eta}(n) - \sum_{\zeta=0}^{3} \mu_{\xi\eta\zeta}(n) \cdot e_\zeta(n) \cdot R_{\xi\eta\zeta}(n) \tag{116}$$

Signal adders $\mathbf{9}_\eta$ sums up the secondary noise signals $y_{\xi\eta}(n)$, as expressed by formula (117), to generate the secondary noise signals $y_\eta(n)$ to be supplied to secondary noise sources $\mathbf{2}_\eta$.

$$y_\eta(n) = \sum_{\xi=0}^{3} y_{\xi\eta}(n) \tag{117}$$

As described above, active noise reduction device 401 can determine the optimal secondary noise signals $y_\eta(n)$ that cancel noise N0 at positions of the plural error signal sources $\mathbf{3}_\zeta$, and can reduce noise N0 in space S1 by updating the filter coefficients $W_{\xi\eta}(n)$ of ADFs $\mathbf{5}_{\xi\eta}$ every sampling period $T_s$ based on formula (116).

Next, regarding an operation of calculating the step-size parameters $\mu_{\xi\zeta\eta}(n)$ at the current n-th step of $\mu$-adjustment units $\mathbf{8}_{\xi\eta}$, the following describes and generalizes the operation of $\mu$-adjustment unit $\mathbf{8}_{00}$ of a system that outputs the secondary noise signal $y_0(i)$ in accordance with the reference signal $x_0(i)$ and the error signal $e_0(i)$, similarly to the operation of signal processors $\mathbf{404}_\eta$.

The $\mu$-adjustment unit $\mathbf{8}_{00}$ stores standard representative input values $d_{REF,00\zeta}$ and the standard step-size parameters $\mu_{REF,00\zeta}$ based on the standard filtered reference signals $r_{REF,00\zeta}(i)$ that are the filtered reference signals $r_{00\zeta}(i)$ in a driving condition used as a standard for movable body 402. Moreover, $\mu$-adjustment unit $\mathbf{8}_{00}$ determines representative input values $d_{00\zeta}(n)$ corresponding to the standard representative input values $d_{REF,00\zeta}$ based on the filtered reference signals $r_{00\zeta}(i)$.

The $\mu$-adjustment unit $\mathbf{8}_{00}$ calculates the step-size parameters $\mu_{00\zeta}(n)$ from the stored standard representative input values $d_{REF,00\zeta}$, the standard step-size parameters $\mu_{REF,00\zeta}$, and the representative input values $d_{00\zeta}(n)$.

According to Embodiment 4, similarly to Embodiment 3, a driving condition is predetermined such that amplitude of the filtered reference signals $r_{00\zeta}(i)$ takes a maximum value as a standard driving condition, and an operation of determining the standard representative input values $d_{REF,00\zeta}$ and the standard step-size parameters $\mu_{REF,00\zeta}$ will be described Similarly to formula (83), the standard filtered reference signals $R_{REF,00\zeta}$ that are a vector with $N_l$ rows and one column composed of the standard filtered reference signals $r_{REF,00\zeta}(i)$ from the l-th step that is a certain time in the standard driving condition to the past by $(N_l-1)$ steps is defined as formula (118).

$$R_{REF,00\zeta}=[r_{REF,00\zeta}(l),r_{REF,00\zeta}(l-1), \ldots ,r_{REF,00\zeta}(l-(N_l-1))]^T \tag{118}$$

The standard representative input values $d_{REF,00\zeta}$ can be given, for example, as constants by an effective value expressed by formula (119) or by a square of an average value expressed by formula (120), similarly to formula (84) and formula (85), based on the standard filtered reference signals $R_{REF,00\zeta}$ expressed by formula (118).

$$d_{REF,00\zeta} = \left(\frac{1}{N_l}\sum_{l=0}^{N_l-1}(r_{REF,00\zeta}(l))^2\right)^{\frac{1}{2}} \tag{119}$$

$$d_{REF,00\zeta} = \left(\frac{1}{N_l}\sum_{l=0}^{N_l-1}|r_{REF,00\zeta}(l)|\right)^2 \tag{120}$$

Four standard representative input values $d_{REF,000}$ to $d_{REF,003}$ may have definitions different from each other. For example, the standard representative input value $d_{REF,000}$ is be defined by formula (119), and the standard representative input values $d_{REF,001}$ to $d_{REF,003}$ are defined by formula (120). The number $N_l$ of the standard filtered reference signals $r_{REF,00\zeta}(i)$ used for calculation of the standard representative input values $d_{REF,00\zeta}$ may be different from each other.

The standard step-size parameters $\mu_{REF,00\zeta}$ are expressed, for example, by formula 121) from maximum eigenvalues $\lambda_{REF,MAX,00\zeta}$ of an autocorrelation matrix of the standard filtered reference signals $R_{REF,00\zeta}$ similarly to formula (86).

$$\mu_{REF,00\zeta} = \frac{2}{\lambda_{REF,MAX,00\zeta}} \tag{121}$$

The representative input values $d_{00\zeta}(n)$ are determined based on the filtered reference signals $R_{m,00\zeta}(n)$ expressed by formula (122) that are $N_m$ filtered reference signals $r_{00\zeta}(i)$ from the current n-th step to the past by $(N_m-1)$ steps.

$$R_{m,00\zeta}(n)=[r_{00\zeta}(n),r_{00\zeta}(n-1), \ldots ,r_{00\zeta}(n-(N_m-1))]^T \tag{122}$$

In the case that the standard representative input values $d_{REF,00\zeta}$ are expressed by formula (119), the representative input values $d_{00\zeta}(n)$ are determined by formula (123). In the case that the standard representative input values $d_{REF,00\zeta}$ are expressed by formula (120), the representative input values $d_{00\zeta}(n)$ are determined by formula (124).

$$d_{00\zeta}(n) = \left(\frac{1}{N_m}\sum_{m=0}^{N_m-1}(r_{00\zeta}(n-m))^2\right)^{\frac{1}{2}} \tag{123}$$

$$d_{00\zeta} = \left(\frac{1}{N_m}\sum_{m=0}^{N_m-1}|r_{00\zeta}(n-m)|\right)^2 \tag{124}$$

The representative input values $d_{00\zeta}(n)$ are determined by a definition corresponding to the standard representative input values $d_{REF,00\zeta}$. Therefore, definitions different from each other may be employed for the standard representative input values $d_{REF,00\zeta}$. For example, the standard representative input value $d_{REF,000}$ is defined by formula (119), and the standard representative input values $d_{REF,001}$ to $d_{REF,003}$ are defined by formula (120). In this case, the representative input value $d_{000}(n)$ out of the representative input values $d_{00\zeta}(n)$ is defined by formula (123), and the representative input values $d_{001}(n)$ to $d_{003}(n)$ out of the representative input values $d_{00\zeta}(n)$ are defined by formula (124).

The step-size parameters $\mu_{00\zeta}(n)$ at the current n-th step are determined, for example, by formula (125) by dividing the standard step-size parameters $\mu_{REF,00\zeta}$ by a ratio of the representative input values $d_{00\zeta}(n)$ to the standard representative input values $d_{REF,00\zeta}$ similarly to formula (90).

$$\mu_{00\zeta}(n) = \mu_{REF,00\zeta}\cdot\frac{1}{\frac{d_{00\zeta}(n)}{d_{REF,00\zeta}}} = \mu_{REF,00\zeta}\cdot\frac{d_{REF,00\zeta}}{d_{00\zeta}(n)} \tag{125}$$

The μ-adjustment unit $\mathbf{8}_{00}$ thus determines the step-size parameters $\mu_{00\zeta}(i)$. Even when the reference signal $x_0(i)$ is large, the filter coefficient $W_{00}(i)$ of ADF $\mathbf{5}_{00}$ does not diverge. Moreover, even when the reference signal $x_0(i)$ is small, a converging speed of the filter coefficient $W_{00}(i)$ can be high.

The μ-adjustment units $\mathbf{8}_{\xi\eta}$ calculates the step-size parameters $\mu_{\xi\eta\zeta}(n)$ at the current n-th step from the standard representative input values $d_{REF,\xi\eta\zeta}$ and the standard step-size parameters $\mu_{REF,\xi\eta\zeta}$ based on each of the plural standard filtered reference signals $r_{REF,\xi\eta\zeta}(i)$ in the standard driving condition, and on the representative input values $d_{\xi\eta\zeta}(n)$ corresponding to each of the standard representative input values $d_{REF,\xi\eta\zeta}$.

The standard representative input values $d_{REF,\xi\eta\zeta}$ can be given, for example, as constants by formula (126) similarly to formula (119) based on the standard filtered reference signals $R_{REF,\xi\eta\zeta}$ in the standard driving condition.

$$d_{REF,\xi\eta\zeta} = \left(\frac{1}{N_l}\sum_{l=0}^{N_l-1}(r_{REF,\xi\eta\zeta}(l))^2\right)^{\frac{1}{2}} \tag{126}$$

The standard representative input values $d_{REF,\xi\eta\zeta}$ may have definitions different from each other and may employ different standard driving conditions. However, the standard step-size parameters $\mu_{REF,\xi\eta\zeta}$ are determined in a driving condition corresponding to the standard representative input values $d_{REF,\xi\eta\zeta}$.

Based on the filtered reference signals expressed $R_{m,\xi\eta\zeta}$ by formula (127), the representative input values $d_{\xi\eta\zeta}(n)$ are determined by formula (128) when the standard representative input values $d_{REF,\xi\eta\zeta}$ are expressed by formula (126).

$$R_{m,\xi\eta\zeta}(n) = [r_{\xi\eta\zeta}(n), r_{\xi\eta\zeta}(n-1), \ldots , r_{\xi\eta\zeta}(n-(N_m-1))]^T \tag{127}$$

$$d_{\xi\eta\zeta}(n) = \left(\frac{1}{N_m}\sum_{m=0}^{N_m-1}(r_{\xi\eta\zeta}(n-m))^2\right)^{\frac{1}{2}} \tag{128}$$

Similarly to formula (127), the step-size parameters $\mu_{\xi\eta\zeta}(n)$ at the current n-th step are determined by formula (129) by dividing the standard step-size parameters $\mu_{REF,\xi\eta\zeta}$ by a ratio of the representative input values $d_{\xi\eta\zeta}(n)$ to the standard representative input values $d_{REF,\xi\eta\zeta}$.

$$\mu_{\xi\eta\zeta}(n) = \mu_{REF,\xi\eta\zeta}\cdot\frac{1}{\frac{d_{\xi\eta\zeta}(n)}{d_{REF,\xi\eta\zeta}}} = \mu_{REF,\xi\eta\zeta}\cdot\frac{d_{REF,\xi\eta\zeta}}{d_{\xi\eta\zeta}(n)} \tag{129}$$

The μ-adjustment units $\mathbf{8}_{\xi\eta}$ thus determine the step-size parameters $\mu_{\xi\eta\zeta}(i)$. Even when the reference signals $x_\xi(i)$ are large, active noise reduction device 401 operates stably without divergence of the filter coefficients $W_{\xi\eta}(i)$ of all ADFs $\mathbf{5}_{\xi\eta}$. Moreover, even when the reference signals $x_\xi(i)$ are small, the converging speed of the filter coefficients $W_{\xi\eta}(i)$ is high, and active noise reduction device 401 can reduce noise N0 effectively.

In actual operation, according to Embodiment 4, similarly to Embodiment 3, an arithmetic calculation amount can be reduced by storing a time-invariant constant part together as $\alpha_{\xi\eta\zeta}$ expressed by formula (91) and formula (92). For example, in the case that the standard representative input values $d_{REF,\xi\eta\zeta}$ are defined by formula (126 and the representative input values $d_{\xi\eta\zeta}$ are defined by formula (128), the time-invariant constant part can be stored together as expressed by formula (130) and formula (131).

$$\mu_{\xi\eta\zeta}(n) = \mu_{REF,\xi\eta\zeta}\cdot\frac{\left(\frac{1}{N_l}\sum_{l=0}^{N_l-1}(r_{REF,\xi\eta\zeta}(l))^2\right)^{\frac{1}{2}}}{\left(\frac{1}{N_m}\sum_{m=0}^{N_m-1}(r_{\xi\eta\zeta}(n-m))^2\right)^{\frac{1}{2}}} = \frac{N_m^2\cdot\mu_{REF,\xi\eta\zeta}\cdot d_{REF,\xi\eta\zeta}}{\left(\sum_{m=0}^{N_m-1}(r_{\xi\eta\zeta}(n-m))^2\right)^{\frac{1}{2}}} = \frac{\alpha_{\xi\eta\zeta}}{\left(\sum_{m=0}^{N_m-1}(r_{\xi\eta\zeta}(n-m))^2\right)^{\frac{1}{2}}} \quad (130)$$

$$\alpha_{\xi\eta\zeta} = N_m^2\cdot\mu_{REF,\xi\eta\zeta}\cdot d_{REF,\xi\eta\zeta} \quad (131)$$

However, when active noise reduction device 401 operates according to the above-described equations, the number of representative input values $d_{\xi\eta\zeta}(n)$ for updating the step-size parameters $\mu_{\xi\eta\zeta}(n)$ or the number of constants $\alpha_{\xi\eta\zeta}$ are a product of the number of reference signals $x_\xi(i)$ output from reference signal generator $\mathbf{10}_\eta$, the number of error signal sources $\mathbf{3}_\zeta$, and the number of secondary noise sources $\mathbf{2}_\eta$. Accordingly, according to Embodiment 4, this number is as large as 64 (=−4×4×4), and an arithmetic calculation load in signal-processing device 404 becomes larger.

In active noise reduction device 401 mounted to movable body 402, for example, when the filter coefficients $\hat{C}_{\eta\zeta}$ of Chat units $\mathbf{6}_{\eta\zeta}$ are time-invariant, it is not necessary to take into consideration a change of the filter coefficients $\hat{C}_{\eta\zeta}$ in calculation of a ratio of the representative input values $d_{\xi\eta\zeta}(i)$ to the standard representative input values $d_{REF,\xi\eta\zeta}$. A value by which the standard step-size parameters $\mu_{REF,\xi\eta\zeta}$ are multiplied often changes similarly to each other. For example, the ratio of the representative input values $d_{\xi\eta\zeta}(i)$ to the standard representative input values $d_{REF,\xi\eta\zeta}$ becomes larger during a drive on a road with an extremely rough surface. Accordingly, a set of at least one of the standard filtered reference signals $R_{REF,\xi\eta\zeta}$ and the filtered reference signals $R_{m,\xi\eta\zeta}(i)$ may be employed as a representative, and the standard representative input values $d_{REF,\xi\eta\zeta}$ and the representative input values $d_{\xi\eta\zeta}(i)$ may be calculated to adjust each standard step-size parameter $\mu_{REF,\xi\eta\zeta}$. At this moment, the standard step-size parameters $\mu_{REF,\xi\eta\zeta}$, is preferably values in a standard driving condition in which the standard representative input values $d_{REF,\xi\eta\zeta}$ employed as a representative are determined.

For example, according to Embodiment 4, when an arithmetic calculation of μ-adjustment units $\mathbf{8}_{\xi\eta}$ employs, as representatives, a set of four standard filtered reference signals $R_{REF,000}$ to $R_{REF,300}$ and four filtered reference signals $R_{000}(n)$ to $R_{300}(n)$ that are output from Chat unit $\mathbf{6}_{00}$, the step-size parameters $\mu_{\xi\eta\zeta}(n)$ can be determined by formula (132) using a ratio of the standard representative input values ($d_{REF,\xi}=d_{REF,\xi00}$) to the representative input values ($d_\xi(n)=d_{\xi00}(n)$).

$$\mu_{\xi\eta\zeta}(n) = \mu_{REF,\xi\eta\zeta}\cdot\frac{d_{REF,\xi}}{d_\xi(n)} \quad (132)$$

Similarly, according to Embodiment 4, when the arithmetic calculation of μ-adjustment units $\mathbf{8}_{\xi\eta}$ employs, as representatives, the standard filtered reference signals $r_{REF,0\eta\zeta}(i)$ and the filtered reference signals $r_{0\eta\zeta}(i)$ in the standard driving condition, the step-size parameters $\mu_{\xi\eta\zeta}(n)$ are determined by formula (133) using the standard representative input values ($d_{REF,\eta\zeta}=d_{REF,0\eta\zeta}$ to $d_{REF,3\eta\zeta}$) and the representative input values ($d_{\eta\zeta}(n)=d_{0\eta\zeta}(n)$ to $d_{3\eta\zeta}(n)$).

$$\mu_{\xi\eta\zeta}(n) = \mu_{REF,\xi\eta\zeta}\cdot\frac{d_{REF,\eta\zeta}}{d_{\eta\zeta}(n)} \quad (133)$$

Although the number of arithmetic calculations of the step-size parameters $\mu_{\xi\eta\zeta}(n)$ is not reduced by formula (132) or formula (133), the number of representative input values $d_{\xi\eta\zeta}(n)$ can be set to 16 (=1×4×4) by formula (133), or can be set to 4 (4×1×1) by formula (132), thereby reducing the arithmetic calculation load in signal-processing device 404.

Moreover, when some of standard step-size parameters $\mu_{REF,\xi\eta\zeta}$ can be identical values, not only the number of representative input values $d_{\xi\eta\zeta}(i)$ but also the number of constants $\alpha_{\xi\eta\zeta}$ can be reduced, thereby reducing the number of arithmetic calculations of step-size parameters $\mu_{\xi\eta\zeta}(i)$.

For example, when each of the secondary noise signals $y_\eta(i)$ is calculated such that positions of four error signal sources $\mathbf{3}_\zeta$ are reduced uniformly, the standard step-size parameters $\mu_{REF,\xi\eta0}$ to $\mu_{REF,\xi\eta3}$ may employ common standard step-size parameters $\mu_{REF,\xi\eta}$. In addition to these standard step-size parameters $\mu_{REF,\xi\eta}$, when the standard representative input values $d_{REF,\xi}$ and the representative input values $d_\xi(n)$ are used as expressed by formula (132), the step-size parameters $\mu_{\xi\eta}(n)$ can be determined by formula (134).

$$\mu_{\xi\eta}(n) = \mu_{REF,\xi\eta}\cdot\frac{d_{REF,\xi}}{d_\xi(n)} \quad (134)$$

When the step-size parameters $\mu_{\xi\eta}(n)$ expressed by formula (134) are used, the operation of LMS operation units $\mathbf{7}_{\xi\eta}$ expressed by formula (116) can be converted into formula (135). This not only reduces the number of representative input values $d_{\xi\eta\zeta}(n)$ that need the operation to 4 (=4×1×1), but also reduces the number of operations of the step-size parameters $\mu_{\xi\eta\zeta}$ to 16 (=4×1×4) of the step-size parameters ($\mu_{\xi\eta}(n)=\mu_{\xi\eta}$ (n) to $\mu_{\xi\eta3}(n)$), thereby reducing power consumption and improving in a processing speed.

$$W_{\xi\eta}(n+1) = W_{\xi\eta}(n) - \mu_{\xi\eta}(n)\cdot\sum_{\zeta=0}^{3} e_\zeta(n)\cdot R_{\xi\eta\zeta}(n) \quad (135)$$

According to Embodiment 4, similarly to Embodiment 3, even if the standard filtered reference signals $r_{REF,\xi\eta\zeta}(i)$ are not previously provided by an experiment or a simulation, the filtered reference signals $r_{\xi\eta\zeta}(l)$ at a time of the start of driving movable body 402 may be used as the standard filtered reference signals $r_{REF,\xi\eta\zeta}(i)$ (where l is a small integer). Furthermore, in active noise reduction device 401, the standard representative input values $d_{REF,\xi\eta\zeta}$ and the standard step-size parameters $\mu_{REF,\xi\eta\zeta}$ can be updated when particular conditions, such as amplitude of the filtered reference signals $r_{\xi\eta\zeta}(i)$ exceeds a maximum value of the amplitude of the standard filtered reference signals $r_{REF,\xi\eta\zeta}(i)$ in the standard driving condition during operation, is satisfied. In active noise reduction device 401, a similar effect is obtained when ADFs $5_{\xi\eta}$ utilize an adaptive algorithm, such as not only an FxLMS algorithm but also a projection algorithm, a SHARF algorithm, or a frequency region LMS algorithm, that uses step-size parameters. Furthermore, in active noise reduction device 401, the arithmetic calculation load of signal-processing device 404 can be reduced by a method of updating sequentially some of the filter coefficients $W_{\xi\eta}(i)$ and the step-size parameters $\mu_{\xi\eta\zeta}(i)$ without updating all the filter coefficients $W_{\xi\eta}(i)$ and step-size parameters $\mu_{\xi\eta\zeta}(i)$ of ADFs $5_{\xi\eta}$ every sampling period $T_s$, or by not performing operations of ADFs $5_{\xi\eta}$ with a low contribution to noise reduction and accompanying LMS operation units $7_{\xi\eta}$ and μ-adjustment units $8_{\xi\eta}$.

Moreover, μ-adjustment units $8_{\xi\eta}$ may store a combination data table of the plural representative input values $d_{\xi\eta\zeta}(i)$ and the plural step-size parameters $\mu_{\xi\eta\zeta}(i)$ calculated for each of the representative input values $d_{\xi\eta\zeta}(i)$ based on formula (126). The μ-adjustment units $8_{\xi\eta}$ can adjust the step-size parameters $\mu_{\xi\eta\zeta}(n)$ in a short time by reading, from the data table, values of the step-size parameters $\mu_{\xi\eta\zeta}(n)$ in response to values of the representative input values d(n). When a change in the driving condition is slower than the sampling period $T_s$ of active noise reduction device 401, μ-adjustment units $8_{\eta\zeta}$ may determine the step-size parameters $\mu_{\xi\eta\zeta}(n)$ at the current n-th step using the filtered reference signals $R_{m,\xi\eta\zeta}(n-\beta)$ at a previous time (where β is a positive integer), instead of the filtered reference signals $R_{m,\xi\eta\zeta}(n)$ at the current time.

Figure 16:
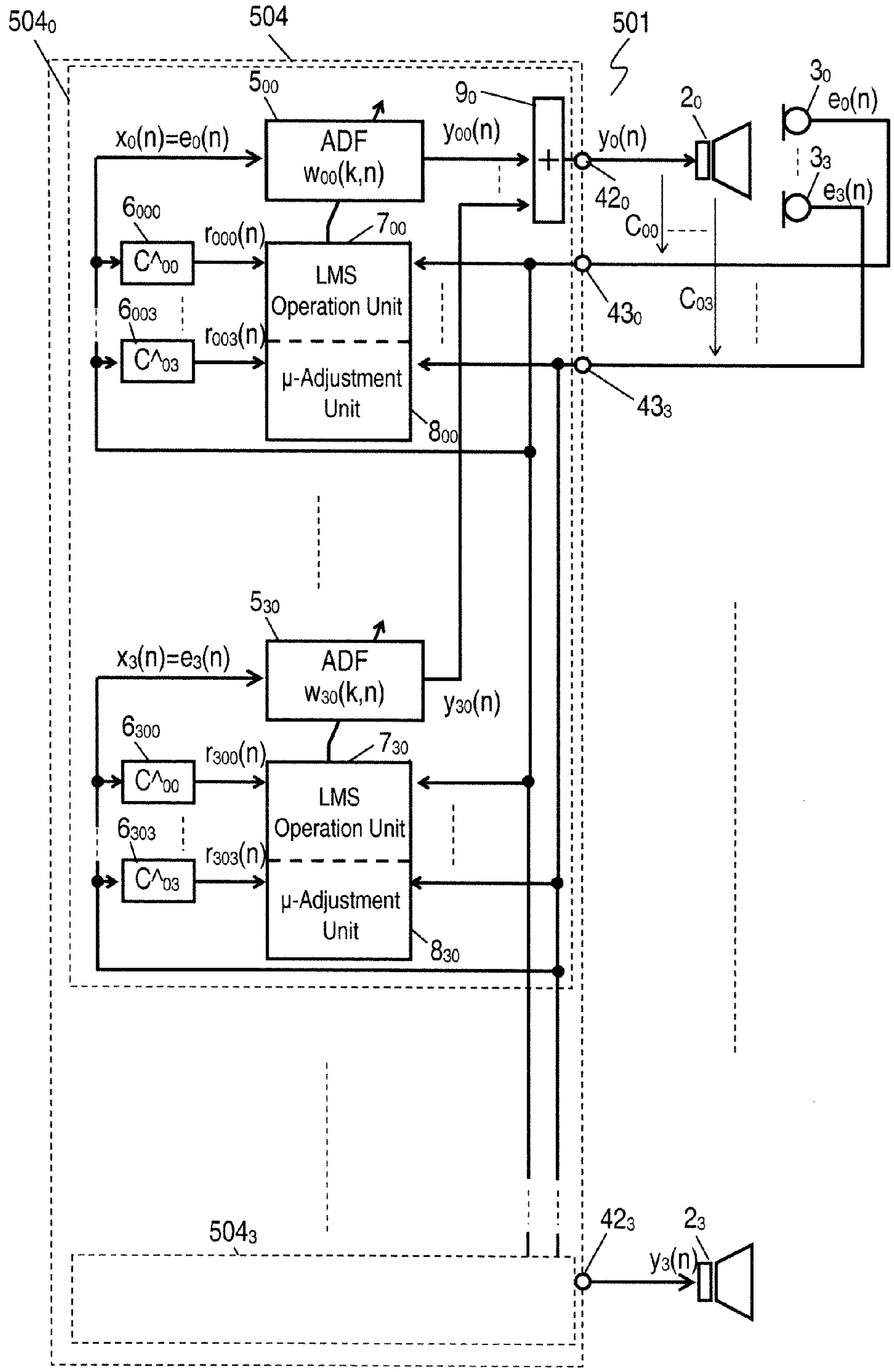
FIG. 16 is a block diagram of the active noise reduction device according to Embodiment 4 for illustrating a particular case.

FIG. 16 is a block diagram of an example of active noise reduction device 501 according to Embodiment 4. As an example of a special case of Embodiment 4, active noise reduction device 501 does not use reference signal generator $10_\eta$, but operates using four error signals $e_\zeta(i)$ as reference signals $x_\xi(i)$. In other words, reference signal generator $10_\eta$ outputs the four error signals $e_\zeta(i)$ as the reference signals $x_\xi(i)$. In this example, the error signals $e_\zeta(i)$ output as the reference signals $x_\xi(i)$ are denoted by $e_\xi(i)$.

Signal-processing device 504 has a configuration similar to that of signal-processing device 404 which does not include reference signal generator $10_\eta$, and which allows error signals $e_\xi(i)$ to be input into ADFs $5_{\xi\eta}$ and Chat units $6_{\xi\eta\zeta}$ instead of the reference signals $x_\xi(i)$. Signal processor $504_0$ that outputs the secondary noise signal $y_0(i)$ includes four sets of ADFs $5_{00}$ to $5_{30}$, LMS operation units $7_{00}$ to $7_{30}$, and μ-adjustment units $8_{00}$ to $8_{30}$. The number "four" is identical to the number of error signals $e_\zeta(i)$. Signal-processor $504_0$ further includes signal adder $9_0$ and sixteen Chat units $6_{000}$ to $6_{303}$. The number "sixteen" is the number of a square of the number of error signal sources $3_0$ to $3_3$.

ADFs $5_{\xi\eta}$ determine the secondary noise signals $y_{\xi\eta}(n)$ at the current n-th step by performing the filtering operation, that is, the convolution operation expressed by formula (136) using the filter coefficients $w_{\xi\eta}(k,n)$ and the error signals $e_\xi(i)$.

$$y_{\xi\eta}(n) = \sum_{k=0}^{N-1} w_{\xi\eta}(k, n) \cdot e_\xi(n-k) \tag{136}$$

Chat units $6_{\xi\eta\zeta}$ have the time-invariant filter coefficients $C\hat{}_{\eta\zeta}$ expressed by formula (137). The filter coefficients simulate the acoustic transfer characteristics $C_{\eta\zeta}(i)$ between output ports $42_\eta$ and input ports $43_\zeta$ for the error signals $e_\zeta(i)$.

$$C\hat{}_{\mu\zeta}=[c\hat{}_{\mu\zeta}(0), c\hat{}_{\mu\zeta}(1), \ldots, c\hat{}_{\mu\zeta}(N_c-1)]^T \tag{137}$$

Chat units $6_{\xi\eta\zeta}$ output the filtered error signals $r_{\xi\eta\zeta}(n)$ instead of the filtered reference signals by performing the operation expressed by formula (139) from the filter coefficients $C\hat{}_{\eta\zeta}$ expressed by formula (137) and the error signals $E_\xi(n)$ expressed by formula (138).

$$E_\xi(n)=[e_\xi(n), e_\xi(n-1), \ldots, e_\xi(n-(N_c-1))]^T \tag{138}$$

$$r_{\xi\eta\zeta}(n)=C\hat{}_{\eta\zeta}{}^T E_\xi(n) \tag{139}$$

The filtered error signals $R_{\xi\eta\zeta}(n)$ with N rows and one column composed of the filtered error signals $r_{\xi\eta\zeta}(i)$ are expressed by formula (140).

$$R_{\xi\eta\zeta}(n)=[r_{\xi\eta\zeta}(n), r_{\xi\eta\zeta}(n-1), \ldots, r_{\xi\eta\zeta}(n-(N-1))]^T \tag{140}$$

The μ-adjustment units $8_{\xi\eta}$ output the current step-size parameters $\mu_{\xi\eta\zeta}(n)$ based on the standard step-size parameters $\mu_{REF,\xi\eta\zeta}$, and at least one signal of the filtered error signals $r_{\xi\eta\zeta}(i)$ and the error signals $e_\zeta(i)$.

LMS operation units $7_{\xi\eta}$ update, by formula (142), the filter coefficients $W_{\xi\eta}(n)$ expressed by formula (141).

$$W_{\xi\eta}(n) = [w_{\xi\eta}(0, n), w_{\xi\eta}(1, n), \ldots, w_{\xi\eta}(N-1, n)]^T \tag{141}$$

$$W_{\xi\eta}(n+1) = W_{\xi\eta}(n) - \sum_{\zeta=0}^{3} \mu_{\xi\eta\zeta}(n) \cdot e_\zeta(n) \cdot R_{\xi\eta\zeta}(n) \tag{142}$$

Signal adders $9_\eta$ sum up the secondary noise signals $y_{\xi\eta}(n)$, as expressed by formula (143), to generate the secondary noise signals $y_\eta(n)$ to be supplied to secondary noise sources $2_\eta$.

$$y_\eta(n) = \sum_{\xi=0}^{3} y_{\xi\eta}(n) \tag{143}$$

As described above, active noise reduction device 501 can determine the optimal secondary noise signals $y_\eta(n)$ that cancel noise N0 at positions of the plural error signal sources $3_\zeta$, and can reduce noise N0 in space S1 by updating the filter coefficients $W_{\xi\eta}(n)$ of ADFs $5_{\xi\eta}$ every sampling period $T_s$ based on formula (142).

Next, an operation of μ-adjustment units $8_{\xi\eta}$ for calculating the step-size parameters $\mu_{\xi\zeta\eta}(n)$ at the current n-th step will be described below.

The μ-adjustment units $8_{\xi\eta}$ calculate the step-size parameters $\mu_{\xi\eta\zeta}(n)$ at the current n-th step from the standard representative input values $d_{REF,\xi\eta\zeta}$ and the standard step-size parameters $\mu_{REF,\xi\eta\zeta}$ based on each of the plural standard filtered error signals $r_{REF,\xi\eta\zeta}(i)$ in the standard driving condition and the representative input values $d_{\xi\eta\zeta}(n)$ corresponding to each of the standard representative input values $d_{REF,\xi\eta\zeta}$.

Similarly to formula (83), each of the standard filtered error signals $R_{REF,\xi\eta\zeta}$ that is a vector with $N_l$ rows and one column composed of the standard filtered error signals $r_{REF,\xi\eta\zeta}(i)$ from the l-th step that is a certain time in the standard driving condition to the past by $(N_l-1)$ steps is defined by formula (144).

$$R_{REF,\xi\eta\zeta}=[r_{REF,\xi\eta\zeta}(l),r_{REF,\xi\eta\zeta}(l-1),\ldots,r_{REF,\xi\eta\zeta}(l-(N_l-1))]^T \qquad (144)$$

Similarly to formula (119), the standard representative input values $d_{REF,\xi\eta\zeta}$ can be given, for example, as constants by formula (145) based on the standard filtered error signals $R_{REF,\xi\eta\zeta}$ in the standard driving condition.

$$d_{REF,\xi\eta\zeta}=\left(\frac{1}{N_l}\sum_{l=0}^{N_l-1}(r_{REF,\xi\eta\zeta}(l))^2\right)^{\frac{1}{2}} \qquad (145)$$

Based on the filtered error signals $R_{m,\xi\eta\zeta}$ expressed by formula (146), the representative input values $d_{\xi\eta\zeta}(n)$ are determined by formula (147) when the standard representative input values $d_{REF,\xi\eta\zeta}$ are expressed by formula (145).

$$R_{m,\xi\eta\zeta}(n)=[r_{\xi\eta\zeta}(n),r_{\xi\eta\zeta}(n-1),\ldots,r_{\xi\eta\zeta}(n-(N_m-1))]^T \qquad (146)$$

$$d_{\xi\eta\zeta}(n)=\left(\frac{1}{N_m}\sum_{m=0}^{N_m-1}(r_{\xi\eta\zeta}(n-m))^2\right)^{\frac{1}{2}} \qquad (147)$$

Similarly to formula (90), for example, the step-size parameters $\mu_{\xi\eta\zeta}(n)$ at the current n-th step are determined by formula (148) by dividing the standard step-size parameters $\mu_{REF,\xi\eta\zeta}$ by the ratio of the representative input values $d_{\xi\eta\zeta}(n)$ to the standard representative input values $d_{REF,\xi\eta\zeta}$.

$$\mu_{\xi\eta\zeta}(n)=\mu_{REF,\xi\eta\zeta}\cdot\frac{1}{\dfrac{d_{\xi\eta\zeta}(n)}{d_{REF,\xi\eta\zeta}}}=\mu_{REF,\xi\eta\zeta}\cdot\frac{d_{REF,\xi\eta\zeta}}{d_{\xi\eta\zeta}(n)} \qquad (148)$$

As described above, μ-adjustment units $\mathbf{8}_{\xi\eta}$ determine the step-size parameters $\mu_{\xi\eta\zeta}(i)$. Even when the error signals $e_\xi(i)$ are large, active noise reduction device 501 operates stably without divergence of the filter coefficients $W_{\xi\eta}(i)$ of all ADFs $\mathbf{5}_{\xi\eta}$. Moreover, even when the error signals $e_\xi(i)$ are small, the converging speed of the filter coefficients $W_{\xi\eta}(i)$ is high, and active noise reduction device 501 can reduce noise N0 effectively.

Next, an operation of calculating the step-size parameters $\mu_{\xi\eta\zeta}(n)$ by setting the filter coefficients $\hat{c}_{\eta\zeta}(i)$ of Chat units $\mathbf{6}_{\eta\zeta}$ as time-invariant constants $\hat{c}_{\eta\zeta}$, and by using the standard error signals $e_{REF,\xi\eta\zeta}(i)$ and the reference signals $x_{\xi\eta\zeta}(i)$ instead of the standard filtered reference signals $r_{REF,\xi\eta\zeta}(i)$ and the filtered reference signals $r_{\xi\eta\zeta}(i)$ will be described similarly to the Embodiment 3

The μ-adjustment units $\mathbf{8}_{\epsilon\eta}$ calculate the step-size parameters $\mu_{\xi\eta\zeta}(n)$ using the standard error signals $e_{REF,\xi}(i)$ and the error signals $e_\xi(i)$ instead of the standard filtered error signals $r_{REF,\xi\eta\zeta}(i)$ and the filtered error signals $r_{\xi\eta\zeta}(i)$. That is, instead of the filtered error signal $R_{m,\xi\eta\zeta}(n)$ expressed by formula (146), the error signals $E_{m,\xi}(n)$ that are vectors each having $N_m$ rows and one column composed of $N_m$ error signals e(i) from the current n-th step to the past by $(N_m-1)$ steps are defined by formula (149).

$$E_{m,\xi}(n)=[e_\xi(n),e_\xi(n-1),\ldots,e_\xi(n-(N_m-1))]^T \qquad (149)$$

Instead of the standard filtered error signals $R_{REF,\xi\eta\zeta}$ each having $N_l$ rows and one column expressed by formula (144) that are the standard filtered error signal $r_{REF,\xi\eta\zeta}(i)$, the standard error signals $E_{REF,\xi}$ that are vectors each having $N_l$ rows and one column composed of $N_l$ standard error signals $e_{REF,\xi}(i)$ from the l-th step that is a certain time in the standard driving condition to the past by $(N_l-1)$ steps are defined by formula (150).

$$E_{REF,\xi}=[e_{REF,\xi}(l),e_{REF,\xi}(l-1),\ldots,e_{REF,\xi}(l-(N_l-1))]^T \qquad (150)$$

The standard representative input values $d_{REF,\xi}$ may be given as constants, for example, by effective values expressed by formula (151) based on the standard error signals $E_{REF,\xi}$ expressed by formula (150).

$$d_{REF,\xi}=\left(\frac{1}{N_l}\sum_{l=0}^{N_l-1}(e_{REF,\xi}(l))^2\right)^{\frac{1}{2}} \qquad (151)$$

The representative input values $d_\xi(i)$ are defined as parameters corresponding to the standard representative input values $d_{REF,\xi}$. In the case that the standard representative input values $d_{REF,\xi}$ are expressed by formula (151), the representative input values $d_\xi(i)$ are calculated from the error signals $E_m(n)$ by formula (152) similarly to the representative input values $d_\xi(n)$ expressed by formula (147).

$$d_\xi(n)=\left(\frac{1}{N_m}\sum_{m=0}^{N_m-1}(e_{m,\xi}(n-m))^2\right)^{\frac{1}{2}} \qquad (152)$$

The μ-adjustment units $\mathbf{8}_{\xi\eta}$ of active noise reduction device 501 can determine the step-size parameters μ(n) at the n-th step by formula (148) using the standard representative input values $d_{REF}$ expressed by formula (151) and the representative input values d(n) expressed by formula (152). Therefore, the number of parameters and arithmetic calculations for updating the step-size parameters can be reduced, and thus active noise reduction device 501 has a lighter processing load of μ-adjustment units $\mathbf{8}_{\xi\eta}$ than active noise reduction device 401.

Exemplary Embodiment 5

Figure 17:
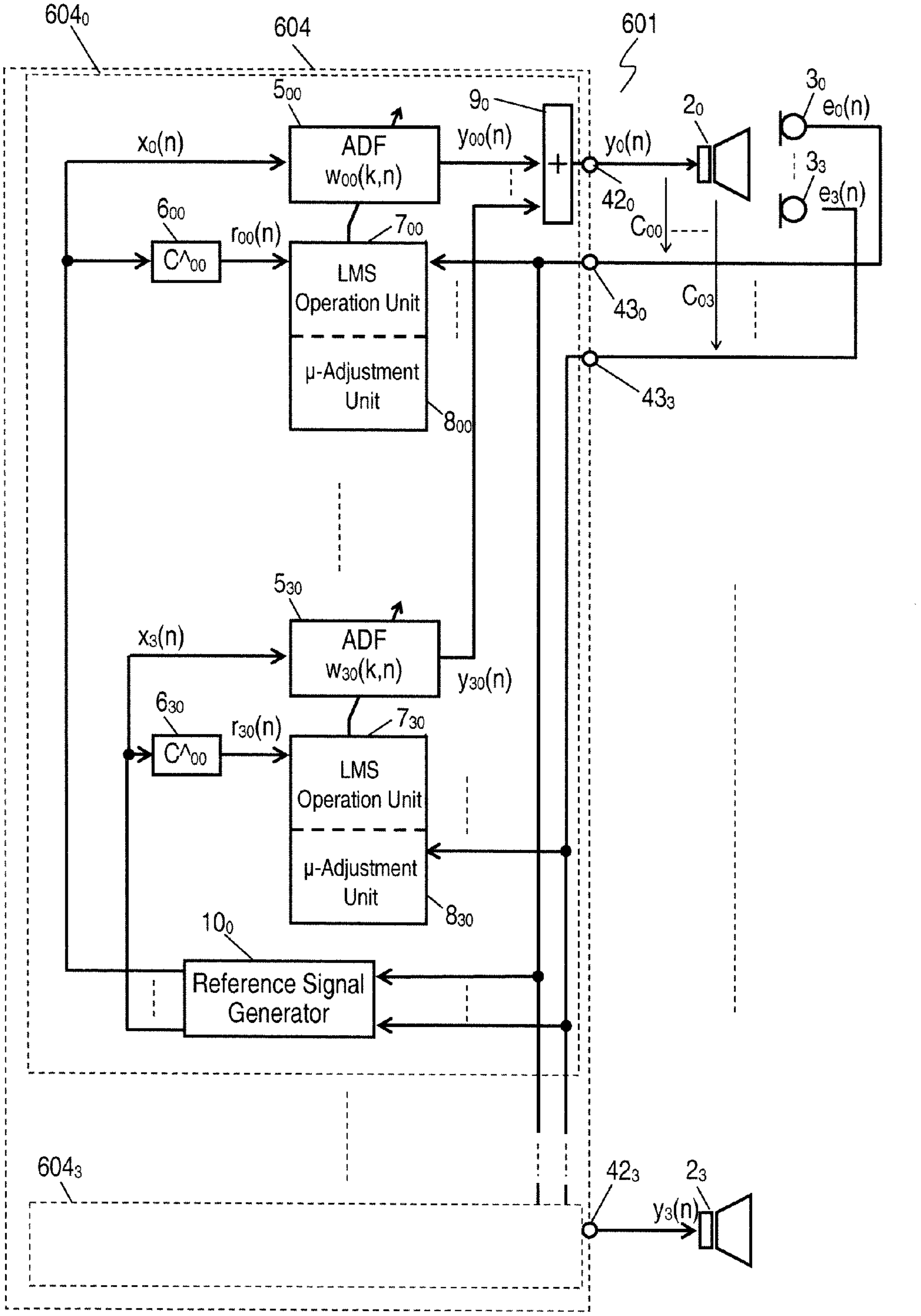
FIG. 17 is a block diagram of an active noise reduction device according to Exemplary Embodiment 5 of the present invention.

FIG. 17 is a block diagram of active noise reduction device 601 according to Exemplary Embodiment 5 of the present invention. In FIG. 17, components identical to those of active noise reduction device 401 according to Embodiment 4 illustrated in FIG. 14 are denoted by the same reference numerals.

Active noise reduction device 601 is a particular device according to Embodiment 4 which can reduce a noise in space S1 due to signal-processing device 604, at least one secondary noise source $\mathbf{2}_\eta$, and at least one error signal source $\mathbf{3}_\zeta$.

Active noise reduction device 601 according to Embodiment 5 has a system configuration of a case (4,4) that includes four secondary noise sources $\mathbf{2}_0$ to $\mathbf{2}_3$ and four error signal sources $\mathbf{3}_0$ to $\mathbf{3}_3$. The device according to Embodiment 5 is a system of the case (4,4). However, the number of secondary noise sources $\mathbf{2}_\eta$ and error signal sources $\mathbf{3}_\zeta$ is not limited to four. The device according to Embodiment 5 may have a configuration of a case (η,ζ) with the numbers different from each other.

Signal-processing device 604 includes plural input ports $\mathbf{43}_{\zeta}$ for acquiring error signals $e_{\zeta}(i)$ output from error signal sources $\mathbf{3}_{\zeta}$, plural output ports $\mathbf{42}_{\eta}$ for outputting secondary noise signals $y_{\eta}(i)$ to secondary noise sources $\mathbf{2}_{\eta}$, and plural signal processors $\mathbf{604}_{\eta}$ for calculating the secondary noise signals $y_{\eta}(i)$.

Each of signal processors $\mathbf{604}_{\eta}$ includes plural ADFs $\mathbf{5}_{\zeta\eta}$, plural Chat units $\mathbf{6}_{\eta\zeta}$, plural LMS operation units $\mathbf{7}_{\zeta\eta}$, plural μ-adjustment units $\mathbf{8}_{\zeta\eta}$, and signal adder $\mathbf{9}_{\eta}$ for outputting a signal obtained by summing up plural signals. Signal processor $\mathbf{604}_{\eta}$ may further include reference signal generator $\mathbf{10}_{\eta}$.

Reference signal generator $\mathbf{10}_{\eta}$ outputs at least one reference signal $x_{\xi}(i)$ based on at least one error signal $e_{\zeta}(i)$. In the device according to Embodiment 5, reference signal generator $\mathbf{10}_{\eta}$ outputs ζ reference signals $x_{\zeta}(i)$ corresponding to the error signals $e_{\zeta}(i)$, respectively.

ADFs $\mathbf{5}_{\zeta\eta}$ determine the secondary noise signals $y_{\zeta\eta}(n)$ by performing a filtering operation, that is, a convolution operation expressed by formula (153) on filter coefficients $w_{\zeta\eta}(k,n)$ and the reference signals $x_{\zeta}(i)$.

$$y_{\zeta\eta}(n) = \sum_{k=0}^{N-1} w_{\zeta\eta}(k, n) \cdot x_{\zeta}(n-k) \tag{153}$$

Chat units $\mathbf{6}_{\eta\zeta}$ have time-invariant filter coefficients $C\hat{}_{\eta\zeta}$ expressed by formula (154). The filter coefficients simulate acoustic transfer characteristics $C_{\eta\zeta}(i)$ between output ports $\mathbf{42}_{\eta}$ and input ports $\mathbf{43}_{\zeta}$ for the error signals $e_{\zeta}(i)$.

$$C\hat{}_{\eta\zeta}=[c\hat{}_{\eta\zeta}(0),c\hat{}_{\eta\zeta}(1), \ldots ,c\hat{}_{\eta\zeta}(N_c-1)]^T \tag{154}$$

Chat units $\mathbf{6}_{\eta\zeta}$ calculate the filtered reference signals $r_{\zeta\eta}(n)$ by performing the filtering operation expressed by formula (155) on the filter coefficients $C\hat{}_{\eta\zeta}$ expressed by formula (154) and a reference signal $X_{\zeta}(n)$.

$$r_{\zeta\eta}(n)=C\hat{}_{\zeta\eta}{}^T X_{\zeta}(n) \tag{155}$$

The reference signal $X_{\zeta}(n)$ is a vector expressed by formula (156) composed of $N_c$ error signals $e_{\zeta}(i)$ ($=x_{\zeta}(i)$) from the current n-th step to the past by $(N_c-1)$ steps.

$$X_{\zeta}(n)=[x_{\zeta}(n),x_{\zeta}(n-1), \ldots ,x_{\zeta}(n-(N_c-1))]^T \tag{156}$$

Filtered reference signal $R_{\zeta\eta}(n)$ with N rows and one column composed of the filtered reference signals $r_{\zeta\eta}(i)$ is expressed by formula (157).

$$R_{\zeta\eta}(n)=[r_{\zeta\eta}(n),r_{\zeta\eta}(n-1), \ldots ,r_{\zeta\eta}(n-(N-1))]^T \tag{157}$$

The μ-adjustment units $\mathbf{8}_{\zeta\eta}$ output current step-size parameters $\mu_{\zeta\eta}(n)$ based on standard step-size parameters $\mu_{REF,\zeta\eta}$ and at least one signal of the reference signals $x_{\zeta}(i)$, the filtered reference signals $r_{\zeta\eta}(i)$, and the error signals $e_{\zeta}(i)$.

LMS operation units $\mathbf{7}_{\zeta\eta}$ update, by formula (159), filter coefficients $W_{\zeta\eta}(n)$ expressed by formula (158).

$$W_{\zeta\eta}(n)=[w_{\zeta\eta}(0,n),w_{\zeta\eta}(1,n), \ldots ,w_{\zeta\eta}(N-1,n)]^T \tag{158}$$

$$W_{\zeta\eta}(n+1)=W_{\zeta\eta}(n)-\mu_{\zeta\eta}(n)\cdot e_{\zeta}(n)\cdot R_{\zeta\eta}(n) \tag{159}$$

Signal adders $\mathbf{9}_{\eta}$ sum up the secondary noise signals $y_{\zeta\eta}(n)$, as expressed by formula (160), to generate the secondary noise signals $y_{\eta}(n)$ to be supplied to secondary noise sources $\mathbf{2}_{\eta}$.

$$y_{\eta}(n) = \sum_{\zeta=0}^{3} y_{\zeta\eta}(n) \tag{160}$$

In active noise reduction device 401 according to Embodiment 4, the filter coefficients $W_{0\eta}(k,n)$ are updated by the error signals $e_0(i)$ to $e_3(i)$. In active noise reduction device 601 according to Embodiment 5, the filter coefficients $W_{0\eta}(k,n)$ are updated by the error signal $e_0(i)$. That is, an error signal that is not consistent with ζ is not used.

As described above, active noise reduction device 601 updates the filter coefficients $W_{\zeta\eta}(n)$ of ADFs $\mathbf{5}_{\zeta\eta}$ every sampling period $T_s$ based on formula (159) so that the device can determine the optimal secondary noise signals $y_{\eta}(n)$ that cancel noise N0 at positions of error signal sources $\mathbf{3}_{\zeta}$, and can reduce noise N0 in space S1.

Next, an operation of μ-adjustment units $N_{\zeta\eta}$ for calculating the step-size parameters $\mu_{\zeta\eta}(n)$ at the current n-th step will be described.

The μ-adjustment units $\mathbf{8}_{\zeta\eta}$ calculate the step-size parameters $\mu_{\zeta\eta}(n)$ at the current n-th step from standard representative input values $d_{REF,\zeta\eta}$ and the standard step-size parameters $\mu_{REF,\zeta\eta}$ based on each of plural standard filtered reference signals $r_{REF,\zeta\eta}(i)$ in a standard driving condition and representative input values $d_{\zeta\eta}(n)$ corresponding to each of the standard representative input values $d_{REF,\zeta\eta}$.

Similarly to formula (84), standard filtered error signal $R_{REF,\zeta\eta}$ that is a vector with $N_l$ rows and one column composed of standard filtered error signals $r_{REF,\zeta\eta}(i)$ from the l-th step that is a certain time in the standard driving condition to the past by $(N_l-1)$ steps is defined by formula (161).

$$R_{REF,\zeta\eta}=[r_{REF,\zeta\eta}(l),r_{REF,\zeta\eta}(l-1), \ldots , r_{REF,\zeta\eta}(l-(N_l-1))]^T \tag{161}$$

The standard representative input values $d_{REF,\zeta\eta}$ can be given as constants, for example, by formula (162) similarly to formula (85) based on the standard filtered reference signals $R_{REF,\eta\zeta}$ in the standard driving condition.

$$d_{REF,\zeta\eta} = \left(\frac{1}{N_l}\sum_{l=0}^{N_l-1}(r_{REF,\zeta\eta}(l))^2\right)^{\frac{1}{2}} \tag{162}$$

The representative input values $d_{\zeta\eta}(n)$ are determined by formula (164) based on the filtered reference signals $R_{m,\zeta\eta}$ expressed by formula (163) in the case that the standard representative input values $d_{REF,\zeta\eta}$ are expressed by formula (162).

$$R_{m,\zeta\eta}(n) = [r_{\zeta\eta}(n), r_{\zeta\eta}(n-1), \ldots , r_{\zeta\eta}(n-(N_m-1))]^T \tag{163}$$

$$d_{\zeta\eta}(n) = \left(\frac{1}{N_m}\sum_{m=0}^{N_m-1}(r_{\zeta\eta}(n-m))^2\right)^{\frac{1}{2}} \tag{164}$$

Similarly to formula (129), the step-size parameters $\mu_{\zeta\eta}(n)$ at the current n-th step are determined by formula (165) by dividing the standard step-size parameters $\mu_{REF,\zeta\eta}$ by a ratio of the representative input values $d_{\zeta\eta}(n)$ to the standard representative input values $d_{REF,\zeta\eta}$.

$$\mu_{\zeta\eta}(n) = \mu_{REF,\zeta\eta} \cdot \frac{1}{\frac{d_{\zeta\eta}(n)}{d_{REF,\zeta\eta}}} = \mu_{REF,\zeta\eta} \cdot \frac{d_{REF,\zeta\eta}}{d_{\zeta\eta}(n)} \quad (165)$$

As described above, μ-adjustment units $\mathbf{8}_{\zeta\eta}$ determine the step-size parameters $\mu_{\zeta\eta}(i)$. Even when the reference signals $x_{\zeta}(i)$ are large, active noise reduction device 601 operates stably without divergence of the filter coefficients $W_{\zeta\eta}(i)$ of all ADFs $\mathbf{5}_{\zeta\eta}$. Moreover, even when the reference signals $x_{\zeta}(i)$ are small, a converging speed of the filter coefficients $W_{\zeta\eta}(i)$ is high, and active noise reduction device 601 can reduce noise N0 effectively.

Exemplary Embodiment 6

Figure 18:
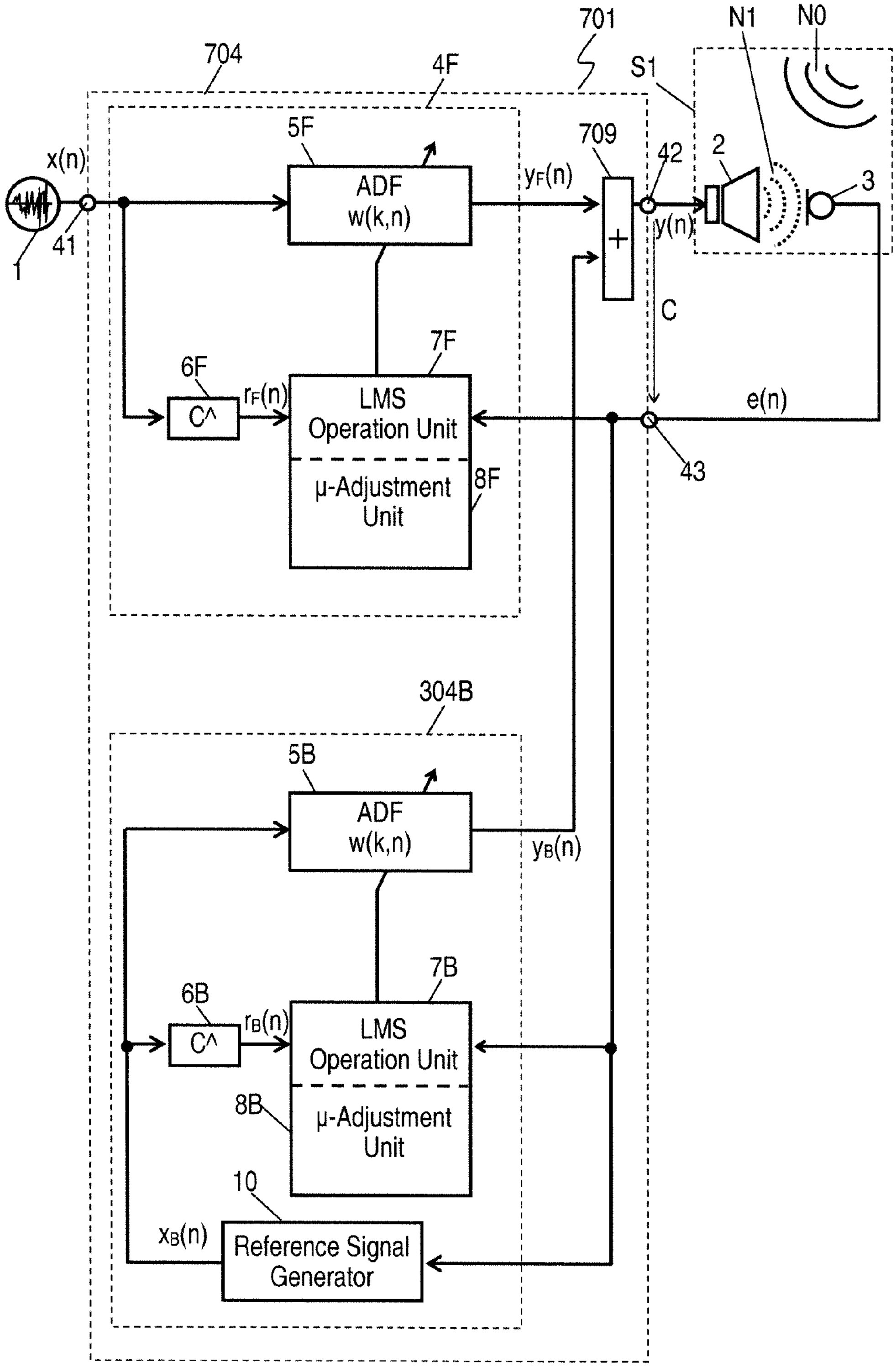
FIG. 18 is a block diagram of an active noise reduction device according to Exemplary Embodiment 6 of the present invention.

FIG. 18 is a block diagram of active noise reduction device 701 according to Exemplary Embodiment 6 of the present invention. In FIG. 18, components identical to those of active noise reduction devices 101 and 301 according to Embodiments 1 and 3 illustrated in FIGS. 1 and 12 are denoted by the same reference numerals. Active noise reduction device 701 includes reference signal source 1, secondary noise source 2, error signal source 3, and signal-processing device 704. Signal-processing device 704 includes signal processors 4F and 304B, and signal adder 709. Signal processor 4F outputs a secondary noise signal $y_F(i)$ in accordance with a reference signal x(i) and an error signal e(i). Signal processor 304B outputs a secondary noise signal $y_B(i)$ in accordance with the error signal e(i). Signal adder 709 sums up the secondary noise signals $y_F(i)$ and $y_B(i)$ to generate a secondary noise signal y(i). Secondary noise source 2 causes secondary noise N1 generated by reproducing the secondary noise signal y(i) to interfere with noise N0 generated in space S1, thereby reducing noise N0.

Signal-processing device 704 includes input port 41 for acquiring the reference signal x(i), input port 43 for acquiring the error signal e(i), and output port 42 for outputting the secondary noise signal y(i).

Signal processor 4F includes ADF 5F, Chat unit 6F, LMS operation unit 7F, and μ-adjustment unit 8F. ADF 5F, Chat unit 6F, LMS operation unit 7F, and μ-adjustment unit 8F have functions similar to functions of ADF 5, Chat unit 6, LMS operation unit 7, and μ-adjustment unit 8 of signal-processing device 4 according to Embodiment 1 illustrated in FIG. 1, respectively. Similarly to ADF 5 according to Embodiment 1, ADF 5F determines the secondary noise signal $y_F(i)$ by performing a filtering operation, that is, a convolution operation on filter coefficients and the reference signals x(i). Similarly to LMS operation unit 7 according to Embodiment 1, LMS operation unit 7F updates the filter coefficient of ADF 5F. Similarly to μ-adjustment unit 8 according to Embodiment 1, μ-adjustment unit 8F determines a step-size parameter $\mu_F(i)$ for updating the filter coefficient of ADF 5F in accordance with at least one reference signal x(i), a filtered reference signal $r_F(i)$, and the error signal e(i).

Signal processor 304B includes ADF 5B, Chat unit 6B, LMS operation unit 7B, and μ-adjustment unit 8B, and may include reference signal generator 10B. ADF 5B, Chat unit 6B, LMS operation unit 7B, μ-adjustment unit 8B, and reference signal generator 10B have functions similar to the functions of ADF 5, Chat unit 6, LMS operation unit 7, μ-adjustment unit 8, and reference signal generator 10 of signal-processing device 304 according to Embodiment 3 illustrated in FIG. 12, respectively. Similarly to ADF 5 according to Embodiment 3, ADF 5B determines the secondary noise signal $y_B(i)$ by performing the filtering operation, that is, the convolution operation on filter coefficients and a reference signal $x_B(i)$. Similarly to LMS operation unit 7 according to Embodiment 3, LMS operation unit 7B updates the filter coefficient of ADF 5B. Similarly to μ-adjustment unit 8 according to Embodiment 3, μ-adjustment unit 8B determines a step-size parameter $\mu_B(i)$ for updating the filter coefficient of ADF 5B in accordance with at least one of the reference signal $x_B(i)$, a filtered error signal $r_B(i)$, and the error signal e(i).

Active noise reduction device 701 ensures stability of ADFs 5F and 5B and a high converging speed regardless of amplitude of the reference signal x(i) or the error signal e(i) similarly to active noise reduction devices 101 and 301 according to Embodiments 1 and 3.

INDUSTRIAL APPLICABILITY

An active noise reduction device according to the present invention ensures stability of an adaptive filter and a high converging speed, and is be applicable to movable bodies including vehicles, such as automobiles.

REFERENCE MARKS IN THE DRAWINGS

1 Reference Signal Source
2 Secondary Noise Source
3 Error Signal Source
4 Signal-Processing Device
4*r* Register
5 Adaptive Filter
6 Simulated Acoustic Transfer Characteristic Filter
7 Least-Mean-Square Operation Unit
8 μ-Adjustment Unit
10 Reference Signal Generator
41 Input Port (First Input Port)
42 Output Port
43 Input Port (Second Input Port)
101 Active Noise Reduction Device
102 Movable Body
103 Active Noise Reduction Device
301 Active Noise Reduction Device
S1 Space

The invention claimed is:

1. An active noise reduction device for reducing a noise, the active noise reduction device being configured to be used with a reference signal source, a secondary noise source, and an error signal source, wherein the reference signal source outputs a reference signal having a correlation with the noise, the secondary noise source generates a secondary noise corresponding to a secondary noise signal, the error signal source outputs an error signal corresponding to a residual sound caused by interference between the secondary noise and the noise, said active noise reduction device comprising a signal-processing device which includes:

a first input port being configured to receive the reference signal;

a second input port being configured to receive the error signal;

an output port being configured to output the secondary noise signal;

an adaptive filter configured to output the secondary noise signal based on the reference signal;

a simulated acoustic transfer characteristic filter configured to correct the reference signal with a simulated acoustic transfer characteristic that simulates an acoustic transfer characteristic from the output port to the second input port so as to output a filtered reference signal;

a least-mean-square operation unit configured to update a filter coefficient of the adaptive filter by using the error signal, the filtered reference signal, and a step-size parameter; and a .mu.-adjustment unit configured to determine the step-size parameter, and wherein the .mu.-adjustment unit is configured to:

calculate a representative input value corresponding to amplitude of at least one signal of the reference signal, the filtered reference signal, and the error signal;

store a standard representative input value and a predetermined standard step-size parameter, the standard representative input value being a representative input value when the amplitude of the at least one signal of the reference signal, the filtered reference signal, and the error signal is predetermined amplitude, the predetermined standard step-size parameter being a value of the step-size parameter to which the filter coefficient converges when the representative input value is the standard representative input value; and calculate the step-size parameter by multiplying the standard step-size parameter by a ratio of the standard representative input value to the representative input value.

2. The active noise reduction device according to claim 1, wherein the standard representative input value corresponds to a maximum value of the amplitude of the at least one signal of the reference signal, the filtered reference signal, and the error signal.

3. The active noise reduction device according to claim 1, wherein the standard step-size parameter takes a maximum value of the step-size parameter to which the filter coefficient converges when the representative input value is the standard representative input value.

4. The active noise reduction device according to claim 1, wherein at least one value of an upper limit value and a lower limit value of a coefficient by which the standard step-size parameter is multiplied is set.

5. The active noise reduction device according to claim 4, wherein the coefficient is a digital value expressed in a register of the signal-processing device having a fixed-point format, and wherein the μ-adjustment unit changes a decimal point position of the coefficient determines to set the at least one value of the upper limit value and the lower limit value of the coefficient.

6. The active noise reduction device according to claim 1, wherein the active noise reduction device is configured to be mounted in a movable body having a space, wherein the noise is generated in the space, wherein the secondary noise source generates the secondary noise in the space, and wherein the residual sound is generated in the space.

7. An active noise reduction device active for reducing a noise, the noise reduction device being configured to be used with a secondary noise source and an error signal source, wherein the secondary noise source generates a secondary noise corresponding to a secondary noise signal, and the error signal source outputs an error signal corresponding to a residual sound caused by interference between the secondary noise and the noise, said active noise reduction device comprising a signal-processing device which includes:

an input port being configured to receive the error signal;

an output port being configured to output the secondary noise signal;

a reference signal generator configured to output a reference signal based on the error signal;

an adaptive filter configured to output the secondary noise signal based on the reference signal;

a simulated acoustic transfer characteristic filter configured to correct the reference signal with a simulated acoustic transfer characteristic that simulates an acoustic transfer characteristic from the output port to the input port so as to output a filtered reference signal;

a least-mean-square operation unit configured to update a filter coefficient of the adaptive filter by using the error signal, the filtered reference signal, and a step-size parameter; and a .mu.-adjustment unit configured to determine the step-size parameter, and wherein the .mu.-adjustment unit is configured to:

calculate a representative input value corresponding to amplitude of at least one signal of the reference signal, the filtered reference signal, and the error signal;

store a standard representative input value and a predetermined standard step-size parameter, the standard representative input value being a representative input value when the amplitude of the at least one signal of the reference signal, the filtered reference signal, and the error signal is predetermined amplitude, the predetermined standard step-size parameter being a value of the step-size parameter to which the filter coefficient converges when the representative input value is the standard representative input value; and calculate the step-size parameter by multiplying the standard step-size parameter by a ratio of the standard representative input value to the representative input value.

8. The active noise reduction device according to claim 7, wherein the standard representative input value corresponds to a maximum value of the amplitude of the at least one signal of the reference signal, the filtered reference signal, and the error signal.

9. The active noise reduction device according to claim 7, wherein the reference signal generator outputs the error signal as the reference signal.

10. An active noise reduction device for reducing a noise, the active noise reduction device being configured to be used with a secondary noise source and an error signal source, wherein the secondary noise source generates a secondary noise corresponding to a secondary noise signal, and the error signal source outputs an error signal corresponding to a residual sound caused by interference between the secondary noise and the noise, said active noise reduction device comprising a signal-processing device which includes:

an input port being configured to receive the error signal;

an output port being configured to output the secondary noise signal;

an adaptive filter configured to output the secondary noise signal based on the error signal;

a simulated acoustic transfer characteristic filter configured to correct the error signal with a simulated acoustic transfer characteristic that simulates an acoustic transfer characteristic from the output port to the input port so as to output a filtered error signal;

a least-mean-square operation unit configured to update a filter coefficient of the adaptive filter by using the error signal, the filtered error signal, and a step-size parameter; and a .mu.-adjustment unit configured to determine the step-size parameter, and wherein the .mu.-adjustment unit is configured to:

calculate a representative input value corresponding to amplitude of at least one signal of the error signal and the filtered error signal;

store a standard representative input value and a predetermined standard step-size parameter, the standard representative input value being a representative input value when the amplitude of the at least one signal of the error signal and the filtered error signal is predetermined amplitude, the predetermined standard step-size parameter being a value of the step-size parameter to which the filter coefficient converges when the representative input value is the standard representative input value; and calculate the step-size parameter by multiplying the standard step-size parameter by a ratio of the standard representative input value to the representative input value.

11. The active noise reduction device according to claim 10, wherein the standard representative input value corresponds to a maximum value of the amplitude of the at least one signal of the error signal and the filtered error signal.

* * * * *